US010662164B2

(12) United States Patent
Chang et al.

(10) Patent No.: US 10,662,164 B2
(45) Date of Patent: May 26, 2020

(54) NON-BETA LACTAM ANTIBIOTICS

(71) Applicant: University of Notre Dame du Lac, South Bend, IN (US)

(72) Inventors: Mayland Chang, Granger, IN (US); Shahriar Mobashery, Granger, IN (US); Edward Spink, Bollington (GB); Derong Ding, Mishawaka, IN (US); Sebastian Testero, Rosario (AR); Erika Leemans, Hamme (BE); Marc Boudreau, Durham, NH (US)

(73) Assignee: University of Notre Dame du Lac, South Bend, IN (US)

( * ) Notice: Subject to any disclaimer, the term of this patent is extended or adjusted under 35 U.S.C. 154(b) by 359 days.

(21) Appl. No.: 15/513,892

(22) PCT Filed: Sep. 25, 2015

(86) PCT No.: PCT/US2015/052474
§ 371 (c)(1),
(2) Date: Mar. 23, 2017

(87) PCT Pub. No.: WO2016/049586
PCT Pub. Date: Mar. 31, 2016

(65) Prior Publication Data
US 2019/0127340 A1 May 2, 2019

Related U.S. Application Data

(60) Provisional application No. 62/055,604, filed on Sep. 25, 2014.

(51) Int. Cl.
*A61K 31/4245* (2006.01)
*C07D 271/107* (2006.01)
*C07D 413/04* (2006.01)
*C07D 471/04* (2006.01)
*C07D 271/06* (2006.01)
*C07F 9/653* (2006.01)

(52) U.S. Cl.
CPC ....... *C07D 271/107* (2013.01); *C07D 271/06* (2013.01); *C07D 413/04* (2013.01); *C07D 471/04* (2013.01); *C07F 9/65318* (2013.01)

(58) Field of Classification Search
None
See application file for complete search history.

(56) References Cited

U.S. PATENT DOCUMENTS

| 5,179,111 | A | 1/1993 | Biere et al. |
| 6,277,872 | B1 | 8/2001 | Brenner et al. |
| 6,737,248 | B2 | 5/2004 | Kunsch et al. |
| 2005/0004005 | A1 | 1/2005 | Kasibhatla et al. |
| 2011/0081297 | A1* | 4/2011 | Barrow ............... C07D 231/12 424/9.3 |
| 2011/0086797 | A1 | 4/2011 | Dworkin |
| 2014/0200226 | A1 | 7/2014 | Chakrabarti et al. |

FOREIGN PATENT DOCUMENTS

| EP | 1501515 B1 | 11/2005 |
| WO | 2003007955 A2 | 1/2003 |
| WO | 2003040112 A1 | 5/2003 |
| WO | 2003087044 A2 | 10/2003 |
| WO | 2003087045 A1 | 10/2003 |
| WO | 2003087046 A1 | 10/2003 |
| WO | 2004048319 A1 | 6/2004 |
| WO | 2005115382 A1 | 12/2005 |
| WO | 2007085451 A2 | 8/2007 |
| WO | 2008097428 A2 | 8/2008 |
| WO | 2009041972 A1 | 4/2009 |
| WO | 2009082398 A1 | 7/2009 |

OTHER PUBLICATIONS

Database Registry Chemical Abstracts Service, Columbus, Ohio, Accession No. RN 1358493-60-3; 1358283-27-8. Entered STN: Feb. 29, 2012.*
Corsaro, A., "The Role of the Hydrogen Bonding in Cycloadditions of Benzonitrile Oxide with Cyanophenols." Tetrahedron, vol. 52, No. 23, 1996, pp. 7885-7892.
International Search Report and Written Opinion of the ISA/US dated Jan. 27, 2016 in International Application No. PCT/US2015/052474; 11pgs.
Nerurkar, et al., "Synthesis and Study of Thiocarbanilides Derived from 2-(4' Aminophenyl) Thiazoles and 4-(4', Aminophenyl) Thiazoles for in vitro Antituberculosis Activity-1," Bulletin of Haffkine Institute, 8(1):27-32, 1980.
O'Daniel et al., "Discovery of a New Class of Non-β-lactam Inhibitors of Penicillin-Binding Proteins with Gram-Positive Antibacterial Activity," J Am Chem Soc., 136(9):3664-3672, Mar. 2014.
Pachhamia, et al., "Studies on 2,5-Disubstituted-1,3,4-oxadiazoles. Part-I. Preparation and Antimicrobial Activity of 2-Aryl-5-(4'-benzenesulphonamidophenyl)/(4'-pyridyl)-1,3,4-oxadiazoles," J Indian Chem Soc., 66(4): 250-251, 1989.
Patil, et al., "Synthesis of Some Sulphanilamido-Benzo-thiazolyl Thiazole Derivatives ai Antibacterial Agents," J Indian Chem Soc., 56(12):1243-1245, 1979.
Pavagadhi, et al., "Synthesis and Antimicrobial Activity of Some New 3-aryl-5-( m-phenoxyphenyl)isoxazoles," Oriental J Chem., 17(2):311-314 (STN Abstract attached), 2001.

(Continued)

Primary Examiner — Samantha L Shterengarts
(74) Attorney, Agent, or Firm — Haukaas Fortius PLLC; Michael H. Haukaas

(57) ABSTRACT

The invention provides a newly discovered oxadiazole class of antibiotics. The oxadiazoles impair cell-wall biosynthesis and exhibit activities against the Gram-positive bacteria such as the bacterium *Staphylococcus aureus*, including methicillin-resistant *S. aureus* (MRSA) and vancomycin-resistant and linezolid-resistant *S. aureus*. For example, 5-(1H-indol-5-yl)-3-(4-(4-(trifluoromethyl)phenoxy)phenyl)-1,2,4-oxadiazole (antibiotic 75b) was efficacious in a mouse model of MRSA infection, exhibiting a long half-life, a high volume of distribution, and low clearance. Antibiotic 75b antibiotic is bactericidal and is orally bioavailable. This class of antibiotics can be used as a therapeutic agent against infections by Gram-positive bacteria such as MRSA.

9 Claims, 50 Drawing Sheets

(56) References Cited

OTHER PUBLICATIONS

Zhou, T., "Hypervalent iodine in synthesis. 75. A convenient synthesis of oxadiazoles by palladium-catalyzed carbonylation and cyclization of diaryliodonium salts and amidoximes." Synthetic Communications, 32(6), 2002, pp. 887-891.

* cited by examiner

Fig. 2

| Oxadiazole antibacterials Compound structure | Oxadiazole Compound No. | LogP | CLogP | E. faecium NCTC 7171 | | S. aureus ATCC 29213 | |
|---|---|---|---|---|---|---|---|
| | | | | MH | MH+ BSA | MH | MH+ BSA |
| [structure] | POD-71-35 | 5.53 | 5.38 | 1 | 128 | 1 | 64 |
| [structure] | EL-188B | 5.68 | 5.51 | 1 | 64 | 1 / 1 | 64 / 64 |
| [structure] | POD-71-01 | 6.45 | 6.26 | 1 | 32 | 1 / 2 | 64 / 32 |
| [structure] | MAB-02-185 | 7.05 | 6.4 | 1 | 32 | 2 | 32 |
| [structure] | POD-176-03 | 5.14 | 4.71 | 32 | 128 | 32 / 16 | >128 / >128 |
| [structure] | DR-01-154 | 5.29 | 5.18 | 8 | >128 | 4 | 64 |
| [structure] | DR-01-184 | 6.06 | 5.92 | 128 | >128 | 32 | >128 |
| [structure] | DR-01-264 | 5.53 | 5.07 | 4 | 64 | >128 | >128 |
| [structure] | DR-01-287 | ? | 4.94 | 16 | >128 | 128 | >128 |
| [structure] | DR-01-168 | 4.96 | 5 | 64 | >128 | 128 | >128 |

| Structure | ID | | | | | | |
|---|---|---|---|---|---|---|---|
| 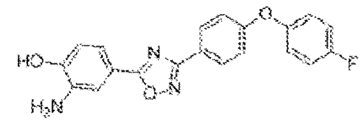 | DR-01-123 | 4.88 | 4.9 | 128 | >128 | >128 | >128 |
| 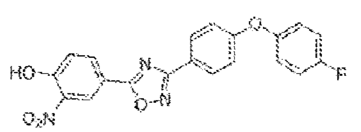 | DR-01-117 | ND | 5.73 | >128 | >128 | >128 | >128 |
| 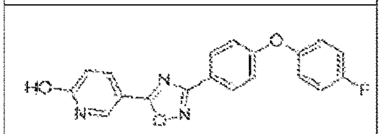 | DR-01-134 | 5.06 | 4.9 | 64 | 128 | >128 | >128 |
| 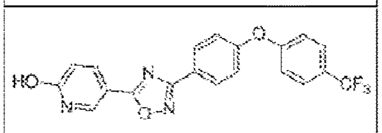 | DR-01-138 | 5.83 | 5.64 | 32 | >128 | >128 | >128 |
| 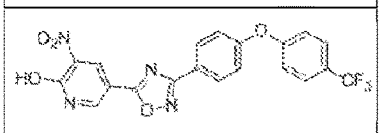 | DR-01-108 | ND | 5.56 | 4 | 128 | 8 | >128 |
| 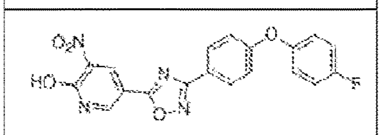 | DR-01-063 | ND | 4.82 | 4 | 128 | 8 | >128 |
| 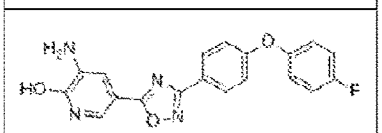 | DR-01-082 | 4.26 | 5.03 | 128 | >128 | >128 | >128 |
| 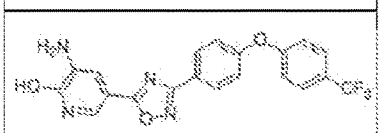 | DR-01-161 | 5.02 | 5.77 | 64 | >128 | >128 | >128 |
| 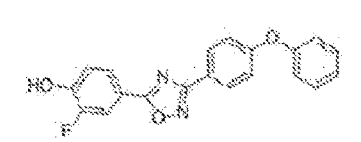 | EL-227(b) | 5.68 | 5.45 | 4 | >128 | 4 | 128 |
| 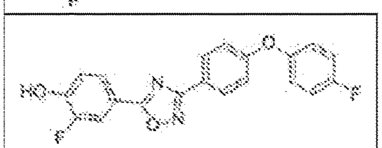 | EL-228(b) | 5.84 | 5.84 | 2 | 128 | 2 | 128 |
| 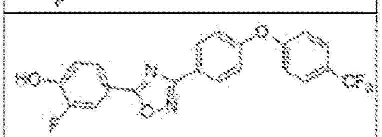 | SAT-207-036 | 6.61 | 6.33 | 2 | 64 | 4<br>2 | 64<br>64 |
| 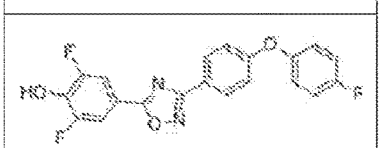 | EL-222(b) | 6 | 5.58 | 4 | >128 | 8 | >128 |

| Structure | ID | | | | | | |
|---|---|---|---|---|---|---|---|
| 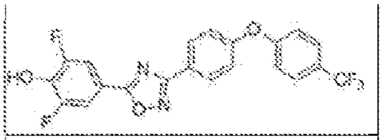 | ES202060 | 6.7 | 6.32 | 2 | >128 | 2 / 2 | >128 / 128 |
| 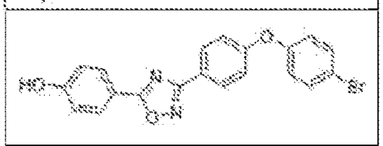 | ES175037 | 6.35 | 6.24 | 1 | >64 | 2 | >256 |
| 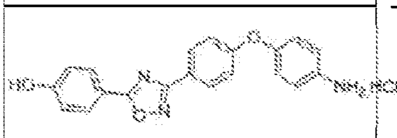 | ES170038 | ? | 4.15 | >32 | | >32 | |
| 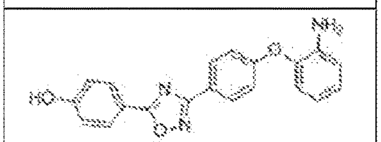 | MAB-01-260A | 4.72 | 4.33 | 128 | >128 | >128 | >128 |
| 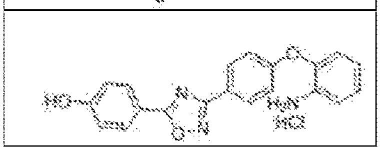 | ES175044 | ? | 4.33 | >32 | | >32 | |
| 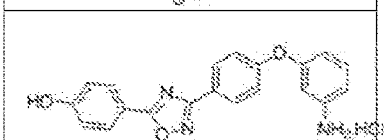 | ES175092 | ? | 4.15 | 64 | 128 | >128 | |
| 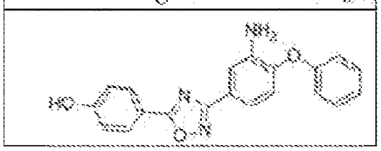 | MAB-02-15A | 4.72 | 4.57 | >128 | >128 | >128 | >128 |
| 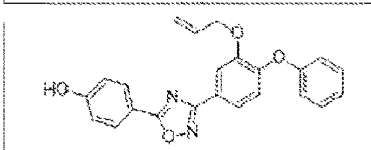 | MAB-02-269A | 6.09 | 5.84 | 4 | 64 | 8 | 64 |
| 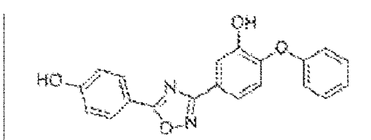 | MAB-02-269B | 5.14 | 4.72 | 8 | 128 | 2 | 32 |
| 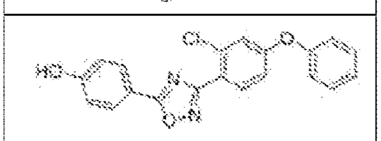 | MAB-01-151A | 6.08 | 5.84 | 2 | 128 | 2 | 128 |
| 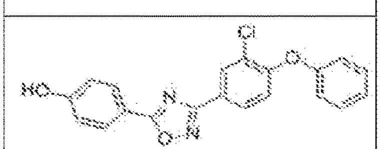 | MAB-01-162A | 6.08 | 5.86 | 2 | 64 | 2 | 64 |
| 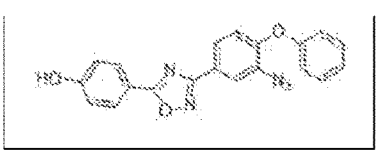 | ES175094 | ND | 6.01 | 2 | >16 | 4 | >16 |

| Structure | ID | | | | | | |
|---|---|---|---|---|---|---|---|
| 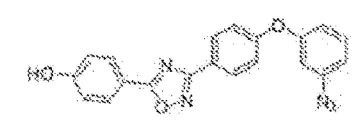 | ES181001 | ND | 5.82 | >128 | | 32 | >128 |
| 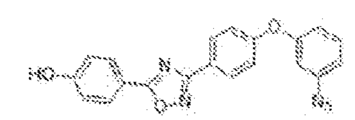 | ES181003 | ND | 5.82 | 64 | >128 | 8 | 64 |
| 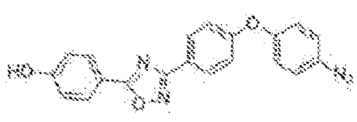 | ES175043 | ND | 5.82 | >128 | | >128 | |
| 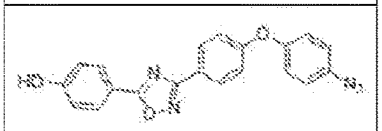 | MAB-01-256A | ND | 5.82 | 0.5 | 64 | 2 | 64 |
| 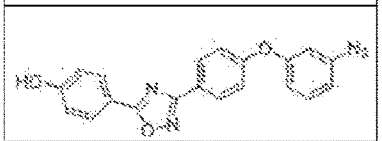 | MAB-01-144A | ND | 5.82 | 1 | 64 | 2 | 64 |
| 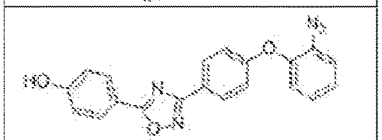 | MAB-02-32A | ND | 5.82 | 1 | 128 | 2 | 128 |
| 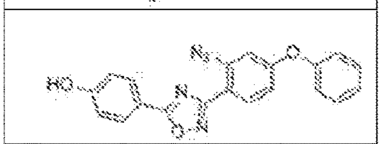 | MAB-02-34A | ND | 6.01 | >128 | >128 | >128 | >128 |
| 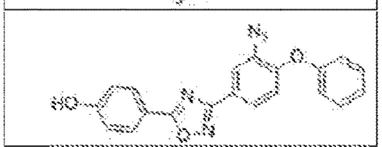 | MAB-02-19A | ND | 6.01 | 2 | 128 | 2 | 128 |
| 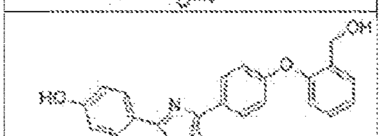 | MAB-02-49A | 4.95 | 4.34 | >128 | >128 | >128 | >128 |
| 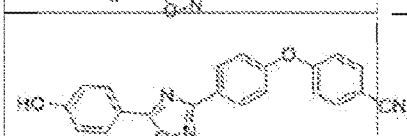 | DR-03-053 | 5.56 | 4.81 | >128 | >128 | >128 | >128 |
| 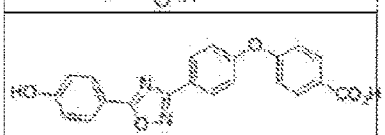 | MAB-01-294A | 5.08 | 5.12 | >128 | >128 | 64 | >128 |
| 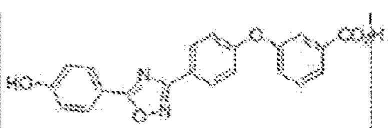 | PN-29 | 5.08 | 5.12 | 128 | >128 | 64 | >128 |

| | | | | | | |
|---|---|---|---|---|---|---|
|  | MAB-02-25A | 5.08 | 4.69 | >128 | >128 | >128 | >128 |
|  | MAB-02-55A | 4.43 | 3.82 | >128 | >128 | >128 | >128 |
|  | ES181071 | 5.98 | 5.37 | 2 | >128 | 4 | 128 |
|  | MAB-01-258A | ? | 4.84 | 2 | 128 | 4 | >128 |
|  | MAB-01-298A | ? | 4.84 | >128 | 128 | 8 | 128 |
|  | MAB-02-23A | ? | 5.12 | 4 | 128 | 4 | >128 |
|  | ES181079 | 7.83 | 7.25 | 2 | 64 | 4 | 128 |
|  | ES175081 | 6.88 | 6.22 | 2 | 64 | 4 | >128 |
|  | EL-50(b) | 5.68 | 5.32 | 16 | 128 | 8 | 128 |
|  | MAB-01-82A | 6.88 | 6.22 | 2 | 128 | 2 | 128 |
|  | MAB-01-140A | 6.88 | 6.5 | 2 | 128 | 4 | 128 |
|  | MAB-01-250A | 6.88 | 6.5 | 0.5 | 64 | 4 | 128 |

| Structure | Name | | | | | |
|---|---|---|---|---|---|---|
|  | ES181085 | 6.35 | 6.24 | 1 | 128 | 4 | 128 |
|  | PN21 | 6.3 | 6.16 | 16 | 128 | >128 | >128 |
|  | PN19 | 6.3 | 6.16 | 4 | 128 | 4 | 32 |
|  | MAB-02-59A | 6.3 | 6.16 | 16 | >128 | 4 | 128 |
|  | PN20 | 6.3 | 6.16 | 8 | 128 | 8 | 128 |
|  | MAB-02-148A | 5.4 | 5.3 | 1 | 64 | 2 | 128 |
|  | POD-93-03 | 4.19 | 3.88 | | | >512 | |
|  | POD-93-05 PN30 | 4.9 | 3.88 | >128 | >128 | >512 >128 | >128 |
|  | POD-93-06 | 4.19 | 3.88 | | | >512 | |
|  | TY3-317 | 3.43 | 2.93 | 16 | 64 | 16 | 32 |
|  | TY3-326 | 2.69 | 2.58 | | | >500 | |
|  | TY3-397 | 3.08 | 1.98 | >500 | >500 | >500 | >500 |

| Structure | Name | | | | | | |
|---|---|---|---|---|---|---|---|
| 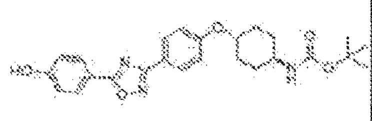 | TY3-475B | 5.19 | 5.11 | | | >256 | >256 |
| 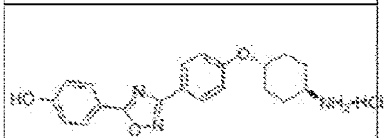 | TY3-479 | ND | 3.36 | >128 | ND | >128 | ND |
| 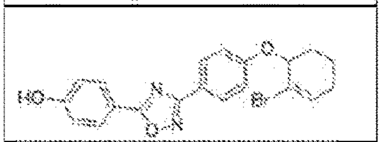 | SAT-187-096 | 5.36 | 5.88 | 1 | 128 | 4 | 128 |
| 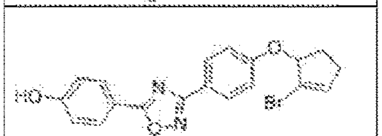 | SAT-207-008 | 4.95 | 5.32 | 1 | 128 | 4 | 128 |
| 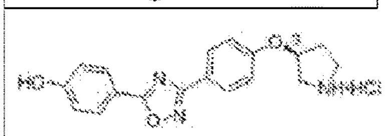 | TY3-437 | ND | 2.92 | 16 | 64 | 16 | 64 |
| 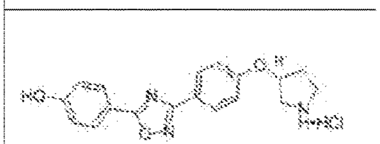 | TY3-440 | ND | 2.92 | 16 | 64 | 16 | 64 |
| 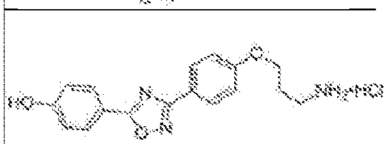 | TY3-478 | ND | 2.92 | 16 | 128 | 16 | 64 |
| 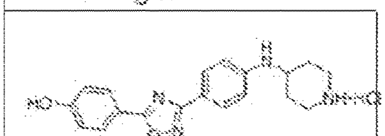 | TY3-484 | ND | 2.65 | 16 | 64 | 8 | 64 |
| 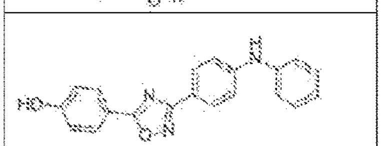 | EL-119(a) | 5.45 | 5.02 | 1 | 128 | 4 | >128 |
| 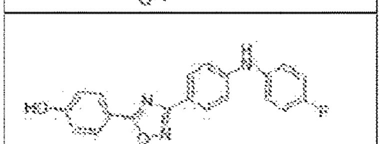 | EL-131(a) | 5.61 | 5.29 | 0.5 | 128 | >128 | >128 |
| 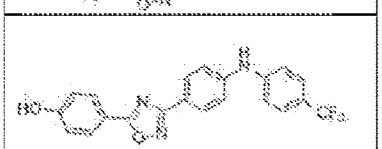 | EL-140(b) | 6.38 | 6.26 | 0.5 | 64 | 32 | >128 |
| 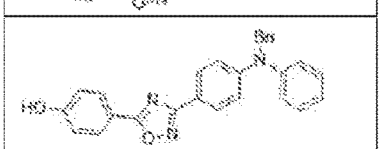 | EL-92(b) | 7.42 | 7.13 | 4 | 64 | >128 | >128 |

| Structure | ID | | | | | | |
|---|---|---|---|---|---|---|---|
| 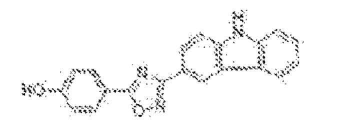 | MAB-01-230A | 4.58 | 4.65 | 32 | 128 | >128 | |
| 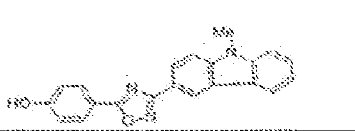 | MAB-01-252A | 4.82 | 5.12 | 1 | 128 | >128 | |
| 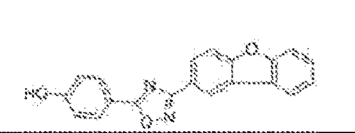 | SAT-187-065 | 4.66 | 5.22 | 2 | 64 | 0.5 8 | 64 >128 |
| 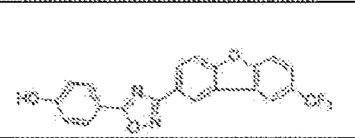 | SAT-187-085 | 5.58 | 6.11 | 2 | 64 | 0.5 1 | 64 64 |
| 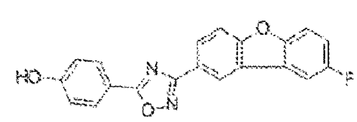 | DR-01-099 | 4.81 | 5.37 | 8 | 32 | >128 | >128 |
| 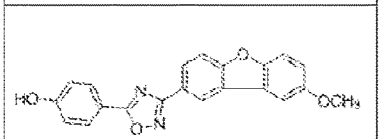 | DR-01-286 | 4.53 | 5.14 | 1 | 32 | >128 | >128 |
| 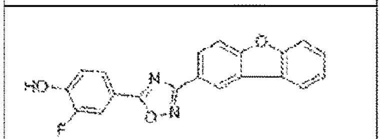 | DR-02-017 | 4.81 | 5.3 | 2 | >128 | 128 | >128 |
| 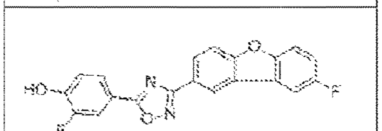 | DR-02-049 | 4.97 | 5.44 | >128 | >128 | >128 | >128 |
| 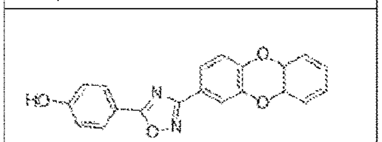 | ES215084 | 4 | 5.57 | >128 | >128 | >128 | >128 |
| 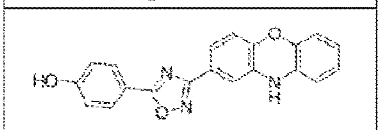 | ES215087 | 3.93 | 5.21 | >128 | >128 | >128 | >128 |
| 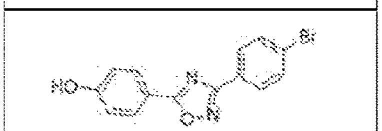 | DR-01-30 | 4.82 | 4.15 | 16 | >128 | >128 | >128 |
| 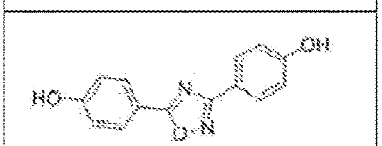 | EL-115(b) | 3.6 | 2.87 | 32 | >128 | >128 | >128 |

| Structure | Name | | | | | | |
|---|---|---|---|---|---|---|---|
| 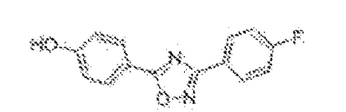 | TY3-444 | 4.15 | 3.43 | 16 | 500 | 500 | >500 |
| 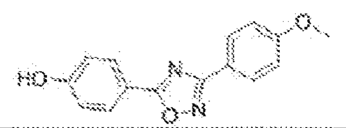 | POD-71-34 | 3.86 | 3.32 | 16 | 128 | 32 | 128 |
| 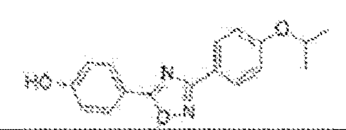 | TY3-454 | 4.52 | 4.16 | 16 | 500 | 16 | 500 |
| 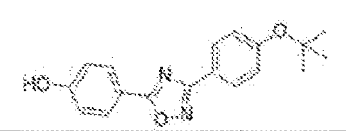 | ES232040 | 4.74 | 4.56 | >128 | >128 | >128 | >128 |
| 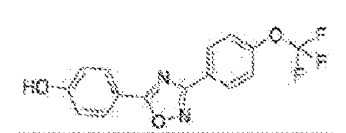 | ES232026 | 5.52 | 4.43 | 16 | 128 | 1 | 64 |
| 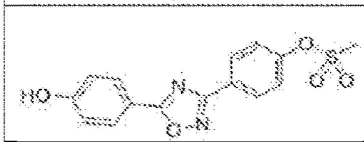 | SAT-187-059 | 2.89 | 2.52 | >128 | | >128 | |
| 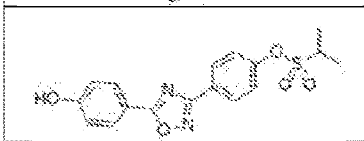 | SAT-187-058 | 3.89 | 3.35 | >128 | | >128 | |
| 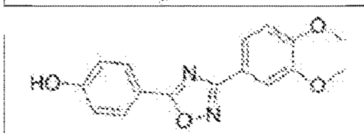 | POD-125-62 | 3.74 | 3.74 | | | >500 | |
| 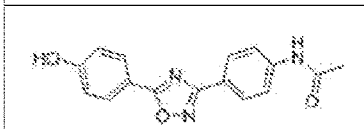 | TY3-271 | 2.9 | 2.52 | | | >500 | |
| 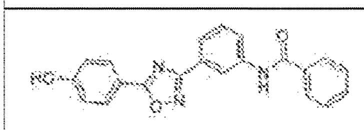 | TY3-294 | 4.79 | 4 | | | >500 | |
| 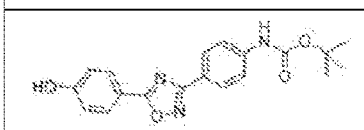 | TY3-473B | 4.36 | 4.17 | 4 | 128 | 8 | 128 |
| 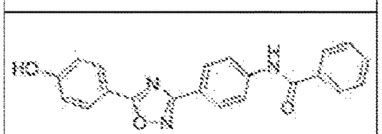 | TY3-295 | 4.79 | 4 | | | >500 | |

| Structure | Compound | | | | | | |
|---|---|---|---|---|---|---|---|
| 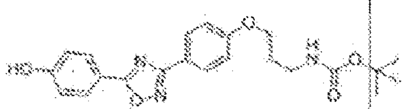 | TY3-474B | 4.46 | 4.71 | | | >256 | >256 |
| 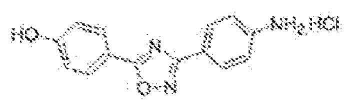 | TY3-477 | ? | 2.29 | | | >256 | >256 |
| 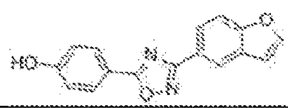 | EL-97(b) | 3.6 | 3.84 | 16 | 64 | 64 | >128 |
| 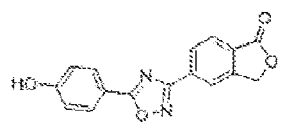 | DR-04-010 | 3.51 | 1.94 | >128 | >128 | >128 | >128 |
| 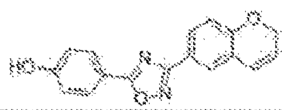 | SAT-207-031 | 4.08 | 3.76 | 16 | 128 | 128 | >128 |
| 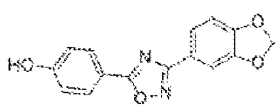 | DR-03-296 | 3.77 | 3.34 | >128 | >128 | >128 | >128 |
| 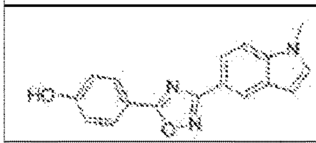 | EL-156(b) | 3.77 | 3.74 | 4 | >128 | 8 | 64 |
| 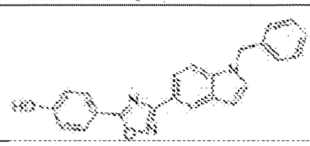 | EL-130(a) | 5.5 | 5.5 | 1 | 64 | 128 | >128 |
| 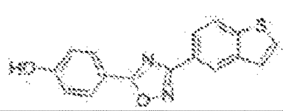 | EL-106(b) | 4.97 | 4.31 | 32 | 64 | >128 | >128 |
| 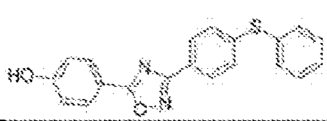 | EL-76(a) | 6.09 | 5.66 | 1 | 64 | 2 | 128 |
| 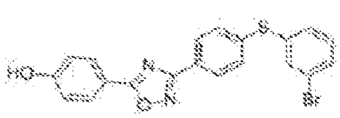 | EL-84(a) | 6.92 | 6.55 | 2 | 128 | 8 | 128 |
| 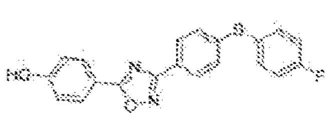 | EL-78(a) | 6.25 | 5.83 | 1 | 64 | 2 | 128 |

| Structure | ID | | | | | | |
|---|---|---|---|---|---|---|---|
| 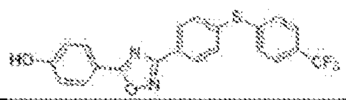 | EL-91(b) | 7.01 | 6.61 | 1 | 32 | 2 | 64 |
| 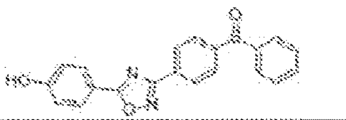 | EL-79(c) | 4.83 | 3.36 | >128 | | >128 | |
| 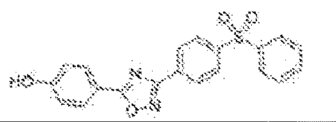 | EL-82(a) | 4.88 | 3.69 | >128 | >128 | >128 | >128 |
| 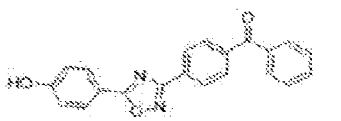 | EL-155c | 5.2 | 4.39 | 2 | >128 | >128 | >128 |
| 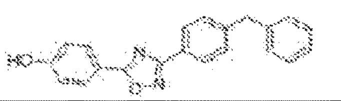 | EL-107(b) | 6.08 | 5.35 | 1 | 64 | >128 | >128 |
| 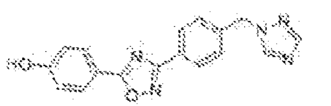 | EL-74(c) | 3.61 | 2.16 | >128 | | >128 | |
| 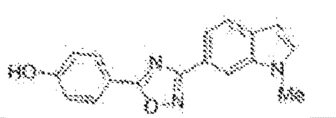 | EL-83(a) | 3.77 | 3.73 | 8 | 128 | 4 / 8 | 64 / 32 |
| 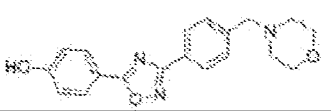 | EL-102(a) | 3.53 | 3.03 | 64 | 128 | >128 | >128 |
| 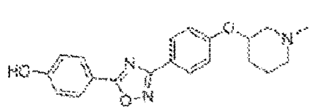 | ES232075 | 4.16 | 4.03 | 64 | 128 | 64 | 128 |
| 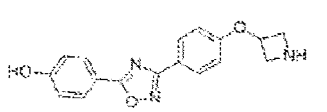 | ES232080 | 3.22 | 2.91 | 64 | 128 | 64 | 128 |
| 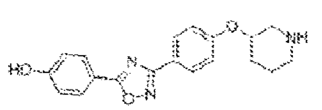 | MAB-03-65 | 3.78 | 3.48 | 64 | 128 | 64 | 128 |
| 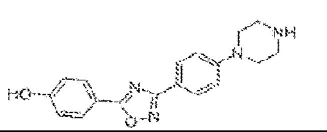 | ES232090 | 3.65 | 2.87 | 64 | 128 | 32 | 64 |

| Structure | ID | | | | | | |
|---|---|---|---|---|---|---|---|
| 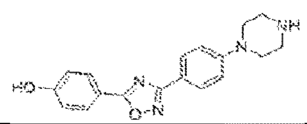 | ES243026 | 3.65 | 2.87 | 32 | 64 | 32 | 64 |
| 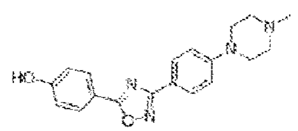 | ES243030 | 4.03 | 3.44 | >128 | >128 | >128 | >128 |
| 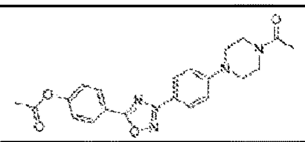 | ES243041 | 3.28 | 2.35 | >128 | >128 | >128 | >128 |
| 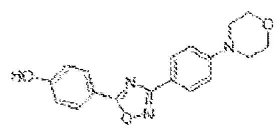 | ES243025 | 3.87 | 2.88 | >128 | >128 | >128 | >128 |
| 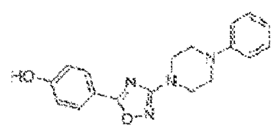 | ES243056 | 4.05 | 3.36 | >128 | >128 | >128 | >128 |
| 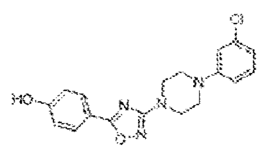 | ES243059 | 4.61 | 4.25 | >128 | >128 | >128 | >128 |
| 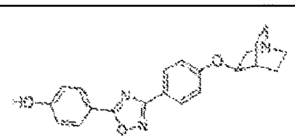 | MAB-03-61 | 4.05 | 3.69 | 32 | 128 | 64 | 128 |
| 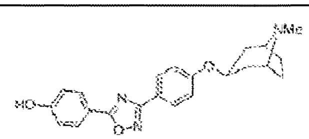 | MAB-03-55 | 4.09 | 3.69 | 32 | 64 | 32 | 128 |
| 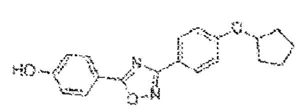 | DR-03-253 | 4.99 | 4.79 | 2 | 32 | 0.5-1 | 32 |
| 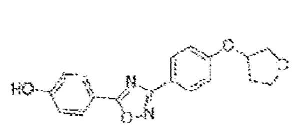 | DR-03-284 | 3.07 | 3.55 | >128 | >128 | >128 | >128 |
| 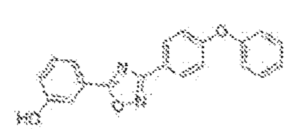 | ES181093 | 5.53 | 5.38 | >128 | | >128 | |
| 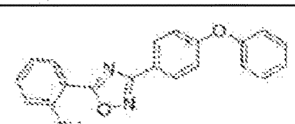 | ES202003 | 5.53 | 5.38 | >128 | | >128 | |

| Structure | ID | | | | | | |
|---|---|---|---|---|---|---|---|
| 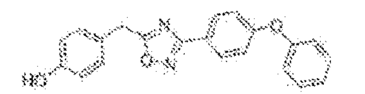 | ES202044 | 5.9 | 5.09 | 8 | >128 | 8 | >128 |
| 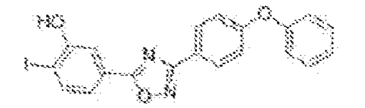 | ES215042 | 6.88 | 6.28 | 32 | 128 | >128 | >128 |
| 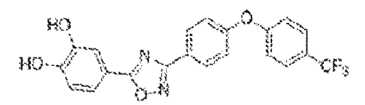 | DR-04-107 | 6.06 | 5.92 | 8 | 64 | 8 | 64 |
| 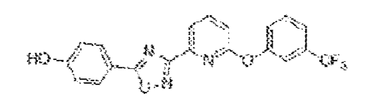 | DR-01-163 | 6.25 | 5.07 | >128 | >128 | >128 | >128 |
| 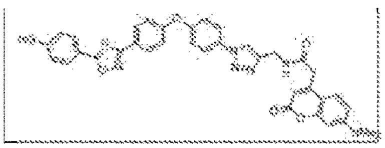 | MAB-02-106A | 6.14 | 5.44 | 32 | >128 | >128 | >128 |
| 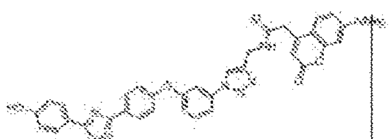 | MAB-02-108A | 6.14 | 5.44 | 32 | >128 | >128 | >128 |
| 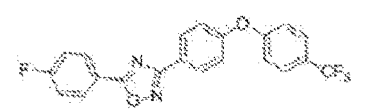 | MIK-B-2 | 6.99 | 6.82 | | | >1200 | |
| 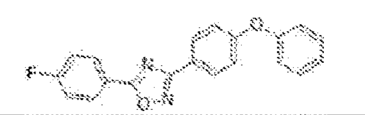 | POD-41-34 | 6.07 | 5.93 | | | >1000 | |
| 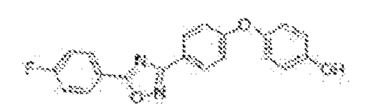 | POD-41-63 | 5.68 | 5.27 | | | >1000 | |
| 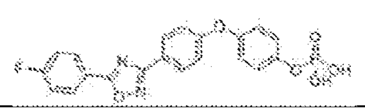 | POD-41-73 | 6.14 | 3.93 | | | >1000 | |
| 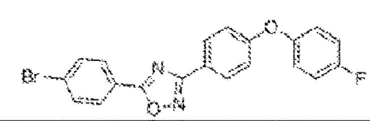 | DR-01-012 | 6.9 | 6.8 | >128 | >128 | >128 | >128 |
| 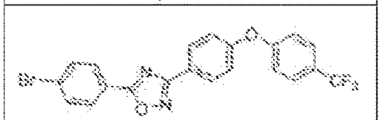 | POD-41-43 | 7.67 | 7.54 | | | >1000 | |

Fig. 2 (Cont.)

| Structure | ID | | | | | | |
|---|---|---|---|---|---|---|---|
| 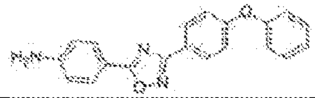 | POD-125-81 | 5.11 | 4.8 | 2 | 64 | 4 | 64 |
| 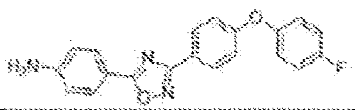 | EL-194B | 5.27 | 4.95 | >128 | >128 | >128<br>>128 | >128<br>>128 |
| 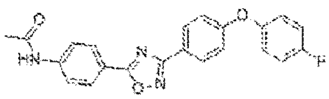 | MAB-03-172 | 4.98 | 5.17 | >128 | >128 | >128 | >128 |
| 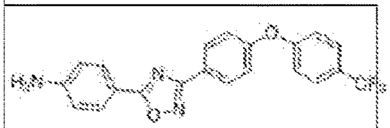 | POD-41-78 | 6.03 | 5.69 | 2 | 32 | 1<br>1 | 32 |
| 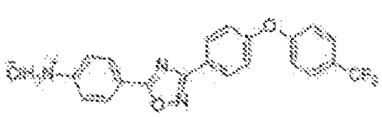 | ES232055 | ? | 5.34 | 2<br>4 | 64<br>64/128 | 8<br>1 | 64<br>16 |
| 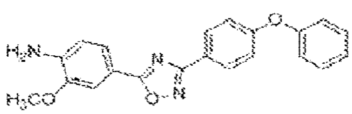 | MAB-02-217 | 4.99 | 5.04 | >128 | >128 | >128 | >128 |
| 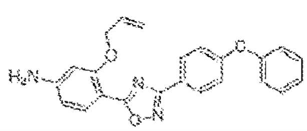 | MAB-02-243 | 5.68 | 5.07 | >128 | >128 | 8 | 32 |
| 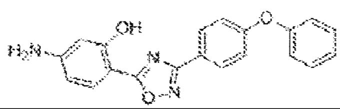 | MAB-02-263 | 4.72 | 4.09 | >128 | >128 | >128 | >128 |
| 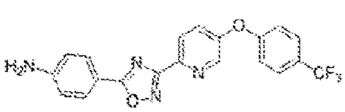 | DR-01-196 | 5.12 | 4.49 | >128 | >128 | >128 | >128 |
| 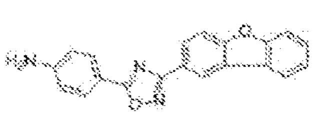 | MAB-02-67A | 4.24 | 4.65 | 32 | >128 | >128<br>>128 | >128<br>>128 |
| 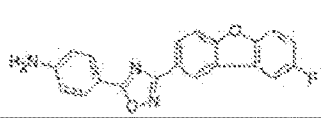 | MAB-02-82A | 4.4 | 4.79 | 64 | 128 | >128<br>>128 | >128<br>>128 |
| 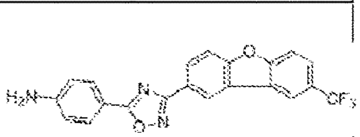 | DR-01-057 | 5.16 | 5.53 | 64 | 128 | >128 | >128 |

| Structure | ID | | | | | | |
|---|---|---|---|---|---|---|---|
| 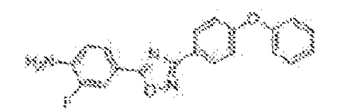 | POD-125-88 | 5.27 | 4.99 | >32 | | >128<br>>128 | >128 |
| 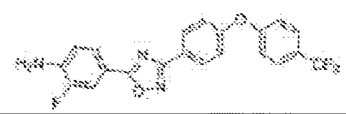 | POD-125-89 | 6.19 | 5.87 | 2 | >128 | 2<br>4 | >128<br>>128 |
| 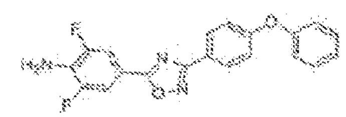 | SAT-169-089 | 5.43 | 5.1 | 4 | 64 | 8<br>8 | 128<br>>128 |
| 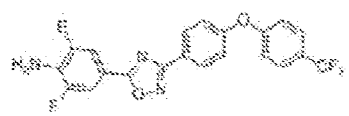 | SAT-169-090 | 6.35 | 5.98 | 4 | 32 | 2<br>4 | 32<br>>128 |
| 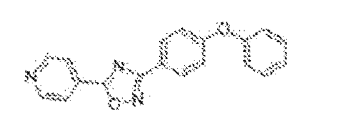 | ES202008 | 4.73 | 4.38 | 64 | >128 | >128 | >128 |
| 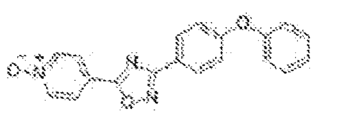 | ES202020 | ? | 3.69 | 64 | >128 | >128 | >128 |
| 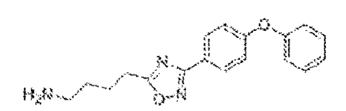 | MAB-02-98A | 4.36 | 3.66 | 64 | >128 | 128 | >128 |
| 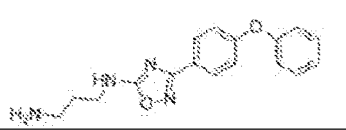 | MAB-02-92A | 3.55 | 4.18 | 32 | 128 | 64 | 128 |
| 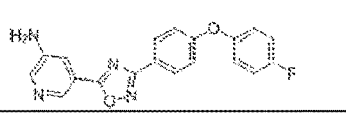 | DR-01-067 | 3.93 | 4.29 | 128 | >128 | >128 | >128 |
| 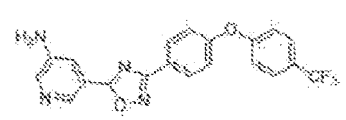 | DR-01-132 | 4.7 | 5.03 | >128 | >128 | >128 | >128 |
| 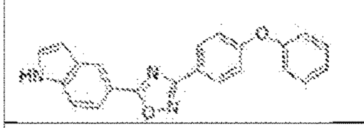 | ES202053A | 5.46 | 5.78 | 2 | 32 | 2<br>2 | 32<br>32 |
| 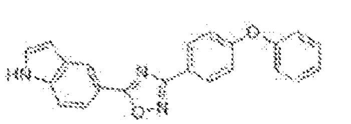 | ES202053B | 5.46 | 5.78 | 4 | 32 | 4 | 32 |

Fig. 2 (Cont.)

| Structure | ID | | | | | | |
|---|---|---|---|---|---|---|---|
| (structure) | ES215039 | 5.61 | 5.92 | 2 | 32 | 2 | 32 |
| (structure) | ES215031 | 6.38 | 6.66 | 2 | 16 | 4 | 16 |
| (structure) | ES243086 (same as ES215031) | 6.38 | 6.66 | 2 | 8 | 2-4 | 8 |
| (structure) | ES243091 | 5.45 | 4.83 | 64 | 128 | >128 | >128 |
| (structure) | ES243090 | 4.54 | 4.65 | >128 | >128 | >128 | >128 |
| (structure) | ES243094 | 5.1 | 5.42 | >128 | >128 | >128 | >128 |
| (structure) | ES202088 | 5.07 | 5.27 | 64 | >128 | >128 | >128 |
| (structure) | DR-01-140 | 5.02 | 5.03 | 64 | >128 | >128 | >128 |
| (structure) | DR-01-143 | 5.78 | 5.77 | 32 | 128 | >128 | >128 |
| (structure) | DR-01-269 | 5.65 | 5.83 | 16 | >128 | >128 | >128 |
| (structure) | DR-02-051 | 6.41 | 6.57 | >128 | >128 | >128 | >128 |
| (structure) | DR-01-125 | 3.81 | 3.95 | 64 | >128 | 128 | >128 |

Fig. 2 (Cont.)

| Structure | ID | | | | | | |
|---|---|---|---|---|---|---|---|
| (structure) | DR-01-127 | ? | 5.78 | 64 | >128 | 8 | 16 |
| (structure) | DR-01-114 | ? | 5.04 | 128 | >128 | >128 | >128 |
| (structure) | DR-01-173 | 4.56 | 4.73 | >128 | >128 | >128 | >128 |
| (structure) | DR-01-203 | 4.19 | 4.87 | 4 | 64 | 2 | 32 |
| (structure) | DR-01-198 | 3.43 | 4.13 | 128 | >128 | >128 | >128 |
| (structure) | DR-03-130 | 3.63 | 3.04 | >128 | >128 | >128 | >128 |
| (structure) | ES243051 | 1.4 | 1.48 | >128 | >128 | >128 | >128 |
| (structure) | ES243061 | 1.79 | 1.98 | >128 | >128 | >128 | >128 |
| (structure) | ES243075 | 2.35 | 2.86 | 64 | >128 | 128 | >128 |
| (structure) | DR-01-011-2 | 4.6 | 4.45 | 32 | 64 | >128 | >128 |
| (structure) | L234-1227 | 5.17 | 4.87 | >128 | >128 | >128 | >128 |
| (structure) | L234-1058 | 3.92 | 3.75 | >128 | >128 | >128 | >128 |

| Structure | ID | | | | | | |
|---|---|---|---|---|---|---|---|
| 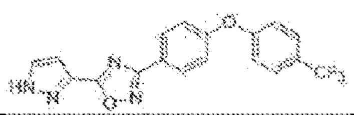 | DR-01-025 | 5.36 | 5.19 | 64 | >128 | >128 | >128 |
| 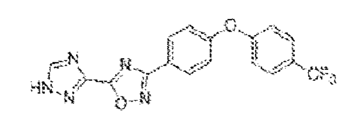 | DR-03-085 | 5.38 | 4.57 | >128 | >128 | >128 | >128 |
| 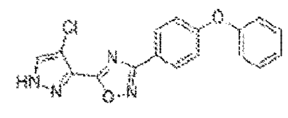 | DR-02-075 | 5 | 4.86 | >128 | >128 | >128 | >128 |
| 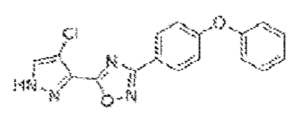 | ES243036 | 5 | 4.86 | >128 | >128 | 1 | 16 |
| 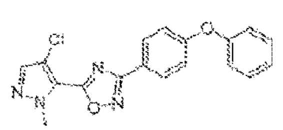 | ES243040 | 4.87 | 4.68 | >128 | >128 | >128 | >128 |
| 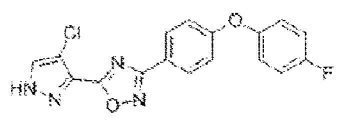 | DR-01-267 | 5.16 | 5.01 | 8 | 128 | 0.5 | 16 |
| 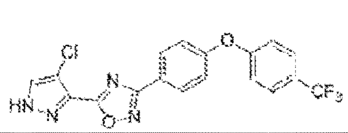 | DR-01-291 | 5.92 | 5.74 | 2 | 128 | 1 | 16 |
| 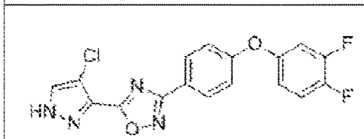 | DR-02-286 | 5.31 | 5.08 | 8 | 64 | 0.5 | 8 |
| 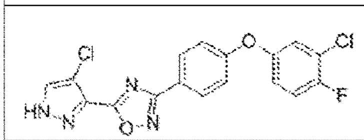 | DR-03-019 | 5.71 | 5.72 | 128 | 128 | 2 | 16 |
| 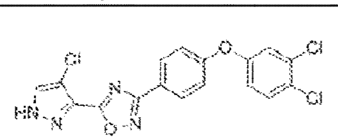 | DR-03-029 | 6.11 | 6.17 | 128 | 128 | 1 | 8 |
| 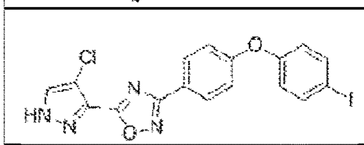 | DR-02-93 | 6.36 | 5.99 | 128 | 128 | 1 | 16 |
| 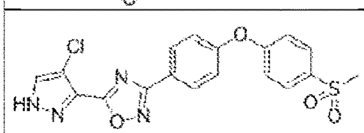 | DR-03-002 | 3.7 | 3.22 | 128 | 128 | 128 | 128 |

Fig. 2 (Cont.)

| Structure | ID | | | | | | |
|---|---|---|---|---|---|---|---|
| (structure) | DR-03-013 | 5.03 | 4.3 | 128 | 128 | 128 | 128 |
| (structure) | DR-03-073 | 4.31 | 4.3 | >128 | >128 | >128 | >128 |
| (structure) | DR-03-153 | 3.62 | 2.91 | >128 | >128 | >128 | >128 |
| (structure) | DR-03-149 | 3.33 | 2.81 | >128 | >128 | >128 | >128 |
| (structure) | DR-03-117 | 4.99 | 3.91 | >128 | >128 | >128 | >128 |
| (structure) | DR-03-261 | 3.63 | 3.05 | >128 | >128 | 32 | 64 |
| (structure) | DR-03-262 | 4.58 | 4.69 | >128 | >128 | >128 | >128 |
| (structure) | DR-03-195 | | | >128 | >128 | >128 | >128 |
| (structure) | DR-03-160 | 3.24 | 2.82 | >128 | >128 | >128 | >128 |
| (structure) | DR-03-259 | ? | 2.36 | >128 | >128 | 8 | 64 |
| (structure) | DR-03-164 | 2.98 | 1.42 | >128 | >128 | >128 | >128 |
| (structure) | DR-04-008 | 3.24 | 3.22 | 16 | 64 | >128 | >128 |

| Structure | ID | | | | | | |
|---|---|---|---|---|---|---|---|
| 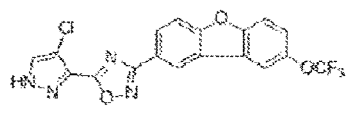 | DR-02-070 | 5.65 | 5.74 | >128 | >128 | >128 | >128 |
| 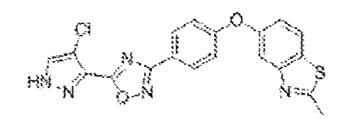 | DR-03-121 | 5.88 | 5.3 | >128 | >128 | >128 | >128 |
| 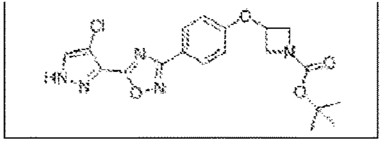 | ES232062 | 3.8 | 4.41 | >128 >128 | >128 | >128 >128 | >128 |
| 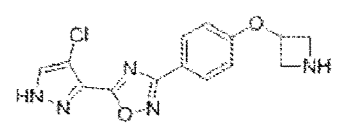 | ES232068 | 2.69 | 2.39 | >128 | >128 | >128 | >128 |
| 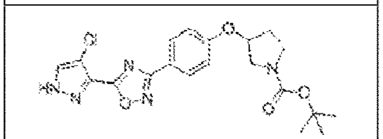 | DR-03-174 | 3.91 | 4.38 | >128 | >128 | >128 | >128 |
| 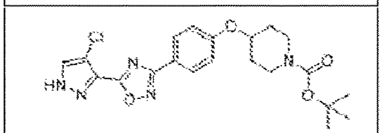 | DR-03-190 | 4.01 | 4.35 | >128 | >128 | >128 | >128 |
| 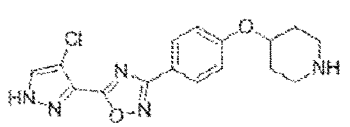 | DR-03-192 | 2.9 | 2.42 | 64 | >128 | >128 | >128 |
| 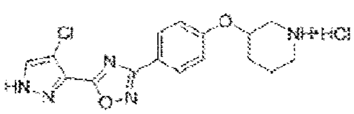 | MAB-03-44 | | | 128 | >128 | >128 | >128 |
| 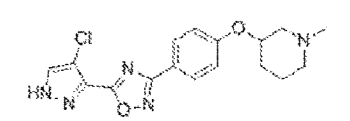 | ES232067 | 3.63 | 3.51 | 128 | >128 | 128 | >128 |
| 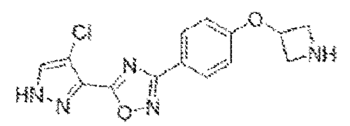 | ES243001 | 2.69 | 2.39 | 128 | >128 | 128 | >128 |
| 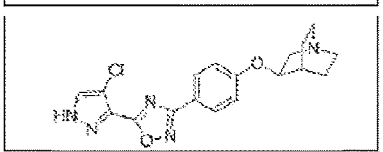 | MAB-03-34 | 3.52 | 3.17 | 128 | >128 | 128 | >128 |
| 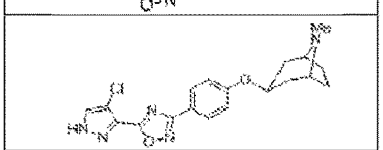 | MAB-03-36 | 3.56 | 3.18 | 64 | 128 | 64 | 128 |

| Structure | ID | | | | | | |
|---|---|---|---|---|---|---|---|
| 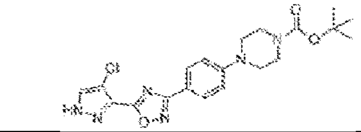 | ES232083 | 4.23 | 4.34 | >128 | >128 | >128 | >128 |
| 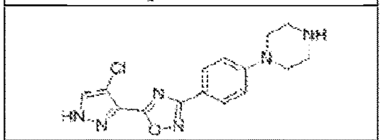 | ES232089 | 3.12 | 2.35 | >128 | >128 | >128 | >128 |
| 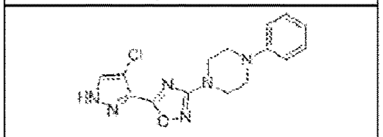 | ES243053 | 3.52 | 2.84 | >128 | >128 | >128 | >128 |
| 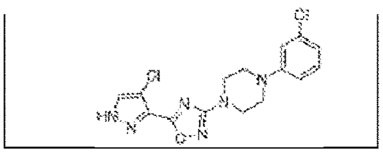 | ES243055 | 4.08 | 3.73 | 8 | 64 | 8 | 32 |
| 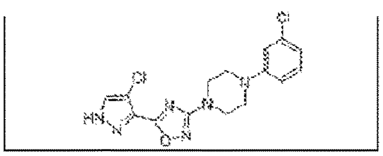 | ES243065 | 4.08 | 3.73 | >128 turbid, no pellet | >128 turbid, no pellet | 16 | 32 |
| 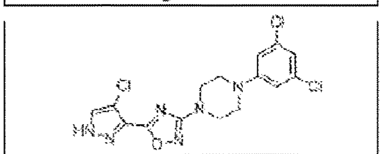 | ES243093 | 4.64 | 4.5 | 128 | >128 | >128 | >128 |
| 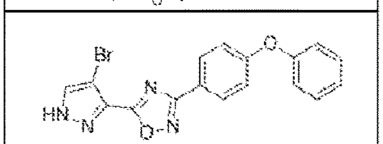 | DR-02-120 | 5.27 | 4.96 | 16 | >128 | 1 | 16 |
| 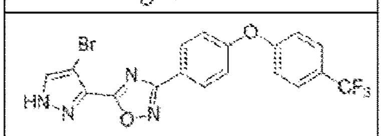 | DR-01-089 | 6.19 | 5.84 | >128 | >128 | 1 | 16 |
| 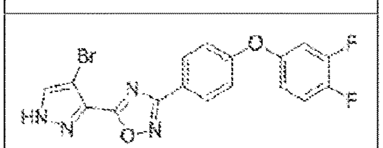 | DR-02-273 | 5.58 | 5.18 | 4 | 32 | 1 | 16 |
| 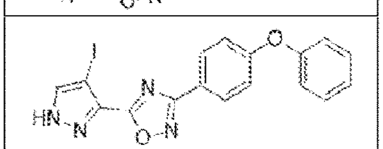 | DR-02-128 | 5.8 | 5.02 | 32 | >128 | 1 | 16 |
| 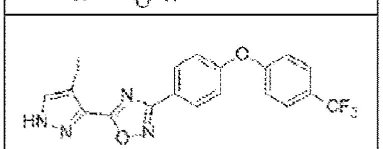 | DR-02-124 | 6.72 | 5.91 | 32 | >128 | 2 | 16 |
| 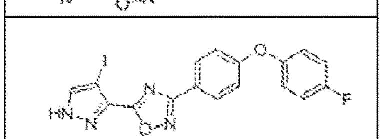 | DR-04-031 | 5.96 | 5.1 | >128 | >128 | 4 | 16 |

| Structure | ID | | | | | | |
|---|---|---|---|---|---|---|---|
| 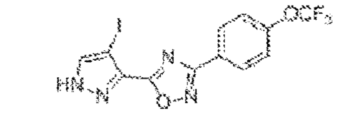 | DR-04-036 | 5.79 | 4.07 | >128 | >128 | >128 | >128 |
| 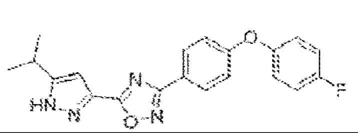 | DR-01-283 | 5.62 | 5.17 | 64 | >128 | >128 | >128 |
| 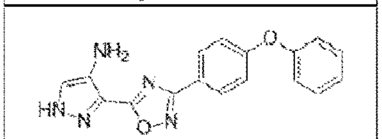 | DR-01-288 | 3.64 | 4 | 32 | >128 | 16 | >128 |
| 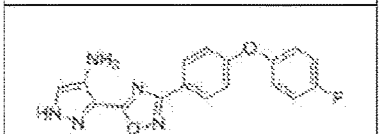 | DR-01-040 | 3.79 | 4.14 | 32 | >128 | 16 | 128 |
| 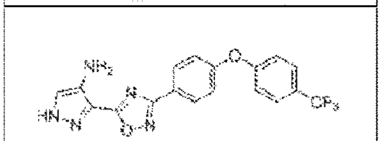 | DR-01-122 | 4.56 | 4.88 | 16 | 128 | 4 | 64 |
| 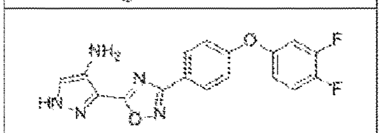 | DR-02-263 | 3.95 | 4.22 | >128 | >128 | 8 | 64 |
| 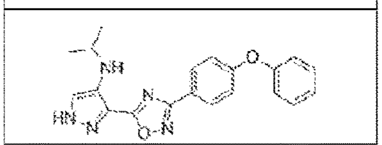 | DR-02-258 | 4.59 | 5.64 | >128 | >128 | 0.5 | 4 |
| 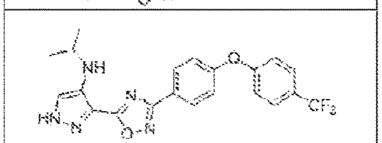 | DR-02-110 | 5.51 | 6.52 | >128 | >128 | 0.5 | 2 |
| 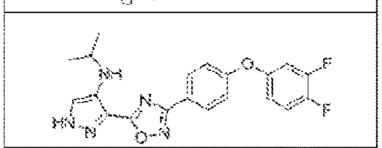 | DR-02-264 | 4.91 | 5.86 | >128 | >128 | 0.5 | 2 |
| 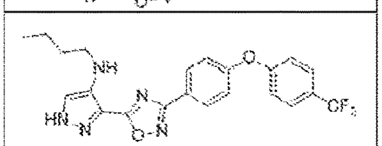 | DR-02-244 | 6.1 | 7.27 | >128 | >128 | >128 | >128 |
| 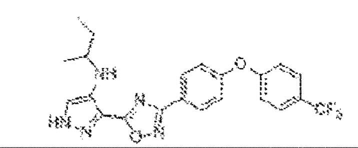 | DR-02-268 | 6 | 7.05 | 128 | >128 | >128 | >128 |
| 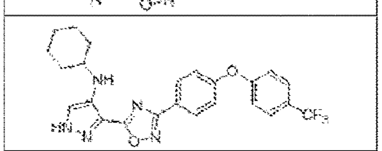 | DR-02-184 | 6.4 | 7.72 | 128 | >128 | >128 | >128 |

| Structure | ID | | | | | | |
|---|---|---|---|---|---|---|---|
| 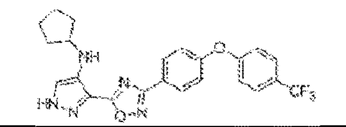 | DR-02-189 | 5.99 | 7.16 | >128 | >128 | >128 | >128 |
| 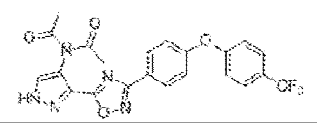 | DR-02-071 | 4.22 | 4.42 | >128 | >128 | >128 | >128 |
| 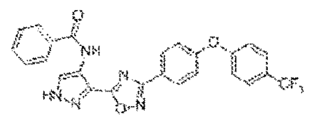 | DR-02-230 | 6.17 | 5.51 | 16 | >128 | >128 | >128 |
| 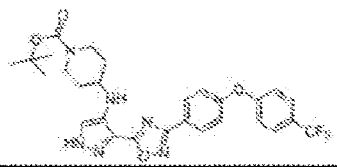 | DR-02-231 | 5.54 | 7.23 | >128 | >128 | >128 | >128 |
| 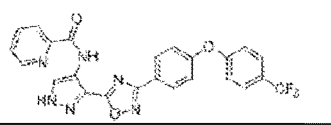 | DR-02-233 | 5.25 | 4.64 | >128 | >128 | >128 | >128 |
| 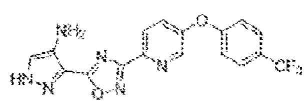 | DR-01-222 | 3.64 | 3.69 | 16 | >128 | 64 | >128 |
| 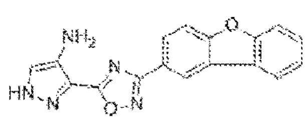 | DR-01-237 | 2.77 | 3.85 | 4 | >128 | >128 | >128 |
| 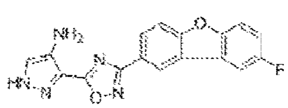 | DR-01-259 | 2.92 | 3.99 | 4 | >128 | >128 | >128 |
| 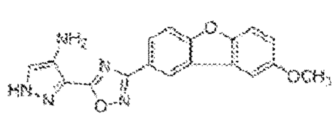 | DR-01-280 | 2.64 | 3.77 | 4 | 32 | >128 | >128 |
| 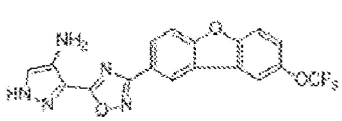 | DR-02-097 | 4.29 | 4.88 | >128 | >128 | >128 | >128 |
| 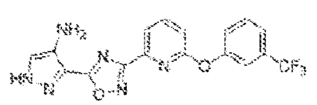 | DR-01-177 | 4.36 | 3.69 | 64 | 128 | >128 | >128 |
| 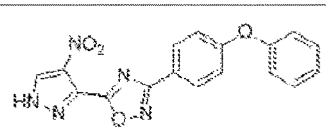 | DR-01-248 | ? | 4.4 | 4 | >128 | 2 | >128 |

| Structure | ID | | | | | |
|---|---|---|---|---|---|---|
|  | DR-01-035 | ? | 4.54 | 4 | >128 | 1: 64<br>2: 128 |
|  | DR-02-261 | ? | 4.61 | >128 | >128 | 2 / 128 |
|  | DR-03-033 | ? | 5.71 | 8 | 128 | 8 / 128 |
|  | DR-01-102 | ? | 5.28 | 2 | 128 | 2 / 128 |
|  | DR-03-006 | ? | 5.52 | 4 | 32 | 8 / 128 |
|  | DR-01-218 | ? | 4.08 | 16 | >128 | >128 / >128 |
|  | DR-02-020 | ? | 2.99 | 16 | 128 | >128 / >128 |
|  | DR-01-263 | ? | 3.96 | 16 | >128 | 128 / >128 |
|  | DR-01-230 | ? | 4.25 | 0.5 | >128 | 2 / 128 |
|  | DR-01-236 | ? | 4.39 | 0.5 | >128 | 32 / 128 |
|  | DR-01-271 | ? | 4.16 | 0.25 | 128 | 32 / 128 |
|  | DR-02-059 | ? | 5.27 | >128 | >128 | 128 / 128 |

| Structure | ID | | | | | | |
|---|---|---|---|---|---|---|---|
| 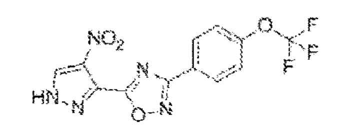 | DR-03-110 | ? | 3.45 | 64 | >128 | 0.5-1 | 32 |
| 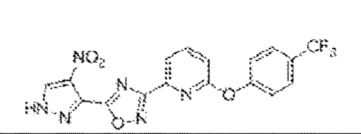 | DR-01-169 | ? | 4.08 | 16 | >128 | 8 | 64 |
| 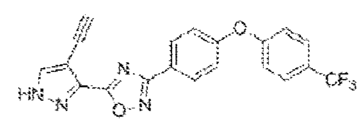 | DR-02-170 | 5.52 | 5.46 | >128 | >128 | 0.25 | 8 |
| 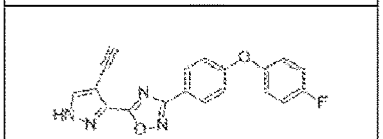 | DR-04-122 | 4.76 | 4.72 | 32 | 128 | 1 | 8 |
| 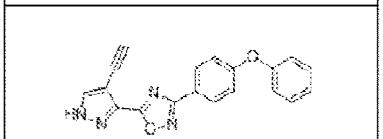 | DR-04-142 | 4.6 | 4.57 | 32 | 128 | 1 | 4-8 |
| 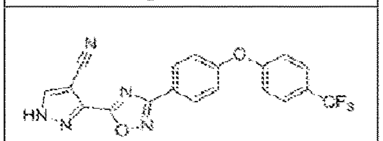 | DR-02-158 | 5.39 | 5.01 | >128 | >128 | 2 | 32 |
| 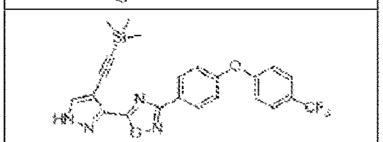 | DR-02-160 | ? | 7.68 | >128 | >128 | >128 | >128 |
| 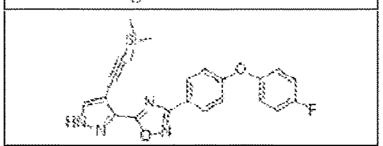 | DR-04-118 | | 6.94 | >128 | >128 | >128 | >128 |
| 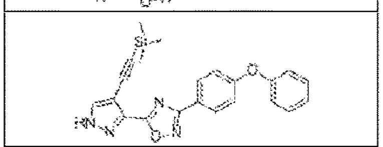 | DR-04-136 | | 6.79 | 64 | >128 | >128 | >128 |
| 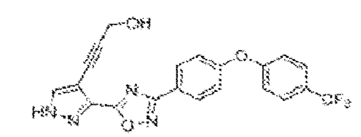 | DR-02-126 | 5.05 | 4 | 128 | >128 | 4 | 32 |
| 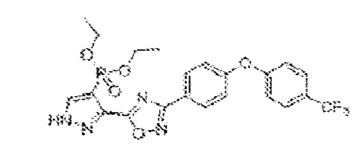 | DR-02-165 | 5.31 | 4.66 | >128 | >128 | >128 | >128 |
| 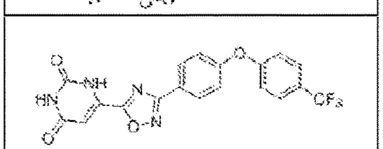 | DR-02-099 | 4.15 | 3.97 | >128 | >128 | >128 | >128 |

Fig. 2 (Cont.)

| Structure | ID | | | | | | |
|---|---|---|---|---|---|---|---|
| 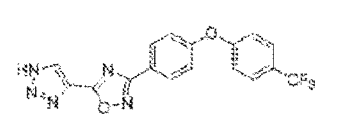 | DR-01-95 | 4.97 | 4.57 | >128 | >128 | 16 | 128 |
| 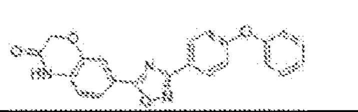 | ES215046 | 4.27 | 4.72 | >128 | >128 | >128 | >128 |
| 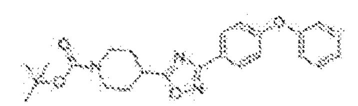 | ES202021 | 5.55 | 5.59 | >128 | >128 | >128 | >128 |
| 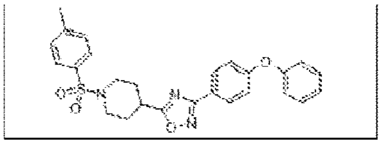 | L234-003 | 6.37 | 5.76 | >128 | >128 | >128 | >128 |
| 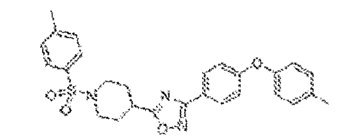 | L234-0301 | 6.86 | 6.25 | >128 | >128 | >128 | >128 |
| 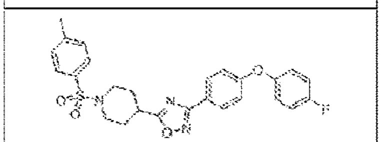 | L234-1065 | 6.53 | 5.9 | >128 | >128 | >128 | >128 |
| 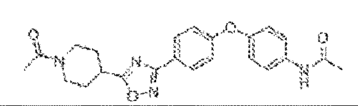 | L234-1023 | 5.28 | 4.78 | >128 | >128 | >128 | >128 |
| 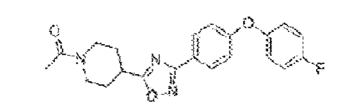 | L234-1192 | 4.25 | 2.85 | >128 | >128 | >128 | >128 |
| 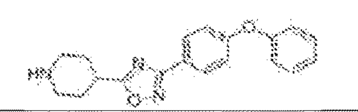 | ES202038 | 4.44 | 3.66 | 16 | 64 | 32 | 128 |
| 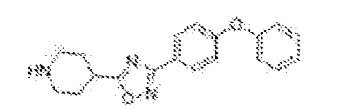 | ES202023 | 4.44 | 3.66 | 64 | 128 | 64 | 64 |
| 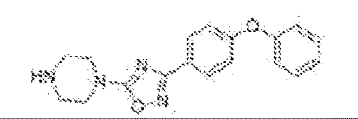 | ES202052 | 4.51 | 3.87 | 32 | 128 | 32 | 128 |
| 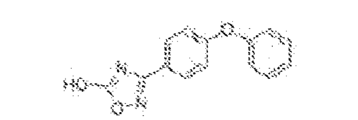 | ES202047 | 4.45 | 4.3 | >128 | | >128 | |

Fig. 2 (Cont.)

| Structure | ID | | | | | | |
|---|---|---|---|---|---|---|---|
| 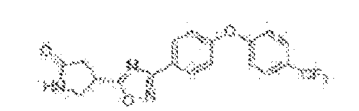 | DR-03-138 | 4.41 | 2.79 | >128 | >128 | >128 | >128 |
| 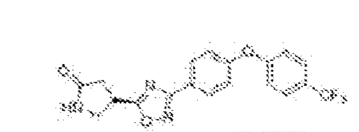 | DR-03-145 | 4.41 | 2.79 | >128 | >128 | >128 | >128 |
| 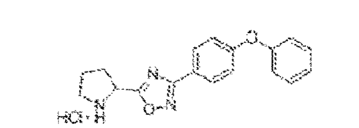 | ES243067 | 4.37 | 3.48 | 64 | >128 | 64 | 128 |
| 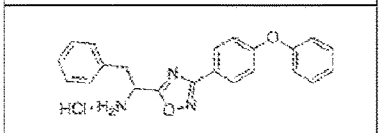 | ES243070 | 5.55 | 4.52 | >128 | >128 | >128 | >128 |
| 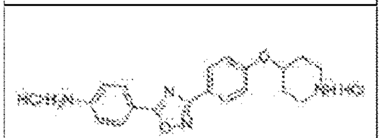 | TY3-510 | ? | 3.43 | >32 | | >32 | |
| 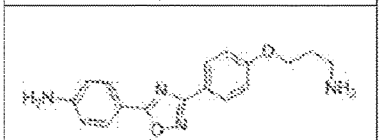 | TY3-513 | 3.32 | 2.37 | >32 | | >32 | |
| 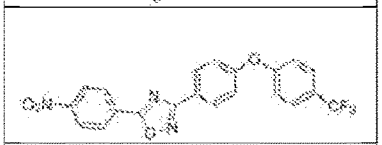 | POD-41-76 | ? | 6.42 | | | >1000 | |
| 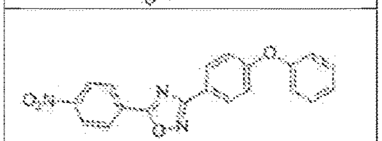 | POD-125-80 | ? | 5.54 | >32 | | >32 | |
| 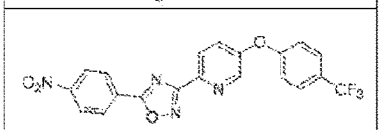 | DR-01-191 | 5.22 | 5.22 | >128 | >128 | >128 | >128 |
| 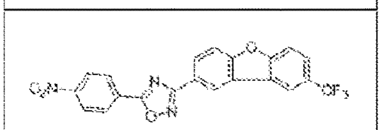 | DR-01-043 | 6.27 | 6.27 | >128 | >128 | >128 | >128 |
| 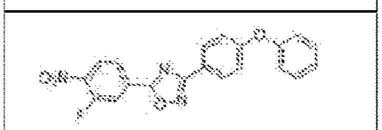 | POD-125-84 | ? | 5.38 | >16 | | >16 | |
| 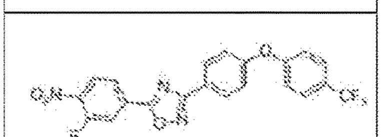 | POD-125-85 | ? | 6.27 | >32 | | >32 | |

Fig. 2 (Cont.)

| Structure | ID | | | | | | |
|---|---|---|---|---|---|---|---|
| 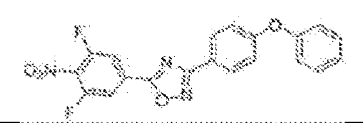 | SAT-169-085 | ? | 5.23 | >128 | | >128 | |
| 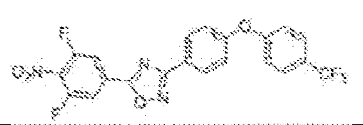 | SAT-169-088 | ? | 6.11 | >128 | | >128 | |
| 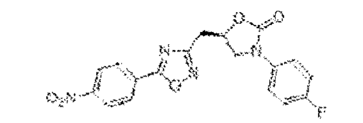 | DR-01-246 | ? | 2.34 | >128 | >128 | >128 | >128 |
| 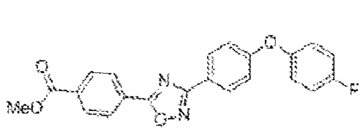 | EL-207 | 5.89 | 5.91 | >128 | >128 | >128 | >128 |
| 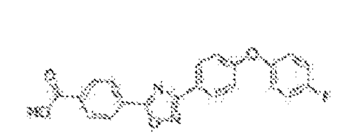 | EL-208 | 5.63 | 5.76 | 128 | >128 | >128 | >128 |
| 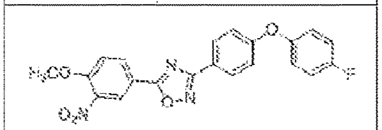 | DR-01-112 | ? | 5.66 | >128 | >128 | >128 | >128 |
| 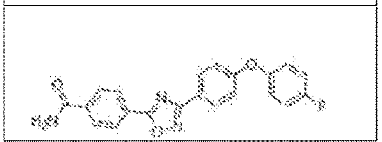 | EL-210 | 4.98 | 4.59 | 64 | >128 | >128 | >128 |
| 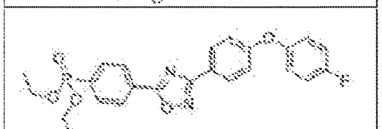 | DR-01-013 | 6.31 | 5.4 | >128 | >128 | >128 | >128 |
| 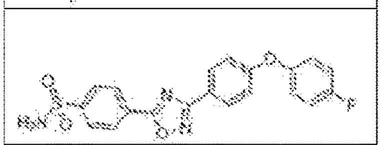 | DR-01-018 | 4.82 | 4.31 | >128 | >128 | >128 | >128 |
| 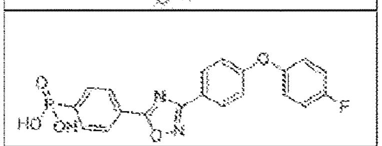 | DR-01-020 | 5.56 | 4.32 | 32 | >128 | >128 | >128 |
| 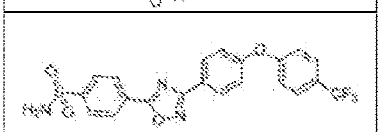 | DR-01-029 | 5.58 | 5.05 | 128 | >128 | >128 | >128 |
| 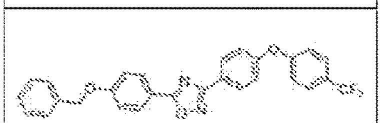 | POD-41-91 | 8.44 | 8.48 | | | >1000 | |

Fig. 2 (Cont.)

| Structure | ID | | | | | | |
|---|---|---|---|---|---|---|---|
| 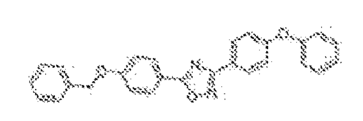 | POD-71-31 | 7.52 | 7.6 | | | >512 | |
| 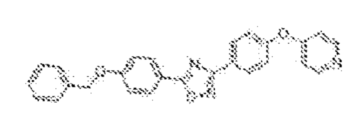 | POD-71-89 | 6.18 | 6.1 | | | >512 | |
| 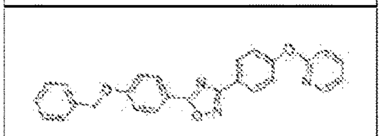 | POD-71-90 | 6.9 | 6.1 | | | >512 | |
| 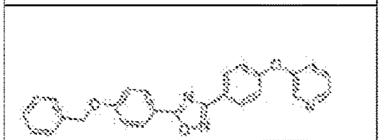 | POD-71-94 | 6.18 | 6.1 | | | >512 | |
| 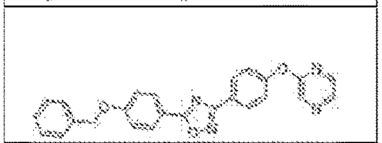 | POD-93-01 | 5.56 | 5.14 | | | >512 | |
| 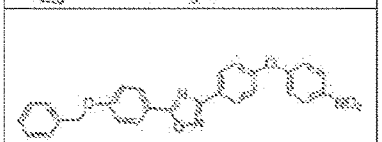 | ES170034 | ? | 7.34 | >256 | | >32 | |
| 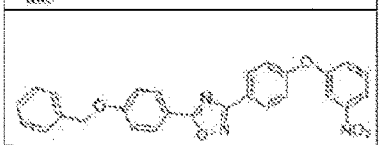 | ES175059 | ? | 7.34 | >128 | | >128 | |
| 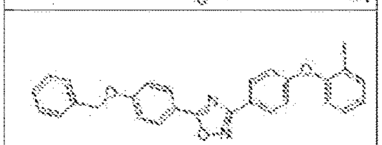 | MAB-01-73A | 8.88 | 8.44 | >128 | | >128 | |
| 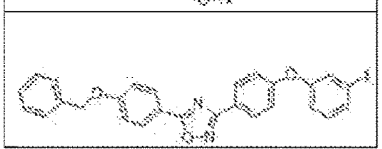 | MAB-01-90A | 8.88 | 8.72 | >128 | | >128 | |
| 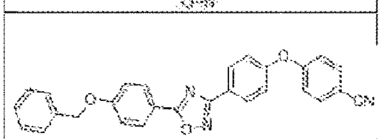 | DR-02-297 | 7.56 | 7.03 | 128 | 128 | 128 | 128 |
| 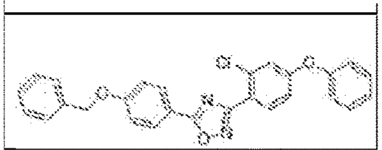 | MAB-01-135A | 8.08 | 8.06 | >128 | | >128 | |
| 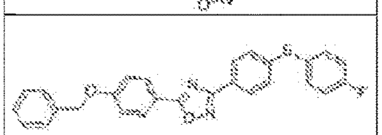 | EL-64(e) | 8.25 | 8.05 | >128 | | >128 | |

| Structure | ID | | | | | | |
|---|---|---|---|---|---|---|---|
| 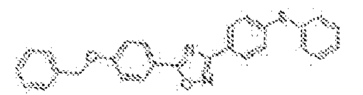 | EL-75(a) | 8.09 | 7.88 | >128 | | >128 | |
| 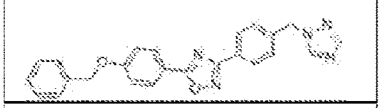 | EL-70(c) | 5.61 | 4.38 | >128 | | >128 | |
| 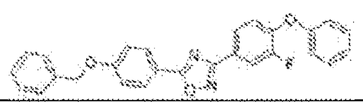 | EL-48(a) | 7.68 | 7.54 | >128 | | >128 | |
| 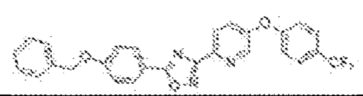 | DR-01-085 | 7.53 | 7.29 | 128 | >128 | >128 | >128 |
| 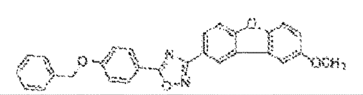 | DR-01-279 | 6.52 | 7.36 | >128 | >128 | >128 | >128 |
| 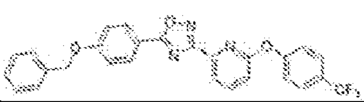 | DR-01-156 | 8.25 | 7.29 | 128 | >128 | >128 | >128 |
| 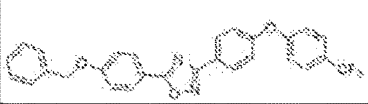 | DR-01-190 | 8.44 | 8.48 | 128 | >128 | >128 | >128 |
| 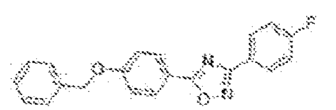 | DR-01-121 | 6.14 | 5.64 | 128 | 32 | >128 | >128 |
| 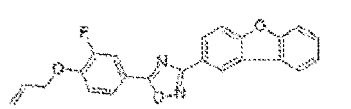 | DR-02-081 | 5.77 | 6.45 | >128 | >128 | >128 | >128 |
| 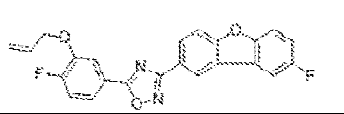 | DR-02-038 | 5.93 | 6.6 | 32 | >128 | >128 | >128 |
| 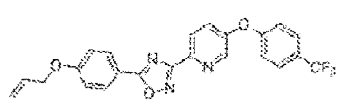 | DR-01-256 | 6.49 | 6.29 | >128 | >128 | >128 | >128 |
| 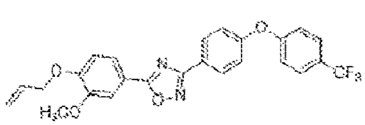 | DR-03-239 | 7.28 | 7.19 | >128 | >128 | >128 | >128 |

| Structure | ID | | | | | | |
|---|---|---|---|---|---|---|---|
| 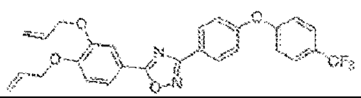 | DR-04-105 | 7.97 | 7.97 | >128 | >128 | >128 | >128 |
| 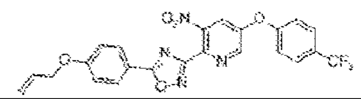 | DR-01-275 | ? | 6.17 | >128 | >128 | >128 | >128 |
| 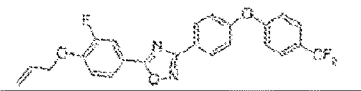 | DR-02-040 | 7.56 | 7.49 | >128 | >128 | >128 | >128 |
| 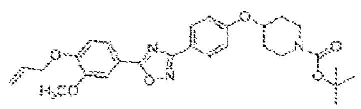 | DR-03-210 | 5.37 | 5.8 | >128 | >128 | >128 | >128 |
| 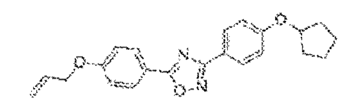 | DR-03-226 | 5.95 | 6.02 | >128 | >128 | >128 | >128 |
| 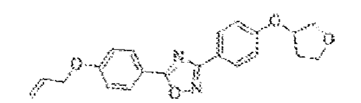 | DR-03-274 | 4.5 | 4.29 | >128 | >128 | >128 | >128 |
| 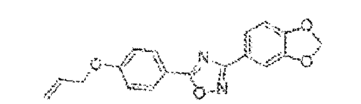 | DR-03-279 | 4.72 | 4.56 | >128 | >128 | >128 | >128 |
| 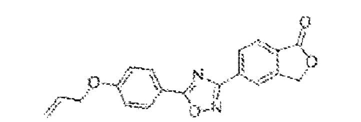 | DR-03-292 | 4.16 | 3.17 | >128 | >128 | >128 | >128 |
| 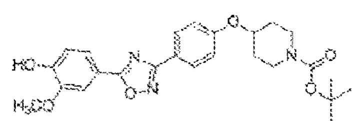 | DR-03-237 | 4.41 | 4.68 | >128 | >128 | >128 | >128 |
| 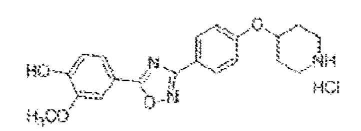 | DR-03-242 | ? | 3.2 | 32 | 128 | 64 | 128 |
| 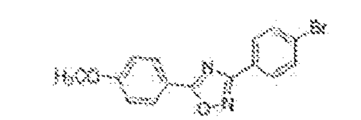 | DR-01-023 | 5.08 | 4.6 | >128 | >128 | >128 | >128 |
| 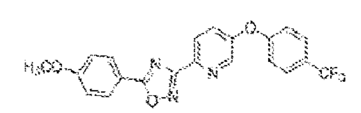 | DR-01-193 | 5.8 | 5.52 | >128 | >128 | >128 | >128 |

| Structure | ID | | | | | |
|---|---|---|---|---|---|---|
|  | MAB-02-145A | ? | 5.52 | 128 | >128 | >128 | >128 |
|  | DR-01-167 | ? | 6.4 | >128 | >128 | >128 | >128 |
|  | MAB-02-152A | 4.99 | 5.04 | >128 | >128 | >128 | >128 |
|  | DR-01-158 | 6.58 | 6.42 | >128 | >128 | >128 | >128 |
|  | DR-03-244 | 6.32 | 6.07 | >128 | >128 | >128 | >128 |
|  | DR-01-148 | 5.82 | 5.68 | >128 | >128 | >128 | >128 |
|  | DR-02-007 | 5.08 | 5.68 | >128 | >128 | >128 | >128 |
|  | DR-01-224 | 5.67 | 5.23 | >128 | >128 | >128 | >128 |
|  | ES181091 | 5.79 | 5.27 | >128 | | >128 | |
|  | ES181090 | 5.79 | 5.83 | >128 | | >128 | |
|  | ES181068 | 6.24 | 5.83 | >128 | | >128 | |
|  | ES181077 | 8.09 | 7.7 | >128 | | >128 | |

| Structure | ID | | | | | | |
|---|---|---|---|---|---|---|---|
| 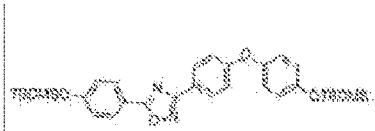 | POD-125-96 | ? | 10.74 | >8 | | >8 | |
| 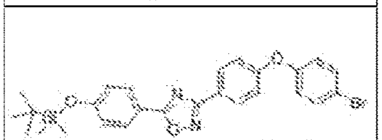 | ES175028 | ? | 8.73 | 2 | 64 | 4 | >256 |
| 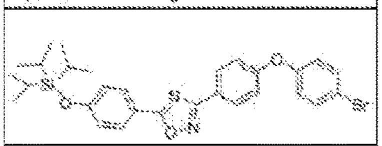 | ES175045 | ? | 10.4 | >32 | | >32 | |
| 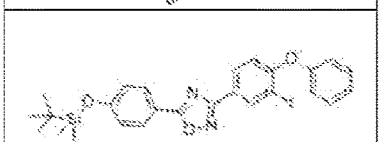 | ES175091 | ? | 8.71 | >128 | | 8 | >128 |
| 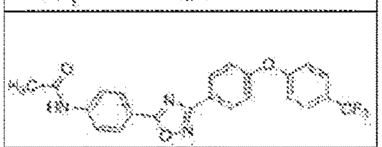 | POD-125-76 | 5.74 | 5.91 | | | 256 | >256 |
| 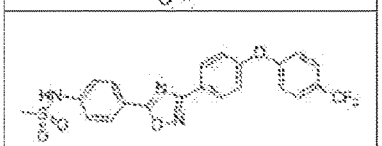 | POD-125-78 | 5.06 | 5.64 | 32 | >128 | >128 | |
| 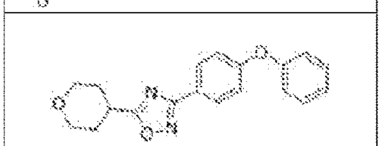 | ES181096 | 4.66 | 3.68 | >128 | | >128 | |
| 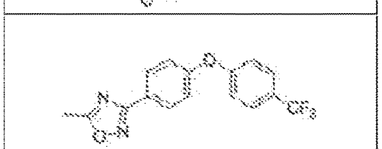 | POD-41-20 | 5.45 | 4.84 | | | >1200 | 1200 |
| 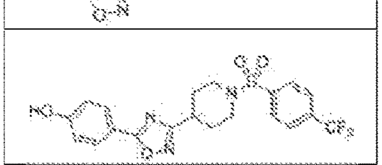 | MAB-01-156A | 4.61 | 3.63 | 64 | >128 | >128 | >128 |
| 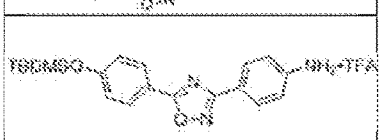 | TY3-480 | ? | | | | >256 | >256 |
| 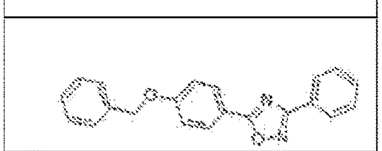 | POD-71-29 | 5.98 | 5 | | | >512 | |
| 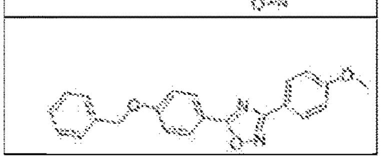 | POD-71-30 | 5.86 | 5.54 | | | >512 | |

| Structure | ID | | | | | | |
|---|---|---|---|---|---|---|---|
| 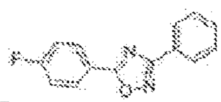 | POD-41-05 | 4.54 | 3.86 | | | >1200 | |
| 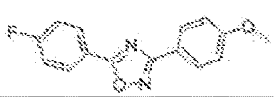 | POD-41-08 | 4.41 | 3.88 | | | >1200 | |
| 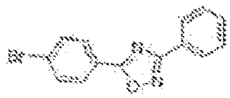 | POD-41-44 | 5.21 | 4.56 | | | >1000 | |
| DIFFERENT B RING: | | | | | | | |
| 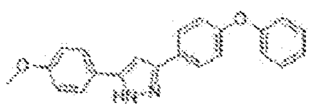 | DISI-004 | 5.37 | 6.57 | >128 | | >128 | |
| 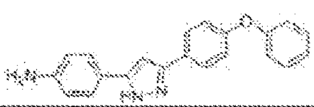 | SAT-187-015 | 4.7 | 5.48 | 8 | 128 | 8 | 128 |
| 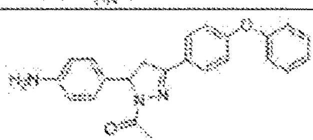 | SAT-187-018 | 3.58 | 4.03 | >128 | | >128 | |
| 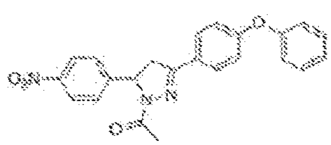 | SAT-187-010 | ? | 5 | >128 | | >128 | |
| 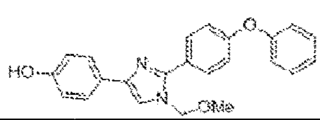 | MAB-03-244 | 4.99 | 5.47 | >128 | >128 | >128 | >128 |
| 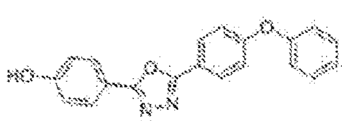 | EL219B | 4.42 | 4.51 | >128 | >128 | >128 | >128 |
| 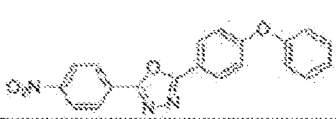 | SAT-187-005 | ? | 4.69 | >128 | | >128 | |
| 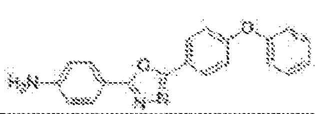 | SAT-187-009 | 4 | 3.93 | >128 | | >128 | |

| Structure | Compound | | | | | | |
|---|---|---|---|---|---|---|---|
| 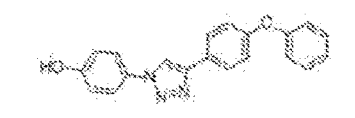 | DISI-002 | 4.89 | 4.89 | 128 | 128 | >128 | >128 |
| 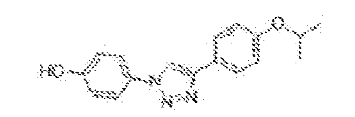 | DISI-012 | 3.88 | 4.33 | >128 | | >128 | |
| 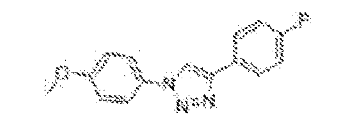 | DISI-015 | 3.77 | 4.17 | 128 | 128 | >128 | |
| 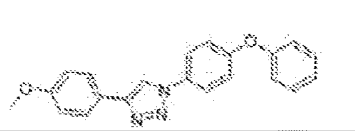 | ES181007 | 5.15 | 5.87 | 128 | 128 | >128 | |
| 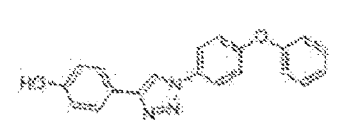 | ES1810011 | 4.89 | 5.31 | 128 | 128 | 128 | >128 |
| 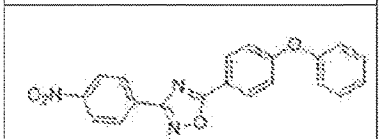 | SAT-187-023 | ? | 5.54 | >128 | | >128 | |
| 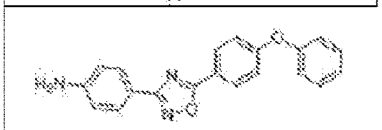 | SAT-187-044 | 5.11 | 4.8 | 4 | 64 | 4 | 64 |
| 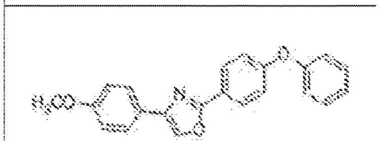 | SAT-169-095 | 4.97 | 6.13 | >128 | | >128 | |
| 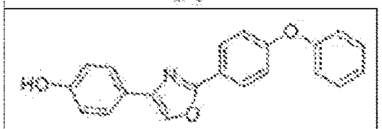 | EL-190 | 4.71 | 5.64 | >128 | >128 | >128 | >128 |
| 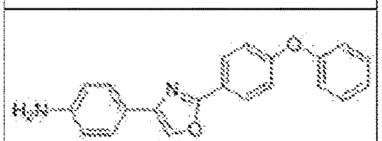 | SAT-187-030 | 4.29 | 5.07 | >128 | | >128 | |
| 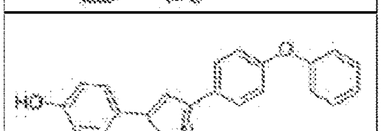 | ES215015 | 5.18 | 5.93 | 32 | >128 | >128 | >128 |
| 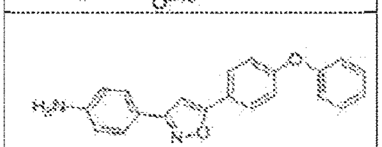 | SAT-187-037 | 4.77 | 5.37 | 128 | | >128 | |

Fig. 2 (Cont.)

| Structure | Compound | | | | | | |
|---|---|---|---|---|---|---|---|
| 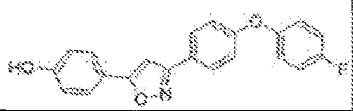 | ES215008 | 5.34 | 6.08 | >128 | >128 | >128 | >128 |
| 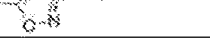 | ES215001 | 5.61 | 6.58 | >128 | >128 | >128 | >128 |
| 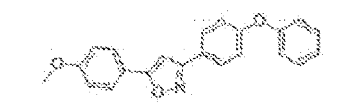 | DISI-005 | 5.45 | 6.44 | 128 | | 16 | >128 |

| Oxadiazole antibacterials Compound number | *K. pneumoniae* ATCC 700603 | | *A. baumanii* ATCC 17961 | | *P. aeruginosa* ATCC 27853 | | *E. aerogenes* ATCC 35029 | | *E. coli* ATCC 25922 | |
|---|---|---|---|---|---|---|---|---|---|---|
| | MH | MH+BSA | MH | MH+BSA | MH | MH+BSA | MH | MH+BSA | MH | MH+BSA |
| POD-71-35 | >128 | ND | >128 | ND | >128 | ND | >128 | ND | >128 | ND |
| EL-188B | >128 | ND | >128 | ND | >128 | ND | >128 | ND | >128 | ND |
| POD-71-01 | >128 | ND | >128 | ND | >128 | ND | >128 | ND | >128 | ND |
| MAB-02-185 | >128 | N/D | >128 | N/D | >128 | N/D | >128 | N/D | >128 | N/D |
| POD-176-03 | >128 | ND | >128 | ND | >128 | ND | >128 | ND | >128 | ND |
| DR-01-154 | >128 | ND | >128 | ND | >128 | ND | >128 | ND | >128 | ND |
| DR-01-184 | >128 | ND | >128 | ND | >128 | ND | >128 | ND | >128 | ND |
| DR-01-264 | >128 | ND | >128 | ND | >128 | ND | >128 | ND | >128 | ND |
| DR-01-287 | >128 | ND | >128 | ND | >128 | ND | >128 | ND | >128 | ND |
| DR-01-168 | >128 | ND | >128 | ND | >128 | ND | >128 | ND | >128 | ND |
| DR-01-123 | >128 | ND | >128 | ND | >128 | ND | >128 | ND | >128 | ND |
| DR-01-117 | >128 | ND | >128 | ND | >128 | ND | >128 | ND | >128 | ND |
| DR-01-134 | >128 | ND | >128 | ND | >128 | ND | >128 | ND | >128 | ND |
| DR-01-138 | >128 | ND | >128 | ND | >128 | ND | >128 | ND | >128 | ND |
| DR-01-108 | >128 | ND | >128 | ND | >128 | ND | >128 | ND | >128 | ND |
| DR-01-063 | >128 | ND | >128 | ND | >128 | ND | >128 | ND | >128 | ND |
| DR-01-082 | >128 | ND | >128 | ND | >128 | ND | >128 | ND | >128 | ND |
| DR-01-161 | >128 | ND | >128 | ND | >128 | ND | >128 | ND | >128 | ND |

*Fig. 2 (Cont.)*

| | | | | | | | | | | |
|---|---|---|---|---|---|---|---|---|---|---|
| EL-227(b) | >128 | ND | >128 | ND | >128 | ND | >128 | ND | >128 | ND |
| EL-228(b) | >128 | ND | >128 | ND | >128 | ND | >128 | ND | >128 | ND |
| SAT-207-036 | >128 | ND | >128 | ND | >128 | ND | >128 | ND | >128 | ND |
| EL-222(b) | >128 | ND | >128 | ND | >128 | ND | >128 | ND | >128 | ND |
| ES202060 | >128 | ND | >128 | >128 | >128 | ND | >128 | >128 | >128 | ND |
| ES175037 | >256 | | >256 | | >256 | | >256 | | >256 | |
| ES170038 | >256 | | >256 | | >256 | | >256 | | >256 | |
| MAB-01-260A | >128 | ND | >128 | >128 | >128 | ND | >128 | >128 | >128 | ND |
| ES175044 | >256 | | >256 | | >256 | | >256 | | >256 | |
| ES175092 | >128 | | >128 | | >128 | | >128 | | >128 | |
| MAB-02-15A | >128 | ND | >128 | >128 | >128 | ND | >128 | >128 | >128 | ND |
| MAB-02-269A | >128 | >128 | >128 | >128 | >128 | >128 | >128 | >128 | >128 | >128 |
| MAB-02-269B | >128 | >128 | >128 | >128 | >128 | >128 | >128 | >128 | >128 | >128 |
| MAB-01-151A | >128 | ND | >128 | ND | >128 | ND | >128 | ND | >128 | ND |
| MAB-01-162A | >128 | ND | >128 | ND | >128 | ND | >128 | ND | >128 | ND |
| ES175094 | >128 | | >128 | | >128 | | >128 | | >128 | |
| ES181001 | >128 | ND | >128 | ND | >128 | ND | >128 | ND | >128 | ND |
| ES181003 | >128 | ND | >128 | ND | >128 | ND | >128 | ND | >128 | ND |
| ES175043 | >128 | ND | >128 | ND | >128 | ND | >128 | ND | >128 | ND |
| MAB-01-256A | >128 | ND | >128 | ND | >128 | ND | >128 | ND | >128 | ND |
| MAB-01-144A | >128 | ND | >128 | ND | >128 | ND | >128 | ND | >128 | ND |
| MAB-02-32A | >128 | ND | >128 | ND | >128 | ND | >128 | ND | >128 | ND |
| MAB-02-34A | >128 | ND | >128 | ND | >128 | ND | >128 | ND | >128 | ND |
| MAB-02-19A | >128 | ND | >128 | >128 | >128 | ND | >128 | >128 | >128 | ND |
| MAB-02-49A | >128 | ND | >128 | ND | >128 | ND | >128 | ND | >128 | ND |
| DR-03-053 | >128 | >128 | >128 | >128 | >128 | >128 | >128 | >128 | >128 | >128 |
| MAB-01-294A | >128 | ND | >128 | >128 | >128 | ND | >128 | >128 | >128 | ND |
| PN-29 | >128 | ND | >128 | >128 | >128 | ND | >128 | >128 | >128 | ND |
| MAB-02-25A | >128 | ND | >128 | >128 | >128 | ND | >128 | >128 | >128 | ND |
| MAB-02-55A | >128 | ND | >128 | ND | >128 | ND | >128 | ND | >128 | ND |
| ES181071 | >128 | ND | >128 | ND | >128 | ND | >128 | ND | >128 | ND |

*Fig. 2 (Cont.)*

| | | | | | | | | | | |
|---|---|---|---|---|---|---|---|---|---|---|
| MAB-01-258A | >128 | ND | >128 | ND | >128 | ND | >128 | ND | >128 | ND |
| MAB-01-298A | >128 | ND | >128 | >128 | >128 | ND | >128 | >128 | >128 | ND |
| MAB-02-23A | >128 | ND | >128 | >128 | >128 | ND | >128 | >128 | >128 | ND |
| ES181079 | >128 | ND | >128 | ND | >128 | ND | >128 | ND | >128 | ND |
| ES175081 | >128 | ND | >128 | ND | >128 | ND | >128 | ND | >128 | ND |
| EL-50(b) | >128 | ND | >128 | ND | >128 | ND | >128 | ND | >128 | ND |
| MAB-01-82A | >128 | ND | >128 | ND | >128 | ND | >128 | ND | >128 | ND |
| MAB-01-140A | >128 | ND | >128 | ND | >128 | ND | >128 | ND | >128 | ND |
| MAB-01-250A | >128 | ND | >128 | ND | >128 | ND | >128 | ND | >128 | ND |
| ES181085 | >128 | ND | >128 | ND | >128 | ND | >128 | ND | >128 | ND |
| PN21 | >128 | ND | >128 | ND | >128 | ND | >128 | ND | >128 | ND |
| PN19 | >128 | ND | >128 | ND | >128 | ND | >128 | ND | >128 | ND |
| MAB-02-59A | >128 | ND | >128 | ND | >128 | ND | >128 | ND | >128 | ND |
| PN20 | >128 | ND | >128 | ND | >128 | ND | >128 | ND | >128 | ND |
| MAB-02-148A | >128 | ND | >128 | ND | >128 | ND | >128 | ND | >128 | ND |
| POD-93-05 PN30 | >128 | ND | >128 | >128 | >128 | ND | >128 | >128 | >128 | ND |
| TY3-317 | >128 | ND | 32 | ND | >128 | ND | >128 | ND | >128 | ND |
| TY3-326 | | | | | >500 | | >500 | | >500 | |
| TY3-397 | >500 | >500 | >500 | >500 | >500 | >500 | >500 | >500 | >500 | >500 |
| TY3-479 | >128 | ND | >128 | ND | >128 | ND | >128 | ND | >128 | ND |
| SAT-187-096 | >128 | | >128 | | >128 | | >128 | | >128 | ND |
| SAT-207-008 | >128 | | >128 | | >128 | | >128 | | >128 | ND |
| TY3-437 | >128 | | 32 | | >128 | | >128 | | >128 | ND |
| TY3-440 | >128 | | 64 | | >128 | | >128 | | >128 | ND |
| TY3-478 | >128 | | 32 | | >128 | | >128 | | >128 | ND |
| TY3-484 | >128 | | 64 | | >128 | | >128 | | >128 | ND |
| EL-119(a) | >128 | | >128 | | >128 | | >128 | | >128 | ND |
| EL-131(a) | >128 | | >128 | | >128 | | >128 | | >128 | ND |
| EL-140(b) | >128 | | >128 | | >128 | | >128 | | >128 | ND |
| EL-92(b) | >128 | | >128 | | >128 | | >128 | | >128 | ND |
| MAB-01-230A | >128 | | >128 | | >128 | | >128 | | >128 | ND |

Fig. 2 (Cont.)

| | | | | | | | | | |
|---|---|---|---|---|---|---|---|---|---|
| MAB-01-252A | >128 | | >128 | | >128 | | >128 | | >128 | ND |
| SAT-187-065 | >128 | | >128 | | >128 | | >128 | | >128 | ND |
| SAT-187-085 | >128 | | >128 | | >128 | | >128 | | >128 | ND |
| DR-01-099 | >128 | ND | >128 | ND | >128 | ND | >128 | ND | >128 | ND |
| DR-01-286 | >128 | ND | >128 | ND | >128 | ND | >128 | ND | >128 | ND |
| DR-02-017 | >128 | ND | >128 | ND | >128 | ND | >128 | ND | >128 | ND |
| DR-02-049 | >128 | >128 | >128 | >128 | >128 | >128 | >128 | >128 | >128 | >128 |
| ES215084 | >128 | >128 | >128 | >128 | >128 | >128 | >128 | >128 | >128 | >128 |
| ES215087 | >128 | >128 | >128 | >128 | >128 | >128 | >128 | >128 | >128 | >128 |
| DR-01-30 | >128 | ND | >128 | ND | >128 | ND | >128 | ND | >128 | ND |
| EL-115(b) | >128 | | >128 | | >128 | | >128 | | >128 | ND |
| TY3-444 | >500 | >500 | >500 | >500 | >500 | >500 | >500 | >500 | >500 | |
| POD-71-34 | >128 | | >128 | | >128 | | >128 | | >128 | ND |
| TY3-454 | >500 | >500 | >500 | >500 | >500 | >500 | >500 | >500 | >500 | |
| ES232040 | >128 | >128 | >128 | >128 | >128 | >128 | >128 | >128 | >128 | >128 |
| ES232026 | 128 | 128 | 128 | 128 | 128 | 128 | 128 | 128 | 128 | 128 |
| SAT-187-059 | >128 | | >128 | | >128 | | >128 | | >128 | ND |
| SAT-187-058 | >128 | | >128 | | >128 | | >128 | | >128 | ND |
| POD-125-62 | | | | | >500 | | >500 | | >500 | |
| TY3-271 | | | | | >500 | | >500 | | >500 | |
| TY3-294 | | | | | >500 | | >500 | | >500 | |
| TY3-473B | >128 | | >128 | | >128 | | >128 | | >128 | ND |
| TY3-295 | | | | | >500 | | >500 | | >500 | |
| EL-97(b) | >128 | | >128 | | >128 | | >128 | | >128 | ND |
| SAT-207-031 | >128 | | >128 | | >128 | | >128 | | >128 | ND |
| DR-03-296 | >128 | N/D | >128 | N/D | >128 | N/D | >128 | N/D | >128 | N/D |
| EL-156(b) | >128 | | >128 | | >128 | | >128 | | >128 | ND |
| EL-130(a) | >128 | | >128 | | >128 | | >128 | | >128 | ND |
| EL-106(b) | >128 | | >128 | | >128 | | >128 | | >128 | ND |
| EL-76(a) | >128 | | >128 | | >128 | | >128 | | >128 | ND |
| EL-84(a) | >128 | | >128 | | >128 | | >128 | | >128 | ND |

*Fig. 2 (Cont.)*

| | | | | | | | | | | |
|---|---|---|---|---|---|---|---|---|---|---|
| EL-78(a) | >128 | | >128 | | >128 | | >128 | | >128 | ND |
| EL-91(b) | >128 | | >128 | | >128 | | >128 | | >128 | ND |
| EL-79(c) | >128 | | >128 | | >128 | | >128 | | >128 | ND |
| EL-82(a) | >128 | | >128 | | >128 | | >128 | | >128 | ND |
| EL-155c | >128 | | >128 | | >128 | | >128 | | >128 | ND |
| EL-107(b) | >128 | | >128 | | >128 | | >128 | | >128 | ND |
| EL-74(c) | >128 | | >128 | | >128 | | >128 | | >128 | ND |
| EL-83(a) | >128 | | >128 | | >128 | | >128 | | >128 | ND |
| EL-102(a) | >128 | | >128 | | >128 | | >128 | | >128 | ND |
| ES232075 | >128 | >128 | >128 | ND | >128 | ND | >128 | ND | >128 | ND |
| ES232080 | >128 | >128 | >128 | ND | >128 | ND | >128 | ND | >128 | ND |
| MAB-03-65 | >128 | >128 | >128 | ND | >128 | ND | >128 | ND | >128 | ND |
| ES232090 | >128 | >128 | >128 | ND | >128 | ND | >128 | ND | >128 | ND |
| ES243026 | >128 | N/D | >128 | N/D | >128 | N/D | >128 | N/D | >128 | N/D |
| ES243030 | >128 | N/D | >128 | N/D | >128 | N/D | >128 | N/D | >128 | N/D |
| ES243025 | >128 | N/D | >128 | N/D | >128 | N/D | >128 | N/D | >128 | N/D |
| ES243056 | >128 | >128 | >128 | >128 | >128 | >128 | >128 | >128 | >128 | >128 |
| ES243059 | >128 | >128 | >128 | >128 | >128 | >128 | >128 | >128 | >128 | >128 |
| MAB-03-61 | >128 | >128 | >128 | ND | >128 | ND | >128 | ND | >128 | ND |
| MAB-03-55 | >128 | >128 | >128 | ND | >128 | ND | >128 | ND | >128 | ND |
| DR-03-253 | >128 | ND | >128 | ND | >128 | ND | >128 | ND | >128 | ND |
| DR-03-284 | >128 | N/D | >128 | N/D | >128 | N/D | >128 | N/D | >128 | N/D |
| ES181093 | >128 | | >128 | | >128 | | >128 | | >128 | ND |
| ES202003 | >128 | | >128 | | >128 | | >128 | | >128 | ND |
| ES202044 | >128 | | >128 | | >128 | | >128 | | >128 | ND |
| ES215042 | >128 | ND | >128 | ND | >128 | ND | >128 | ND | >128 | ND |
| DR-04-107 | >128 | >128 | >128 | >128 | >128 | >128 | >128 | >128 | >128 | >128 |
| DR-01-163 | >128 | ND | >128 | ND | >128 | ND | >128 | ND | >128 | ND |
| MAB-02-106A | >128 | ND | >128 | ND | >128 | ND | >128 | ND | >128 | ND |
| MAB-02-108A | >128 | ND | >128 | ND | >128 | ND | >128 | ND | >128 | ND |
| MIK-B-2 | | | | | | | | | ≥1200 | |

Fig. 2 (Cont.)

| | | | | | | | | | | |
|---|---|---|---|---|---|---|---|---|---|---|
| POD-41-34 | | | | | | | | | ≥1000 | |
| POD-41-63 | | | | | | | | | ≥1000 | |
| POD-41-73 | | | | | | | | | ≥1000 | |
| DR-01-012 | >128 | ND | >128 | ND | >128 | ND | >128 | ND | >128 | ND |
| POD-41-43 | | | | | | | | | ≥1000 | |
| POD-125-81 | >128 | | >128 | | >128 | | >128 | | >128 | ND |
| EL-194B | >128 | ND | >128 | ND | >128 | ND | >128 | ND | >128 | ND |
| MAB-03-172 | | | | | | | | | | |
| POD-41-78 | >128 | | >128 | | >128 | | >128 | | >128 | ND |
| ES232055 | >128 | >128 | >128 | >128 | >128 | >128 | >128 | >128 | >128 | >128 |
| MAB-02-217 | >128 | N/D | >128 | N/D | >128 | N/D | >128 | N/D | >128 | N/D |
| MAB-02-243 | >128 | >128 | >128 | >128 | >128 | >128 | >128 | >128 | >128 | >128 |
| MAB-02-263 | >128 | >128 | >128 | >128 | >128 | >128 | >128 | >128 | >128 | >128 |
| DR-01-196 | >128 | ND | >128 | ND | >128 | ND | >128 | ND | >128 | ND |
| MAB-02-67A | >128 | ND | >128 | ND | >128 | ND | >128 | ND | >128 | ND |
| MAB-02-82A | >128 | ND | >128 | ND | >128 | ND | >128 | ND | >128 | ND |
| DR-01-057 | >128 | ND | >128 | ND | >128 | ND | >128 | ND | >128 | ND |
| POD-125-88 | >128 | | >128 | | >128 | | >128 | | >128 | |
| POD-125-89 | >128 | | >128 | | >128 | | >128 | | >128 | ND |
| SAT-169-089 | >128 | | >128 | | >128 | | >128 | | >128 | ND |
| SAT-169-090 | >128 | | >128 | | >128 | | >128 | | >128 | ND |
| ES202008 | >128 | | >128 | | >128 | | >128 | | >128 | ND |
| ES202020 | >128 | | >128 | | >128 | | >128 | | >128 | ND |
| MAB-02-98A | >128 | ND | 128 | ND | >128 | ND | >128 | ND | >128 | ND |
| MAB-02-92A | 128 | ND | 64 | ND | 128 | ND | 64 | ND | 64 | ND |
| DR-01-067 | >128 | ND | >128 | ND | >128 | ND | >128 | ND | >128 | ND |
| DR-01-132 | >128 | ND | >128 | ND | >128 | ND | >128 | ND | >128 | ND |
| ES202053A | >128 | ND | >128 | >128 | >128 | ND | >128 | >128 | >128 | ND |
| ES202053B | >128 | ND | >128 | >128 | >128 | ND | >128 | >128 | >128 | ND |
| ES215039 | >128 | ND | >128 | ND | >128 | ND | >128 | ND | >128 | ND |
| ES215031 | >128 | ND | >128 | ND | >128 | ND | >128 | ND | >128 | ND |

Fig. 2 (Cont.)

| | | | | | | | | | | |
|---|---|---|---|---|---|---|---|---|---|---|
| ES243086 (same as ES215031) | >128 | n/d | >128 | n/d | >128 | n/d | >128 | n/d | >128 | n/d |
| ES243091 | >128 | n/d | >128 | n/d | >128 | n/d | >128 | n/d | >128 | n/d |
| ES243090 | >128 | n/d | >128 | n/d | >128 | n/d | >128 | n/d | >128 | n/d |
| ES243094 | >128 | n/d | >128 | n/d | >128 | n/d | >128 | n/d | >128 | n/d |
| ES202088 | >128 | ND | >128 | ND | >128 | ND | >128 | ND | >128 | ND |
| DR-01-140 | >128 | ND | >128 | ND | >128 | ND | >128 | ND | >128 | ND |
| DR-01-143 | >128 | ND | >128 | ND | >128 | ND | >128 | ND | >128 | ND |
| DR-01-269 | >128 | ND | >128 | ND | >128 | ND | >128 | ND | >128 | ND |
| DR-02-051 | >128 | N/D | >128 | N/D | >128 | N/D | >128 | N/D | >128 | N/D |
| DR-01-125 | >128 | ND | >128 | ND | >128 | ND | >128 | ND | >128 | ND |
| DR-01-127 | >128 | ND | >128 | ND | >128 | ND | >128 | ND | >128 | ND |
| DR-01-114 | >128 | ND | >128 | ND | >128 | ND | >128 | ND | >128 | ND |
| DR-01-173 | >128 | ND | >128 | ND | >128 | ND | >128 | ND | >128 | ND |
| DR-01-203 | >128 | ND | >128 | ND | >128 | ND | >128 | ND | >128 | ND |
| DR-01-198 | >128 | ND | >128 | ND | >128 | ND | >128 | ND | >128 | ND |
| DR-03-130 | >128 | >128 | >128 | >128 | >128 | >128 | >128 | >128 | >128 | >128 |
| ES243051 | >128 | >128 | >128 | >128 | >128 | >128 | >128 | >128 | >128 | >128 |
| ES243061 | >128 | >128 | >128 | >128 | >128 | >128 | >128 | >128 | >128 | >128 |
| ES243075 | >128 | n/d | >128 | n/d | >128 | n/d | >128 | n/d | >128 | n/d |
| DR-01-011-2 | >128 | ND | >128 | ND | >128 | ND | >128 | ND | >128 | ND |
| L234-1227 | >128 | N/D | >128 | N/D | >128 | N/D | >128 | N/D | >128 | N/D |
| L234-1058 | >128 | N/D | >128 | N/D | >128 | N/D | >128 | N/D | >128 | N/D |
| DR-01-025 | >128 | ND | >128 | ND | >128 | ND | >128 | ND | >128 | ND |
| DR-03-085 | >128 | >128 | >128 | ND | >128 | ND | >128 | ND | >128 | ND |
| DR-02-075 | >128 | N/D | >128 | N/D | >128 | N/D | >128 | N/D | >128 | N/D |
| DR-01-267 | >128 | >128 | >128 | >128 | >128 | >128 | >128 | >128 | >128 | >128 |
| DR-01-291 | >128 | ND | >128 | ND | >128 | ND | >128 | ND | >128 | ND |
| DR-02-286 | >128 | >128 | >128 | >128 | >128 | >128 | >128 | >128 | >128 | >128 |
| DR-03-019 | 128 | 128 | 128 | 128 | 128 | 128 | 128 | 128 | 128 | 128 |
| DR-03-029 | 128 | 128 | 128 | 128 | 128 | 128 | 128 | 128 | 128 | 128 |
| DR-02-93 | 128 | 128 | 128 | 128 | 128 | 128 | 128 | 128 | 128 | 128 |

Fig. 2 (Cont.)

| | | | | | | | | | | |
|---|---|---|---|---|---|---|---|---|---|---|
| DR-03-002 | 128 | 128 | 128 | 128 | 128 | 128 | 128 | 128 | 128 | 128 |
| DR-03-013 | 128 | 128 | 128 | 128 | 128 | 128 | 128 | 128 | 128 | 128 |
| DR-03-073 | >128 | >128 | >128 | >128 | >128 | >128 | >128 | >128 | >128 | >128 |
| DR-03-153 | >128 | >128 | >128 | >128 | >128 | >128 | >128 | >128 | >128 | >128 |
| DR-03-149 | >128 | >128 | >128 | >128 | >128 | >128 | >128 | >128 | >128 | >128 |
| DR-03-117 | >128 | >128 | >128 | >128 | >128 | >128 | >128 | >128 | >128 | >128 |
| DR-03-261 | >128 | N/D | >128 | N/D | >128 | N/D | >128 | N/D | >128 | N/D |
| DR-03-262 | >128 | N/D | >128 | N/D | >128 | N/D | >128 | N/D | >128 | N/D |
| DR-03-195 | >128 | ND | >128 | ND | >128 | ND | >128 | ND | >128 | ND |
| DR-03-160 | >128 | >128 | >128 | >128 | >128 | >128 | >128 | >128 | >128 | >128 |
| DR-03-259 | >128 | N/D | >128 | N/D | >128 | N/D | >128 | N/D | >128 | N/D |
| DR-03-164 | >128 | >128 | >128 | >128 | >128 | >128 | >128 | >128 | >128 | >128 |
| DR-04-008 | >128 | >128 | >128 | >128 | >128 | >128 | >128 | >128 | >128 | >128 |
| DR-02-070 | >128 | N/D | >128 | N/D | >128 | N/D | >128 | N/D | >128 | N/D |
| DR-03-121 | >128 | >128 | >128 | >128 | >128 | >128 | >128 | >128 | >128 | >128 |
| ES232062 | >128 | >128 | >128 | >128 | >128 | >128 | >128 | >128 | >128 | >128 |
| ES232068 | >128 | >128 | >128 | ND | >128 | ND | >128 | ND | >128 | ND |
| DR-03-174 | >128 | >128 | >128 | ND | >128 | ND | >128 | ND | >128 | ND |
| DR-03-190 | >128 | ND | >128 | ND | >128 | ND | >128 | ND | >128 | ND |
| DR-03-192 | >128 | ND | >128 | ND | >128 | ND | >128 | ND | >128 | ND |
| MAB-03-44 | >128 | ND | >128 | ND | >128 | ND | >128 | ND | >128 | ND |
| ES232067 | >128 | >128 | >128 | >128 | >128 | >128 | >128 | >128 | >128 | >128 |
| ES243001 | >128 | >128 | >128 | >128 | >128 | >128 | >128 | >128 | >128 | >128 |
| MAB-03-34 | >128 | >128 | >128 | ND | >128 | ND | >128 | ND | >128 | ND |
| MAB-03-36 | >128 | >128 | >128 | >128 | >128 | >128 | >128 | >128 | >128 | >128 |
| ES232083 | >128 | ND | >128 | ND | >128 | ND | >128 | ND | >128 | ND |
| ES232089 | >128 | ND | >128 | ND | >128 | ND | >128 | ND | >128 | ND |
| ES243053 | >128 | >128 | >128 | >128 | >128 | >128 | >128 | >128 | >128 | >128 |
| ES243055 | >128 | >128 | >128 | >128 | >128 | >128 | >128 | >128 | >128 | >128 |
| ES243065 | >128 | >128 | >128 | >128 | >128 | >128 | >128 | >128 | >128 | >128 |
| ES243093 | >128 | n/d | >128 | n/d | >128 | n/d | >128 | n/d | >128 | n/d |

Fig. 2 (Cont.)

| | | | | | | | | | | |
|---|---|---|---|---|---|---|---|---|---|---|
| DR-02-120 | >128 | N/D | >128 | N/D | >128 | N/D | >128 | N/D | >128 | N/D |
| DR-01-089 | >128 | N/D | >128 | N/D | >128 | N/D | >128 | N/D | >128 | N/D |
| DR-02-273 | >128 | >128 | >128 | >128 | >128 | >128 | >128 | >128 | >128 | >128 |
| DR-02-128 | >128 | N/D | >128 | N/D | >128 | N/D | >128 | N/D | >128 | N/D |
| DR-02-124 | >128 | N/D | >128 | N/D | >128 | N/D | >128 | N/D | >128 | N/D |
| DR-04-036 | >128 | N/D | >128 | N/D | >128 | N/D | >128 | N/D | >128 | N/D |
| DR-01-283 | >128 | ND | >128 | ND | >128 | ND | >128 | ND | >128 | ND |
| DR-01-288 | >128 | ND | >128 | ND | >128 | ND | >128 | ND | >128 | ND |
| DR-01-040 | >128 | ND | >128 | ND | >128 | ND | >128 | ND | >128 | ND |
| DR-01-122 | >128 | ND | >128 | ND | >128 | ND | >128 | ND | >128 | ND |
| DR-02-263 | >128 | >128 | >128 | >128 | >128 | >128 | >128 | >128 | >128 | >128 |
| DR-02-258 | >128 | >128 | >128 | >128 | >128 | >128 | >128 | >128 | >128 | >128 |
| DR-02-110 | >128 | N/D | >128 | N/D | >128 | N/D | >128 | N/D | >128 | N/D |
| DR-02-264 | >128 | >128 | >128 | >128 | >128 | >128 | >128 | >128 | >128 | >128 |
| DR-02-244 | >128 | >128 | >128 | >128 | >128 | >128 | >128 | >128 | >128 | >128 |
| DR-02-268 | >128 | >128 | >128 | >128 | >128 | >128 | >128 | >128 | >128 | >128 |
| DR-02-184 | >128 | >128 | >128 | >128 | >128 | >128 | >128 | >128 | >128 | >128 |
| DR-02-189 | >128 | >128 | >128 | >128 | >128 | >128 | >128 | >128 | >128 | >128 |
| DR-02-071 | >128 | N/D | >128 | N/D | >128 | N/D | >128 | N/D | >128 | N/D |
| DR-02-230 | >128 | >128 | >128 | >128 | >128 | >128 | >128 | >128 | >128 | >128 |
| DR-02-231 | >128 | >128 | >128 | >128 | >128 | >128 | >128 | >128 | >128 | >128 |
| DR-02-233 | >128 | >128 | >128 | >128 | >128 | >128 | >128 | >128 | >128 | >128 |
| DR-01-222 | >128 | ND | >128 | ND | >128 | ND | >128 | ND | >128 | ND |
| DR-01-237 | >128 | ND | >128 | ND | >128 | ND | >128 | ND | >128 | ND |
| DR-01-259 | >128 | ND | >128 | ND | >128 | ND | >128 | ND | >128 | ND |
| DR-01-280 | >128 | ND | >128 | ND | >128 | ND | >128 | ND | >128 | ND |
| DR-02-097 | >128 | >128 | >128 | >128 | >128 | >128 | >128 | >128 | >128 | >128 |
| DR-01-177 | >128 | ND | >128 | ND | >128 | ND | >128 | ND | >128 | ND |
| DR-01-248 | >128 | ND | >128 | ND | >128 | ND | >128 | ND | >128 | ND |
| DR-01-035 | >128 | ND | >128 | ND | >128 | ND | >128 | ND | >128 | ND |
| DR-02-261 | >128 | >128 | >128 | >128 | >128 | >128 | >128 | >128 | >128 | >128 |

Fig. 2 (Cont.)

| | | | | | | | | | | |
|---|---|---|---|---|---|---|---|---|---|---|
| DR-03-033 | 128 | 128 | 128 | 128 | 128 | 128 | 128 | 128 | 128 | 128 |
| DR-01-102 | >128 | ND | >128 | ND | >128 | ND | >128 | ND | >128 | ND |
| DR-03-006 | 128 | 128 | 128 | 128 | 128 | 128 | 128 | 128 | 128 | 128 |
| DR-01-218 | >128 | ND | >128 | ND | >128 | ND | >128 | ND | >128 | ND |
| DR-02-020 | >128 | ND | >128 | ND | >128 | ND | >128 | ND | >128 | ND |
| DR-01-263 | >128 | ND | >128 | ND | >128 | ND | >128 | ND | >128 | ND |
| DR-01-230 | >128 | ND | >128 | ND | >128 | ND | >128 | ND | >128 | ND |
| DR-01-236 | >128 | ND | >128 | ND | >128 | ND | >128 | ND | >128 | ND |
| DR-01-271 | >128 | ND | >128 | ND | >128 | ND | >128 | ND | >128 | ND |
| DR-02-059 | >128 | N/D | >128 | N/D | >128 | N/D | >128 | N/D | >128 | N/D |
| DR-03-110 | >128 | >128 | >128 | ND | >128 | ND | >128 | ND | >128 | ND |
| DR-01-169 | >128 | ND | >128 | ND | >128 | ND | >128 | ND | >128 | ND |
| DR-02-170 | >128 | >128 | >128 | >128 | >128 | >128 | >128 | >128 | >128 | >128 |
| DR-04-122 | >128 | n/d | >128 | n/d | >128 | n/d | >128 | n/d | >128 | n/d |
| DR-04-142 | >128 | n/d | >128 | n/d | >128 | n/d | >128 | n/d | >128 | n/d |
| DR-02-158 | >128 | >128 | >128 | >128 | >128 | >128 | >128 | >128 | >128 | >128 |
| DR-02-160 | >128 | >128 | >128 | >128 | >128 | >128 | >128 | >128 | >128 | >128 |
| DR-04-118 | >128 | n/d | >128 | n/d | >128 | n/d | >128 | n/d | >128 | n/d |
| DR-04-136 | >128 | n/d | >128 | n/d | >128 | n/d | >128 | n/d | >128 | n/d |
| DR-02-126 | >128 | N/D | >128 | N/D | >128 | N/D | >128 | N/D | >128 | N/D |
| DR-02-165 | >128 | >128 | >128 | >128 | >128 | >128 | >128 | >128 | >128 | >128 |
| DR-02-099 | >128 | >128 | >128 | >128 | >128 | >128 | >128 | >128 | >128 | >128 |
| DR-01-95 | >128 | N/D | >128 | N/D | >128 | N/D | >128 | N/D | >128 | N/D |
| ES215046 | >128 | ND | >128 | ND | >128 | ND | >128 | ND | >128 | ND |
| ES202021 | >128 | ND | >128 | ND | >128 | ND | >128 | ND | >128 | ND |
| L234-003 | >128 | ND | >128 | ND | >128 | ND | >128 | ND | >128 | ND |
| L234-0301 | >128 | ND | >128 | ND | >128 | ND | >128 | ND | >128 | ND |
| L234-1065 | >128 | N/D | >128 | N/D | >128 | N/D | >128 | N/D | >128 | N/D |
| L234-1023 | >128 | ND | >128 | ND | >128 | ND | >128 | ND | >128 | ND |
| L234-1192 | >128 | N/D | >128 | N/D | >128 | N/D | >128 | N/D | >128 | N/D |
| ES202038 | >128 | ND | 32 | >128 | >128 | ND | 64 | >128 | 32 | ND |

*Fig. 2 (Cont.)*

| | | | | | | | | | | |
|---|---|---|---|---|---|---|---|---|---|---|
| ES202023 | >128 | | 64 | | >128 | | >128 | | >128 | ND |
| ES202052 | >128 | ND | 64 | >128 | >128 | ND | 128 | >128 | 64 | ND |
| ES202047 | >128 | | >128 | | >128 | | >128 | | >128 | ND |
| DR-03-138 | >128 | >128 | >128 | >128 | >128 | >128 | >128 | >128 | >128 | >128 |
| DR-03-145 | >128 | >128 | >128 | >128 | >128 | >128 | >128 | >128 | >128 | >128 |
| ES243067 | >128 | >128 | >128 | >128 | >128 | >128 | >128 | >128 | >128 | >128 |
| ES243070 | >128 | >128 | >128 | >128 | >128 | >128 | >128 | >128 | >128 | >128 |
| TY3-510 | >256 | | >256 | | >256 | | >256 | | >256 | |
| TY3-513 | >256 | | 128 | | >256 | | >256 | | 256 | |
| POD-41-76 | | | | | | | | | ≥1000 | |
| POD-125-80 | >256 | | >256 | | >256 | | >256 | | >256 | |
| DR-01-191 | >128 | ND | >128 | ND | >128 | ND | >128 | ND | >128 | ND |
| DR-01-043 | >128 | ND | >128 | ND | >128 | ND | >128 | ND | >128 | ND |
| POD-125-84 | >128 | | >128 | | >128 | | >128 | | >128 | |
| POD-125-85 | >256 | | >256 | | >256 | | >256 | | >256 | |
| SAT-169-085 | >128 | | >128 | | >128 | | >128 | | >128 | |
| SAT-169-088 | >128 | | >128 | | >128 | | >128 | | >128 | |
| DR-01-246 | >128 | N/D | >128 | N/D | >128 | N/D | >128 | N/D | >128 | N/D |
| EL-207 | >128 | ND | >128 | ND | >128 | ND | >128 | ND | >128 | ND |
| EL-208 | >128 | ND | >128 | ND | >128 | ND | >128 | ND | >128 | ND |
| DR-01-112 | >128 | ND | >128 | ND | >128 | ND | >128 | ND | >128 | ND |
| EL-210 | >128 | ND | >128 | ND | >128 | ND | >128 | ND | >128 | ND |
| DR-01-013 | >128 | ND | >128 | ND | >128 | ND | >128 | ND | >128 | ND |
| DR-01-018 | >128 | ND | >128 | ND | >128 | ND | >128 | ND | >128 | ND |
| DR-01-020 | >128 | ND | >128 | ND | >128 | ND | >128 | ND | >128 | ND |
| DR-01-029 | >128 | ND | >128 | ND | >128 | ND | >128 | ND | >128 | ND |
| POD-41-91 | | | | | | | | | ≥1000 | |
| ES170034 | >256 | | >256 | | >256 | | >256 | | >256 | |
| ES175059 | >128 | | >128 | | >128 | | >128 | | >128 | |
| MAB-01-73A | >128 | | >128 | | >128 | | >128 | | >128 | |
| MAB-01-90A | >128 | | >128 | | >128 | | >128 | | >128 | |

Fig. 2 (Cont.)

| | | | | | | | | | | |
|---|---|---|---|---|---|---|---|---|---|---|
| DR-02-297 | 128 | 128 | 128 | 128 | 128 | 128 | 128 | 128 | 128 | 128 |
| MAB-01-135A | >128 | | >128 | | >128 | | >128 | | >128 | ND |
| EL-64(e) | >128 | | >128 | | >128 | | >128 | | >128 | ND |
| EL-75(a) | >128 | | >128 | | >128 | | >128 | | >128 | ND |
| EL-70(c) | >128 | | >128 | | >128 | | >128 | | >128 | ND |
| EL-48(a) | >128 | | >128 | | >128 | | >128 | | >128 | |
| DR-01-085 | >128 | ND | >128 | ND | >128 | ND | >128 | ND | >128 | ND |
| DR-01-279 | >128 | N/D | >128 | N/D | >128 | N/D | >128 | N/D | >128 | N/D |
| DR-01-156 | >128 | ND | >128 | ND | >128 | ND | >128 | ND | >128 | ND |
| DR-01-190 | >128 | ND | >128 | ND | >128 | ND | >128 | ND | >128 | ND |
| DR-01-121 | >128 | ND | >128 | ND | >128 | ND | >128 | ND | >128 | ND |
| DR-02-081 | >128 | >128 | >128 | >128 | >128 | >128 | >128 | >128 | >128 | >128 |
| DR-02-038 | >128 | >128 | >128 | >128 | >128 | >128 | >128 | >128 | >128 | >128 |
| DR-01-256 | >128 | N/D | >128 | N/D | >128 | N/D | >128 | N/D | >128 | N/D |
| DR-03-239 | >128 | ND | >128 | ND | >128 | ND | >128 | ND | >128 | ND |
| DR-04-105 | >128 | n/d | >128 | n/d | >128 | n/d | >128 | n/d | >128 | n/d |
| DR-01-275 | >128 | N/D | >128 | N/D | >128 | N/D | >128 | N/D | >128 | N/D |
| DR-02-040 | >128 | >128 | >128 | >128 | >128 | >128 | >128 | >128 | >128 | >128 |
| DR-03-210 | >128 | ND | >128 | ND | >128 | ND | >128 | ND | >128 | ND |
| DR-03-226 | >128 | N/D | >128 | N/D | >128 | N/D | >128 | N/D | >128 | N/D |
| DR-03-274 | >128 | N/D | >128 | N/D | >128 | N/D | >128 | N/D | >128 | N/D |
| DR-03-279 | >128 | N/D | >128 | N/D | >128 | N/D | >128 | N/D | >128 | N/D |
| DR-03-292 | >128 | N/D | >128 | N/D | >128 | N/D | >128 | N/D | >128 | N/D |
| DR-03-237 | >128 | ND | >128 | ND | >128 | ND | >128 | ND | >128 | ND |
| DR-03-242 | >128 | ND | >128 | ND | >128 | ND | >128 | ND | >128 | ND |
| DR-01-023 | >128 | ND | >128 | ND | >128 | ND | >128 | ND | >128 | ND |
| DR-01-193 | >128 | ND | >128 | ND | >128 | ND | >128 | ND | >128 | ND |
| MAB-02-145A | >128 | ND | >128 | ND | >128 | ND | >128 | ND | >128 | ND |
| DR-01-167 | >128 | ND | >128 | ND | >128 | ND | >128 | ND | >128 | ND |
| MAB-02-152A | >128 | ND | >128 | ND | >128 | ND | >128 | ND | >128 | ND |
| DR-01-158 | >128 | ND | >128 | ND | >128 | ND | >128 | ND | >128 | ND |

Fig. 2 (Cont.)

| | | | | | | | | | | |
|---|---|---|---|---|---|---|---|---|---|---|
| DR-03-244 | >128 | ND | >128 | ND | >128 | ND | >128 | ND | >128 | ND |
| DR-01-148 | >128 | ND | >128 | ND | >128 | ND | >128 | ND | >128 | ND |
| DR-02-007 | >128 | N/D | >128 | N/D | >128 | N/D | >128 | N/D | >128 | N/D |
| DR-01-224 | >128 | N/D | >128 | N/D | >128 | N/D | >128 | N/D | >128 | N/D |
| ES181091 | >128 | | >128 | | >128 | | >128 | | >128 | ND |
| ES181090 | >128 | | >128 | | >128 | | >128 | | >128 | ND |
| ES181068 | >128 | | >128 | | >128 | | >128 | | *** | |
| ES181077 | >128 | | >128 | | >128 | | >128 | | >128 | |
| POD-125-96 | >64 | | >64 | | >64 | | >64 | | >8 | |
| ES175028 | | | | | | | | | >256 | |
| ES175045 | >256 | 6 | >256 | | >256 | | >256 | | >25 | |
| ES175091 | >128 | 8 | >128 | | >128 | | >128 | | >12 | |
| POD-125-78 | >128 | | >128 | | >128 | | >128 | | >128 | ND |
| ES181096 | >128 | | >128 | | >128 | | >128 | | >128 | ND |
| POD-41-20 | | | | | | | | | ≥1200 | |
| MAB-01-156A | >128 | | >128 | | >128 | | >128 | | >128 | ND |
| POD-41-05 | | | | | | | | | ≥1200 | |
| POD-41-08 | | | | | | | | | ≥1200 | |
| POD-41-44 | | | | | | | | | ≥1000 | |
| DISI-004 | >128 | | >128 | | >128 | | >128 | | >128 | |
| SAT-187-015 | >128 | | >128 | | >128 | | >128 | | >128 | ND |
| SAT-187-018 | >128 | | >128 | | >128 | | >128 | | >128 | |
| SAT-187-010 | >128 | | >128 | | >128 | | >128 | | >128 | |
| MAB-03-244 | >128 | >128 | >128 | >128 | >128 | >128 | >128 | >128 | >128 | >128 |
| EL219B | >128 | ND | >128 | ND | >128 | ND | >128 | ND | >128 | ND |
| SAT-187-005 | >128 | | >128 | | >128 | | >128 | | 64 | |
| SAT-187-009 | >128 | | >128 | | >128 | | >128 | | >128 | |
| DISI-002 | >128 | | >128 | | >128 | | >128 | | >128 | |
| DISI-012 | >128 | | >128 | | >128 | | >128 | | >128 | |
| DISI-015 | >128 | | >128 | | >128 | | >128 | | >128 | |
| ES181007 | >128 | | >128 | | >128 | | >128 | | >128 | |

*Fig. 2 (Cont.)*

| | | | | | | | | | |
|---|---|---|---|---|---|---|---|---|---|
| ES1810011 | >128 | | >128 | | >128 | | >128 | | >128 | |
| SAT-187-023 | >128 | | >128 | | >128 | | >128 | | >128 | |
| SAT-187-044 | >128 | | >128 | | >128 | | >128 | | >128 | ND |
| SAT-169-095 | >128 | | >128 | | >128 | | >128 | | >128 | |
| EL-190 | >128 | ND | >128 | ND | >128 | ND | >128 | ND | >128 | ND |
| SAT-187-030 | >128 | | >128 | | >128 | | >128 | | >128 | |
| ES215015 | >128 | ND | >128 | ND | >128 | ND | >128 | ND | >128 | ND |
| SAT-187-037 | >128 | | >128 | | >128 | | >128 | | >128 | |
| ES215008 | >128 | ND | >128 | ND | >128 | ND | >128 | ND | >128 | ND |
| ES215001 | >128 | ND | >128 | ND | >128 | ND | >128 | ND | >128 | ND |
| DISI-005 | >128 | | >128 | | >128 | | >128 | | >128 | |

NON-BETA LACTAM ANTIBIOTICS

RELATED APPLICATIONS

This application is a National Stage filing under 35 U.S.C. § 371 of International Application No. PCT/US2015/052474 filed Sep. 25, 2015, which claims priority under 35 U.S.C. § 119(e) to U.S. Provisional Patent Application No. 62/055,604 filed Sep. 25, 2014, which applications are incorporated herein by reference.

GOVERNMENT SUPPORT

This invention was made with government support under Grant No. AI090818 awarded by the National Institutes of Health. The government has certain rights in the invention.

BACKGROUND OF THE INVENTION

*Staphylococcus aureus* is a leading human bacterial pathogen that is a common source of infections in healthcare and community environments. The 2013 Center for Disease Control (CDC) report on antibiotic resistance prioritized methicillin-resistant *Staphylococcus aureus* (MRSA) as an ongoing serious threat, with 2011 records indicating that 11,285 of the 23,000 deaths caused by antibiotic-resistant bacteria and fungi in the US were directly attributed to MRSA infections. Due to the difficulty in calculating exact mortality rates, these figures are given as conservative estimates and the actual numbers are thought to be higher. The financial cost incurred by hospitals and clinics is even more difficult to measure, but a study from 2009 estimated that a MRSA infection that takes place during surgery could cost a hospital $60,000 per patient in additional procedures and extended hospital stay.

Overall, the number of serious MRSA infection cases in healthcare situations has diminished. However, over the past decade there has been a steady rise in the number of community-associated (CA) infections. If this trend continues and new strains of MRSA show further resistance to existing antibiotics, the CDC intends to upgrade the threat level from serious to urgent. In addition the financial burden imposed by CA-MRSA infection has been estimated at $7,070-$20,489 per patient, at an annual cost of $1.4-$3.8 billion to society. For these reasons the discovery of new classes of antibiotics for treatment of MRSA infections, especially orally available antibiotics, is essential.

Antibiotics that are approved for treatment of MRSA infections are vancomycin (a glycopeptide), linezolid (an oxazolidinone), daptomycin (a lipopeptide) and more recently, ceftaroline (a β-lactam) and tedizolid (an oxazolidinone). Only linezolid and tedizolid are orally bioavailable among these agents. Furthermore, resistance to each of these antibiotics is known. Accordingly, there is a need for new classes of antibiotics, and particularly new classes of antibiotics that are effective against resistant strains of bacteria, including bacteria that are resistant to beta-lactam antibiotics.

SUMMARY

The invention provides the compounds and compositions described herein, as well as methods for treating bacterial infections, and for killing or inhibiting the growth of bacteria using the compounds and compositions. Accordingly, the invention provides a compound of Formula (AI):

$$A\text{-}B\text{-}C\text{-}L\text{-}D \quad (AI)$$

wherein

A is phenyl, benzyl, heteroaryl, or heterocycle, wherein the phenyl, benzyl, heteroaryl, or heterocycle is optionally substituted with one to five $R^A$ groups;

B is 1,2,4-oxadiazole, 1,3,4-oxadiazole, 1,2-oxazole, 1,3-oxazole, triazole, pyrazole, imidazole, or dihydro-imidazole;

C is phenyl or a bicyclic heteroaryl or heterocycle, wherein the phenyl or the bicyclic heteroaryl or heterocycle is optionally substituted with one or five $R^A$ groups;

L is O, S, or NH;

D is phenyl, heteroaryl, heterocycle (e.g., piperidinyl), alkyl, aminoalkyl, hydroxyalkyl, or tert-butyloxycarbonyl, wherein the phenyl is optionally substituted with one to five $R^A$ groups;

or -L-D is absent when C is bicyclic heteroaryl or heterocycle;

each $R^A$ is independently —H, —OH, halo, —N$_3$, —NO$_2$, —O-allyl, —C≡N, —CF$_3$, —OCF$_3$, —C(=O)CF$_3$, alkyl, alkoxy, —NR$^a$R$^b$, or —C≡C—R$^Y$;

$R^a$ and $R^b$ are each independently H, alkyl, or a nitrogen protecting group; and $R^Y$ is H, OH, alkyl, hydroxyalkyl, or a silicon protecting group;

or pharmaceutically acceptable salt or solvate thereof.

When A is heteroaryl, the heteroaryl can be optionally substituted pyrrolyl, pyrazolyl, imidazolyl, triazolyl, pyridyl, indolyl, indazolyl, or pyrrole-pyridine, each of which is optionally substituted with one to five $R^A$ groups. When A is heterocycle, the heterocycle can be optionally substituted pyrrolidinyl, piperidinyl, or pyrimidine-dione.

A compound of Formula (AI) can be a compound of Formula (I):

$$A\text{-}B\text{-}C\text{-}L\text{-}D \quad (I)$$

wherein

A is pyrrolyl, pyrazolyl, imidazolyl, or indolyl, each optionally substituted with one to three $R^X$ groups;

B is 1,2,4-oxadiazole, 1,3,4-oxadiazole, 1,2-oxazole, 1,3-oxazole, triazole, pyrazole, imidazole, or dihydro-imidazole;

C is phenyl, bicyclic heteroaryl, or bicyclic heterocycle, wherein the phenyl or the bicyclic heteroaryl or heterocycle is optionally substituted with one or five $R^X$ groups;

L is O, S, or NH;

D is phenyl, heteroaryl, heterocycle (e.g., piperidinyl), alkyl, aminoalkyl, hydroxyalkyl, or tert-butyloxycarbonyl, wherein the phenyl is optionally substituted with one to five $R^X$ groups;

or -L-D is absent when C is bicyclic heteroaryl or heterocycle;

each $R^X$ is independently —H, —OH, halo, —N$_3$, —NO$_2$, —O-allyl, —C≡N, —CF$_3$, —OCF$_3$, —C(=O)CF$_3$, alkyl, alkoxy, phenyl, phenoxy, benzyl, or cycloalkyl —NR$^a$R$^b$, or —C≡C—R$^Y$;

each $R^a$ and $R^b$ are independently H, alkyl, or a nitrogen protecting group; and $R^Y$ is —H, alkyl, hydroxyalkyl, or a silicon protecting group;

or pharmaceutically acceptable salt or solvate thereof.

One specific value for A is 5-indolyl.
One specific value for B is 1,2,4-oxadiazole.
One specific value for C is phenyl.
One specific value D is optionally substituted phenyl. Other specific values for D include phenyl, 4-CF$_3$-phenyl, or 4-F-phenyl.

A compound of Formula (I) can be a compound of Formula (II):

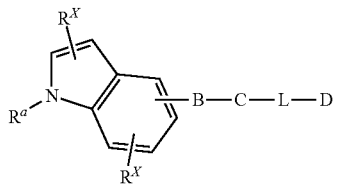

(II)

wherein
B is 1,2,4-oxadiazole, 1,3,4-oxadiazole, 1,2-oxazole, 1,3-oxazole, triazole, pyrazole, imidazole, or dihydro-imidazole;
C is phenyl, bicyclic heteroaryl, or bicyclic heterocycle, wherein the phenyl or the bicyclic heteroaryl or heterocycle is optionally substituted with one or five $R^X$ groups;
L is O, S, or NH;
D is phenyl, heteroaryl, heterocycle (e.g., piperidinyl), alkyl, aminoalkyl, hydroxyalkyl, or tert-butyloxycarbonyl, wherein the phenyl is optionally substituted with one to five $R^X$ groups;
or -L-D is absent when C is bicyclic heteroaryl or heterocycle;
each $R^X$ is independently —H, —OH, halo, —$N_3$, —$NO_2$, —O-allyl, —C≡N, —$CF_3$, —$OCF_3$, —C(=O)$CF_3$, alkyl, alkoxy, phenyl, phenoxy, benzyl, or cycloalkyl —$NR^aR^b$, or —C≡C—$R^Y$;
each $R^a$ and $R^b$ are independently H, alkyl, or a nitrogen protecting group; and
$R^Y$ is —H, alkyl, hydroxyalkyl, or a silicon protecting group;
or pharmaceutically acceptable salt or solvate thereof.

A compound of Formula (I) can also be a compound of Formula (III):

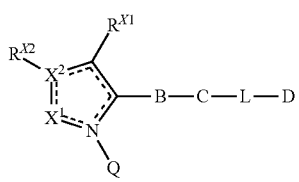

(III)

wherein
$X^1$ is CH or NH; $X^2$ is C or N; and Q is H or absent, such that the dashed lines form two conjugated double bonds and the ring containing $X^1$ and $X^2$ forms a pyrazolyl, imidazolyl, or pyrrolyl ring;
B is 1,2,4-oxadiazole, 1,3,4-oxadiazole, 1,2-oxazole, 1,3-oxazole, triazole, pyrazole, imidazole, or dihydro-imidazole;
C is phenyl, bicyclic heteroaryl, or bicyclic heterocycle, wherein the phenyl or the bicyclic heteroaryl or heterocycle is optionally substituted with one or five $R^X$ groups;
L is O, S, or NH;
D is phenyl, heteroaryl, heterocycle, alkyl, aminoalkyl, hydroxyalkyl, or tert-butyloxycarbonyl, wherein the phenyl is optionally substituted with one to five $R^X$ groups;
or -L-D is absent when C is bicyclic heteroaryl or heterocycle;
each $R^X$, $R^{X1}$, and $R^{X2}$ is independently —H, —OH, halo, —$N_3$, —$NO_2$, —O-allyl, —C≡N, —$CF_3$, —$OCF_3$, —C(=O)$CF_3$, alkyl, alkoxy, phenyl, phenoxy, benzyl, or cycloalkyl —$NR^aR^b$, or —C≡C—$R^Y$;
each $R^a$ and $R^b$ are independently H, alkyl, or a nitrogen protecting group; and
$R^Y$ is —H, alkyl, hydroxyalkyl, or a silicon protecting group;
or pharmaceutically acceptable salt or solvate thereof.

A compound of Formula (I) can also be a compound of Formula (IV):

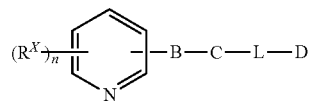

(IV)

wherein
n is 1 or 2;
B is 1,2,4-oxadiazole, 1,3,4-oxadiazole, 1,2-oxazole, 1,3-oxazole, triazole, pyrazole, imidazole, or dihydro-imidazole;
C is phenyl, bicyclic heteroaryl, or bicyclic heterocycle, wherein the phenyl or the bicyclic heteroaryl or heterocycle is optionally substituted with one or five $R^X$ groups;
L is O, S, or NH;
D is phenyl, heteroaryl, heterocycle, alkyl, aminoalkyl, hydroxyalkyl, or tert-butyloxycarbonyl, wherein the phenyl is optionally substituted with one to five $R^X$ groups;
or -L-D is absent when C is bicyclic heteroaryl or heterocycle;
each $R^X$ is independently —H, —OH, halo, —$N_3$, —$NO_2$, —O-allyl, —C≡N, —$CF_3$, —$OCF_3$, —C(=O)$CF_3$, alkyl, alkoxy, phenyl, phenoxy, benzyl, or cycloalkyl —$NR^aR^b$, or —C≡C—$R^Y$;
each $R^a$ and $R^b$ are independently H, alkyl, or a nitrogen protecting group; and
$R^Y$ is —H, alkyl, hydroxyalkyl, or a silicon protecting group;
or pharmaceutically acceptable salt or solvate thereof.

A compound of Formula (I) can also be a compound of Formula (V):

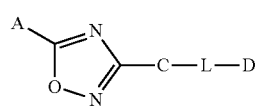

(V)

wherein
A is pyrrolyl, pyrazolyl, imidazolyl, or indolyl, each optionally substituted with one to three $R^X$ groups;
C is phenyl, bicyclic heteroaryl, or bicyclic heterocycle, wherein the phenyl or the bicyclic heteroaryl or heterocycle is optionally substituted with one or five $R^X$ groups;
L is O, S, or NH;
D is phenyl, heteroaryl, heterocycle, alkyl, aminoalkyl, hydroxyalkyl, or tert-butyloxycarbonyl, wherein the phenyl is optionally substituted with one to five $R^X$ groups;
or -L-D is absent when C is bicyclic heteroaryl or heterocycle;
each $R^X$ is independently —H, —OH, halo, —$N_3$, —$NO_2$, —O-allyl, —C≡N, —$CF_3$, —$OCF_3$, —C(=O)$CF_3$, alkyl, alkoxy, phenyl, phenoxy, benzyl, or cycloalkyl —$NR^aR^b$, or —C≡C—$R^Y$;
each $R^a$ and $R^b$ are independently H, alkyl, or a nitrogen protecting group; and $R^Y$ is —H, alkyl, hydroxyalkyl, or a silicon protecting group;
or pharmaceutically acceptable salt or solvate thereof.

A compound of Formula (I) can also be a compound of Formula (VI):

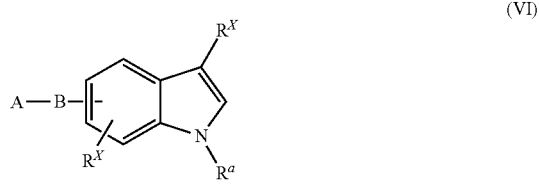

(VI)

wherein

A is pyrrolyl, pyrazolyl, imidazolyl, or indolyl, each optionally substituted with one to three $R^X$ groups;

B is 1,2,4-oxadiazole, 1,3,4-oxadiazole, 1,2-oxazole, 1,3-oxazole, triazole, pyrazole, imidazole, or dihydro-imidazole;

each $R^X$ is independently —H, —OH, halo, —N$_3$, —NO$_2$, —O-allyl, —C≡N, —CF$_3$, —OCF$_3$, —C(=O)CF$_3$, alkyl, alkoxy, phenyl, phenoxy, benzyl, or cycloalkyl —NR$^a$R$^b$, or —C≡C—R$^Y$;

each $R^a$ and $R^b$ are independently H, alkyl, or a nitrogen protecting group; and $R^Y$ is —H, alkyl, hydroxyalkyl, or a silicon protecting group;
or pharmaceutically acceptable salt or solvate thereof.

A compound of Formula (I) can also be a compound of Formula (VII):

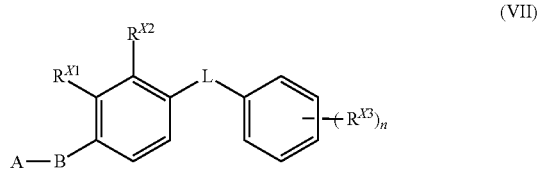

(VII)

wherein

A is pyrrolyl, pyrazolyl, imidazolyl, or indolyl, each optionally substituted with one to three $R^X$ groups;

B is 1,2,4-oxadiazole, 1,3,4-oxadiazole, 1,2-oxazole, 1,3-oxazole, triazole, pyrazole, imidazole, or dihydro-imidazole;

L is O, S, or NH;

n is 1, 2, 3, 4, or 5;

each $R^X$, $R^{X1}$, $R^{X2}$, and $R^{X3}$ is independently —H, —OH, halo, —N$_3$, —NO$_2$, —O-allyl, —C≡N, —CF$_3$, —OCF$_3$, —C(=O)CF$_3$, alkyl, alkoxy, phenyl, phenoxy, benzyl, or cycloalkyl —NR$^a$R$^b$, or —C≡C—R$^Y$;

each $R^a$ and $R^b$ are independently H, alkyl, or a nitrogen protecting group; and $R^Y$ is —H, alkyl, hydroxyalkyl, or a silicon protecting group;
or pharmaceutically acceptable salt or solvate thereof.

A compound of Formula (I) can also be a compound of Formula (VIII):

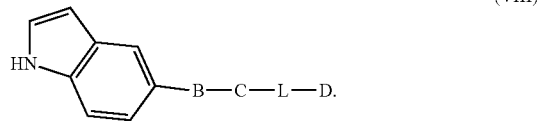

(VIII)

In any relevant Formula (I)-(VII), A can be 2-pyrrolyl, optionally substituted at the 4-position, 3-pyrazolyl, optionally substituted at the 4-position, 2-imidazolyl, or 5-indolyl.

In any relevant Formula (I)-(VII), B can be 1,2,4-oxadiazole.

In any relevant Formula (I)-(VII), C can be optionally substituted phenyl. Another specific value for C is optionally substituted bicyclic heteroaryl. An additional specific value for C is optionally substituted bicyclic heterocycle.

In any relevant Formula (I)-(VII), L can be O, or L can be S.

In any relevant Formula (I)-(VII), D can be phenyl, or phenyl substituted with —F or —CF$_3$.

A compound of Formula (I) can also be a compound of Formula (XI):

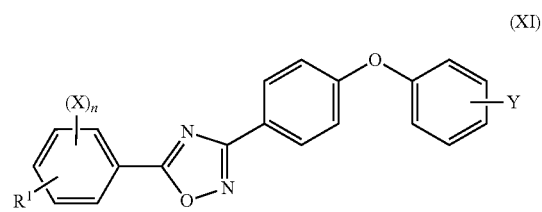

(XI)

wherein $R^1$ is OH, NH$_2$, NH(alkyl), halo, nitro, —CF$_3$, —C≡CH, —C≡N, —C≡C(C$_1$-C$_4$)alkyl, —C≡C(C$_1$-C$_4$)alkyl-OH, alkyl, alkoxy, alkenyloxy, phenyl, phenoxy, or cycloalkyl;

X is H, halo, or nitro;

n is 1 or 2;

or $R^1$ and X together with the phenyl ring to which they are attached form a five-membered nitrogen-containing ring; and Y is H, F, or CF$_3$;
or a pharmaceutically acceptable salt or solvate thereof. The compound of Formula (XI) can be a compound of Formula (XII):

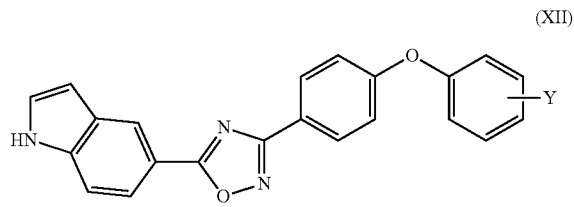

(XII)

wherein

Y is H, F, or CF$_3$;
or a pharmaceutically acceptable salt or solvate thereof. The group Y can be para to the oxygen of the phenyl ring to which it is attached. In other embodiments, Y can be ortho, or Y can be meta, to the oxygen of the phenyl ring to which it is attached.

In the formulas illustrated herein, when a group, moiety, or substituent is shown as located at a variable site of an aromatic or heteroaromatic ring, the variable nature of the bond of the structure is intended to provide the basis for a structure drawn to show the bond at any of the specific carbon or heteroatoms of the aromatic ring. Also, when a group or moiety can include one or more optional substituents (e.g., an $R^X$ group), the substituent can be located at any available location on the group or moiety, such as any available valency on a pyrrolyl, pyrazolyl, imidazolyl, or indolyl ring.

The invention also provides a pharmaceutical composition comprising a compound of any one of the formulas above, in combination with a pharmaceutically acceptable diluent or carrier.

The invention also provides a method for killing or inhibiting growth of gram positive bacteria comprising contacting gram positive bacteria with a compound or composition described herein, thereby killing or inhibiting the growth of the bacteria. The contacting can be performed in vivo in a human or animal, or in vitro, for example, in an assay. The gram positive bacteria can be of the genus *Enterococcus* or *Staphylococcus*. In certain embodiments, the bacteria is a drug-resistant strain of the genus *Staphylococcus*. In certain specific embodiments, the bacteria is a methicillin-resistant *Staphylococcus aureus* (MRSA) strain.

Accordingly, the invention provides novel compounds of a formula described herein, intermediates for the synthesis of compounds of a formula described herein, as well as methods of preparing compounds of a formula described herein. The invention also provides compounds of a formula described herein that are useful as intermediates for the synthesis of other useful compounds. The invention provides for the use of compounds of a formula described herein for the manufacture of medicaments useful for the treatment of bacterial infections in a mammal, such as a human.

The invention provides for the use of the compositions described herein for use in medical therapy. The medical therapy can be treating a bacterial infection. The invention also provides for the use of a composition as described herein for the manufacture of a medicament to treat a disease in a mammal, for example, a bacterial infection in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
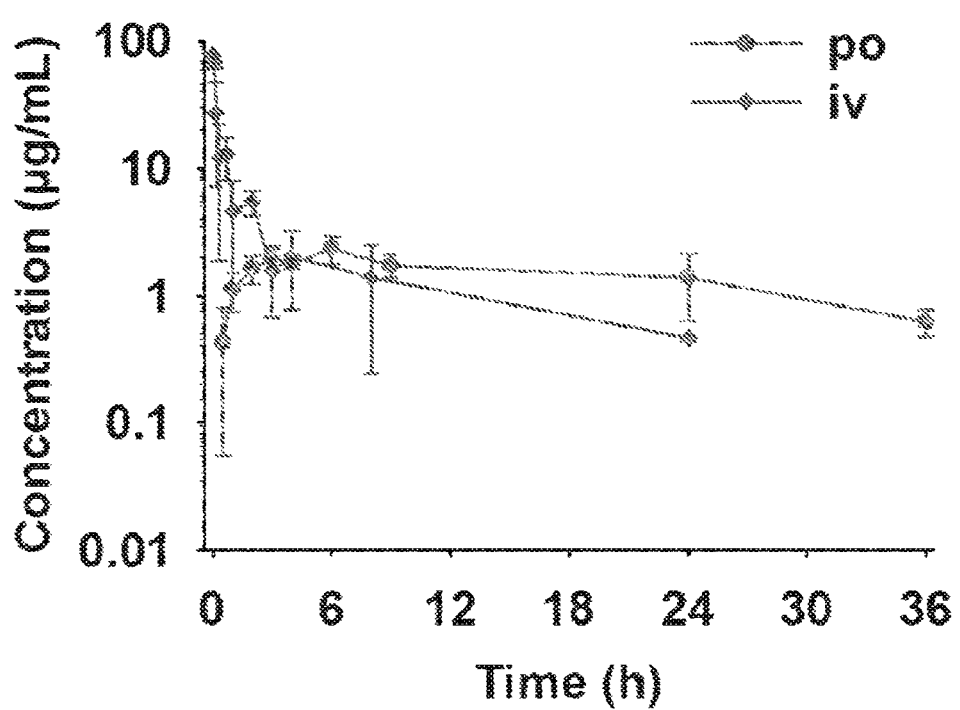
FIG. 1. Pharmacokinetics of 75b after single iv and po administration at 20 mg/kg to mice (n=3 per time point).

The invention provides a newly discovered oxadiazole class of antibiotics. The oxadiazoles impair cell-wall biosynthesis and exhibit activities against Gram-positive bacteria such as the bacterium *Staphylococcus aureus*, including methicillin-resistant *S. aureus* (MRSA) and vancomycin-resistant and linezolid-resistant *S. aureus*. For example, 5-(1H-indol-5-yl)-3-(4-(4-(trifluoromethyl)phenoxy)phenyl)-1,2,4-oxadiazole (compound 75b) was efficacious in a mouse model of MRSA infection, exhibiting a long half-life, a high volume of distribution, and low clearance. Antibiotic 75b is bactericidal and is orally bioavailable. This class of antibiotics can therefore be used as a therapeutic agent against infections by Gram-positive bacteria such as MRSA.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation. For example, the R groups of the formulas described herein (e.g., R, $R^1$, $R^2$, $R^3$, $R^X$, $R^Y$, and the like) can specifically exclude certain groups such as H, OH, halo, or specific halo groups including F, Cl, Br, or I, nitro, carboxy (—$CO_2H$), methoxy, methyl, trifluoromethyl, phenyl, nitrile, or any other group recited in the definitions of the R groups. The exclusion can be from one R group and not another. The exclusion can also be directed to a particular ortho, meta, or para position of a aryl or phenyl ring of one of the formulas. Accordingly, the formulas can exclude compounds that are known and/or that are not selected for a particular embodiment of the invention.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, stopping or reversing the progression or severity of the condition or symptoms being treated. As such, the term "treatment" can include medical and/or therapeutic administration, as appropriate.

The term "infection" refers to the invasion of the host by germs (e.g., bacteria) that reproduce and multiply, causing disease by local cell injury, release of poisons, or germ-antibody reaction in the cells. The compounds and compositions described herein can be used to treat a gram positive bacterial infection, for example, an infection in a mammal, such as a human.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting, for example, with an effective amount of an antibacterial compound or composition described herein.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imino (C=NH), sulfinyl (SO) or sulfonyl (SO$_2$). Additionally, the alkyl can optionally be at least partially unsaturated, thereby providing an alkenyl.

The term "alkenyl" refers to a $C_2$-$C_{18}$ hydrocarbon containing normal, secondary, tertiary or cyclic carbon atoms with at least one site of unsaturation, i.e., a carbon-carbon, sp$^2$ double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). The alkenyl can be a monovalent hydrocarbon radical, as described and exemplified above, or it can be a divalent hydrocarbon radical (i.e., alkenylene).

The alkenyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. Additionally, the alkenyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, pinenyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkoxy" refers to the group alkyl-O—, where alkyl is as defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "acyl" group refers to a group containing a carbonyl moiety wherein the group is bonded via the carbonyl carbon atom. The carbonyl carbon atom is also bonded to another carbon atom, which can be part of an alkyl, aryl, arylalkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen atom, the group is a "formyl" group, an acyl group as the term is defined herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group. An acyloxy group is an acyl moiety connected to an oxygen, which group can form a substituent group.

The term "amino" refers to —NH$_2$. The amino group can be optionally substituted as defined herein for the term "substituted." The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl. The various R groups described herein can be amino, alkylamino, or acylamino groups, in various embodiments.

The terms "amide" (or "amido") refer to C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H).

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group. The term "alkoxycarbonyl" refers to —C(=O)OR (or "COOR"), wherein R is an alkyl group as previously defined.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The terms "aryloxy" and "arylalkoxy" refer to, respectively, an aryl group bonded to an oxygen atom and an arylalkyl group bonded to the oxygen atom at the alkyl moiety. Examples include but are not limited to phenoxy, naphthyloxy, and benzyloxy. The term "aroyl" refers to an aryl-C(=O)— group.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. For example, the nitrogen of any indolyl ring can be N-substituted to provide an N-alkyl, N-methyl, or N-protecting group indolyl compound. A heteroaryl can also be substituted with a substituent as described in the substituents definition below.

The term "heterocycle" or "heterocyclyl" refers to a saturated or partially unsaturated ring system, containing at least one heteroatom selected from the group oxygen, nitrogen, and sulfur, and optionally substituted with alkyl, or $C(=O)OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. A heterocycle can also be substituted with a substituent as described in the substituents definition below.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —OH, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$H, —S(=O)$_2$OH, —S(=O)$_2$R, —OS(=O)$_2$OR, —S(=O)$_2$NHR, —S(=O)R, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

Protecting Groups. Compounds of the invention can further include one or more suitable protecting groups. The term "protecting group" refers to any group that, when bound to an sp-center, a hydroxyl, nitrogen, or other heteroatom prevents undesired reactions from occurring at this group and that can be removed by conventional chemical or enzymatic steps to reestablish the 'unprotected' moiety, such as an alkyne, hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silicon protecting groups ("silyl ethers") (e.g., trimethylsilyl (TMS), t-butyl-diphenylsilyl (TBDPS), triisopropylsilyl (TIPS), or t-butyldimethylsilyl (TBS)) and any other group that can be introduced chemically onto a hydroxyl or other moiety and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical nitrogen and oxygen protecting groups described in Greene (pages 14-118) include benzyl ethers, silyl ethers, esters including sulfonic acid esters, carbonates, sulfates, and sulfonates. For example, suitable nitrogen or oxygen protecting groups can include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenyl-methyl, tri(p-methoxyphenyl)methyl, 1,3-benzodithiolan-2-yl, benzisothiazolyl S, S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, me thoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, a-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number will be determined as set forth above.

The term "pharmaceutically acceptable salts" refers to ionic compounds, wherein a parent non-ionic compound is modified by making acid or base salts thereof. Examples of pharmaceutically acceptable salts include, mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, behenic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in *Remington: The Science and Practice of Pharmacy*, 21$^{st}$ edition, Lippincott, Williams & Wilkins, (2005).

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

The term "excipient" refers to an ingredient of the dosage form that is not medicinally active, but serves to dilute the API, assist in dispersion of the tablet in the patient's stomach, bind the tablet together, and serve other functions like stabilizing the API against decomposition.

Oxadiazole Antibiotics

We recently described the discovery of the oxadiazole class of antibiotics (O'Daniel et al., *J. Am. Chem. Soc.* 2014, 136, 3664-3672). A lead compound in this class came out of an in silico search for potential inhibitors for penicillin-binding protein 2a (PBP2a) of MRSA. PBPs are targets of β-lactam antibiotics. Inhibition of PBPs by β-lactams is bactericidal, as it interferes with biosynthesis of cell wall. Resistance to β-lactam antibiotics is widespread but the importance of PBPs as targets for antibiotics has not diminished. We reasoned that PBPs remain worthy targets for antibiotics, and we sought to discover a new class of non-β-lactam inhibitors for these enzymes in this effort.

The in silico search and scoring of 1.2 million compounds from the ZINC library led to selection and purchase of the top-ranked compounds for screening with living bacteria. We set the bar high from the outset by screening compounds first against *Escherichia coli* and the ESKAPE panel of antibiotics, instead of against the recombinant protein. The ESKAPE panel is comprised of *Enterococcus faecium, Staphylococcus aureus, Klebsiella pneumoniae, Acinetobacter baumannii, Pseudomonas aeruginosa,* and *Enterobacter* species, a collection of bacteria that cause the majority of nosocomial infections. This strategy for screening easily eliminates any compound that would not have activity against bacteria, so the search was streamlined. The research resulted in the discovery of the lead oxadiazole 1 (Scheme 1, which shows ring letter designations and oxadiazole ring numbering system).

Scheme 1. Structure of lead oxadiazole 1.

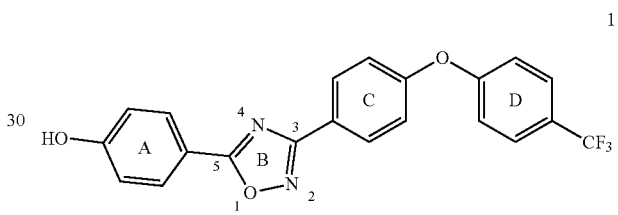

Described herein is the exploration of the structural space for oxadiazole antibiotics by syntheses of various new oxadiazole compounds. These compounds were in turn screened against a bacterial panel, from which a number exhibited good anti-MRSA activity. In another effort to streamline the discovery process, the promising compounds went directly into the mouse MRSA peritonitis model for infection. This model has shown excellent correlation between the minimal-inhibitory concentration (MIC) and $ED_{50}$ (the effective dose that rescues 50% of the animals from the infection) for 14 β-lactam antibiotics and for linezolid. This is a rapid animal model of infection that results in 100% fatality within 48 hours. The compounds that would show efficacy would by necessity exhibit reasonable pharmacokinetic (PK) properties. This approach sped up lead optimization by identifying compounds with in vivo activity early. The compounds that resulted in survival of the animals were then further scrutinized for optimization by additional syntheses around the structural space and for attributes such as improved PK, decreased metabolism, and lack of toxicity to mammalian cells. Ring A of oxadiazole 1 (Scheme 1) provided excellent opportunities for these additional explorations. These efforts led to the SAR for the oxadiazoles as studied by 120 synthetic ring A derivatives.

Synthesis. The focus of this SAR study was the variation of structure within Ring A of the oxadiazole lead. This ring, attached to position 5 of the 1,2,4-oxadiazole moiety, proved versatile in generating many active antibiotics of this class. The diphenyl ether portion (rings C and D) was obtained by reaction of either 4-fluorobenzonitrile (2) or 4-iodobenzonitrile (3) with the appropriate counterpart phenol (4a, 4b, or 4c, Scheme 2).

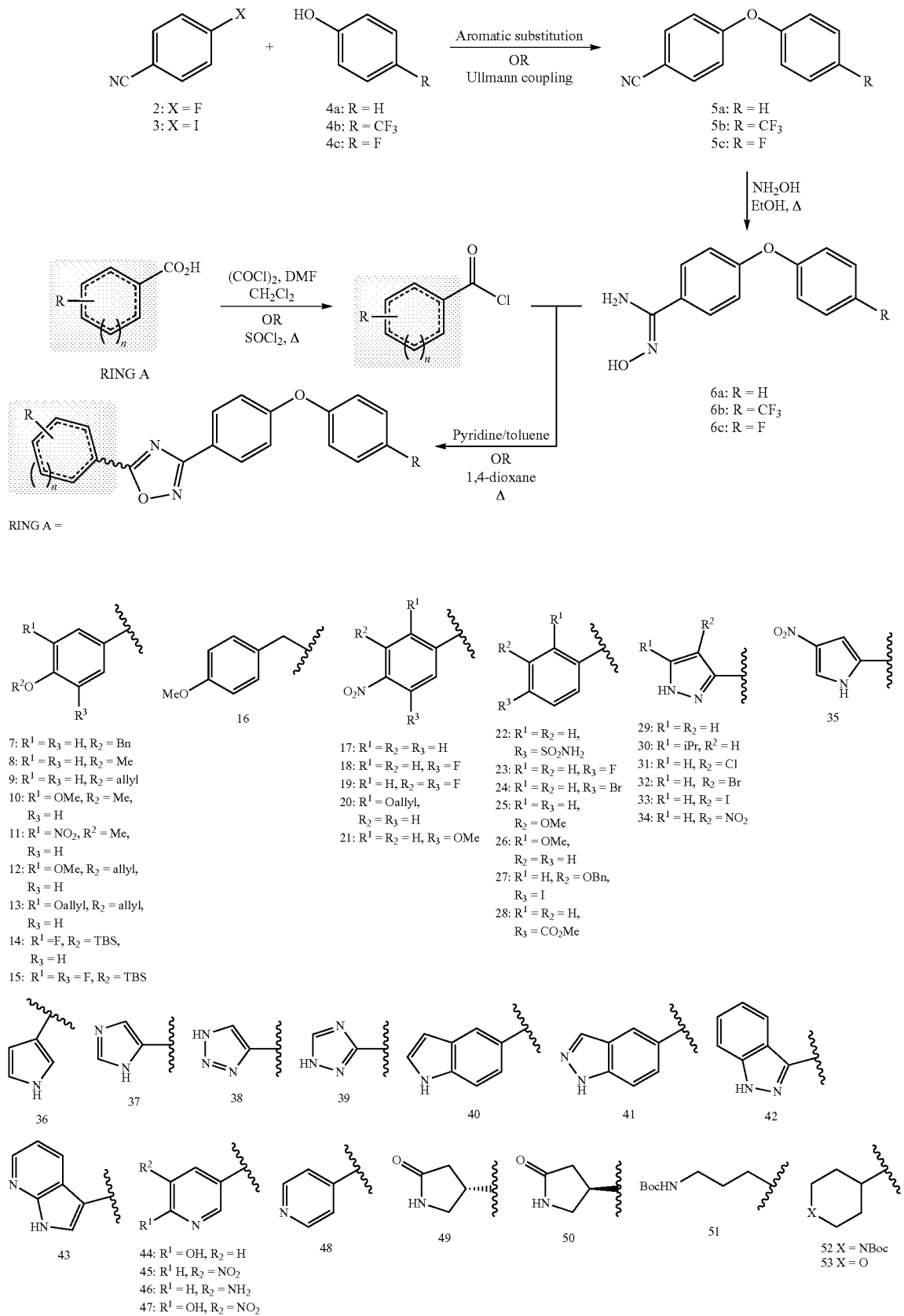

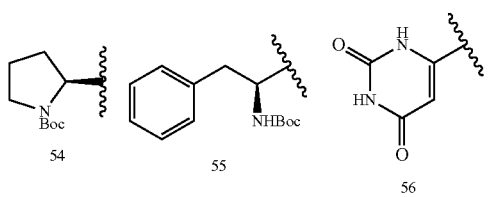

54   55   56

Compounds 14, 15, and 28 were prepared from acyl chlorides, compound 40 from a methyl ester, and all others from the corresponding carboxylic acids. Aromatic substitution: $K_2CO_3$, DMF, 60-100° C.; Ullmann coupling: CuI, $Cs_2CO_3$, N,N-dimethylglycine.HCl, 1,4-dioxane 90° C.

Typically, coupling with 2 was done via nucleophilic aromatic substitution, and the reaction with 3 was achieved with an Ullmann coupling. Our variations to the aromatic rings of the diphenyl ether were minimal and involved only substitution at the 4-position of ring D with a fluoro or trifluoromethyl group. The para substitution of ring D, specifically with those two variations, proved beneficial for improved metabolic stability and lowered clearance. Nitriles 5a, 5b, and 5c were converted into their corresponding N'-hydroxybenzimidamides 6a, 6b, and 6c, respectively, using hydroxylamine in refluxing ethanol.

The left-hand portions of the oxadiazoles (with respect to the structure shown in Scheme 1) were accessed by starting (with a few exceptions) with the corresponding carboxylic acids, which would ultimately become ring A and the $C_5$ of the oxadiazole ring (see Scheme 2). These were converted to the corresponding acyl chlorides by reaction with either oxalyl chloride or thionyl chloride. The starting materials included several benzoic acid derivatives (7-28) and a variety of heteroatom-containing carboxylic acids (29-56). Biological analysis of the lead compound 1 and a few close analogues established that a hydrogen bond donor at the 4-position of ring A is generally beneficial for activity against S. aureus. Thus, the phenolic hydroxyl was retained using several different protected derivatives (7-16), while the 4-amino group (for anilines) was accessed by starting with the corresponding 4-nitrobenzoic acid derivatives (17-21), wherein the nitro functionality was later reduced. We also explored the effect of several other substituents at the 4-position of the phenyl ring, as exemplified by precursors 22-28.

The heteroatom-containing starting materials included several pyrazoles (29-34), pyrroles (35, 36), imidazole 37, triazoles (38, 39), indole 40, indazoles (41, 42), pyrrolopyridine 43, pyridines (44-48), several aliphatic derivatives (49-53), protected amino acids (54, 55), and pyrimidine 56. While most of these precursors are commercially available, carboxylic acids 9, 12, 13, 20, 27, and 52, and acyl chlorides 14 and 15 had to be synthesized (procedures given in the Examples below). Once in hand, the acyl chlorides were allowed to react with 6a, 6b, or 6c in refluxing pyridine/toluene or 1,4-dioxane to produce the 1,2,4-oxadiazoles.

Many of these immediate oxadiazole products were subjected to further synthetic manipulation to broaden the structural diversity of the derivatives (protective group removal, nitro reduction, metal-catalyzed coupling, substitution on amine, etc.). These reactions are described in the Examples below.

Structure-Activity Relationship (SAR).

The SAR for the synthetic oxadiazole compounds was investigated using antibacterial screening against the aforementioned ESKAPE panel of bacteria plus E. coli. The 120 synthetic samples encompassed modifications in the lead at the 5-position of the 1,2,4-oxadiazole (ring A in Scheme 1), whilst keeping the 3-position constant as a 4-substituted di-phenyl ether moiety (Scheme 3). The oxadiazoles exhibit activity against Gram-positive bacteria.

We expressly explored the activity against S. aureus for this study. The SAR was evaluated by minimal-inhibitory concentration (MIC) measurements against S. aureus ATCC 29213, a standard methicillin-sensitive S. aureus (MSSA) strain for the purpose of screening. Highly active compounds (MIC≤8 μg/mL) are shown in Scheme 3 and less active compounds are shown in Scheme 4. The substituents at the 4-position of ring D were hydrogen, trifluoromethyl or fluorine (Scheme 3). These modifications had little effect on the in vitro activity of compounds, except for some specific cases that are discussed below. However, the substitution with trifluoromethyl or fluorine at this position resulted in lower clearance and better metabolic stability, thus improving the PK properties.

Scheme 3. Antibacterial activities of synthetic 1,2,4-oxadiazoles against S. aureus.

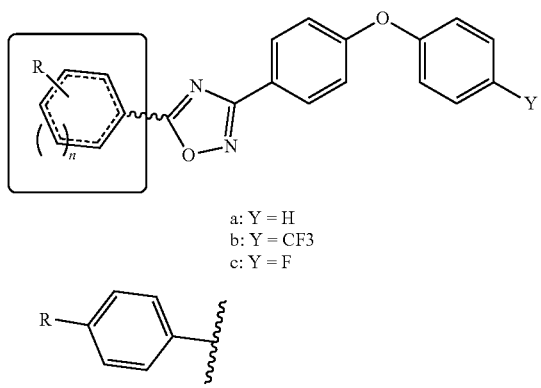

a: Y = H
b: Y = CF3
c: Y = F

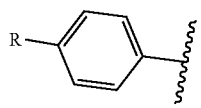

57a R = OH MIC = 1
57b R = OH MIC = 1
57c R = OH MIC = 1
58a R = $NH_2$ MIC = 4
58b R = $NH_2$ MIC = 1
59b R = $^+NH_3^-Cl$ MIC = 1

-continued

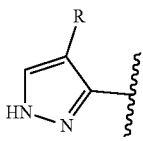

60a R = Cl MIC = 1
60b R = Cl MIC = 1
60c R = Cl MIC = 0.5
61a R = Br MIC = 1
61b R = Br MIC = 1
62a R = I MIC = 1
62b R = I MIC = 2
62c R = I MIC = 4
63a R = $NO_2$ MIC = 2
63b R = $NO_2$ MIC = 2
63c R = $NO_2$ MIC = 1
64b R = $NH_2$ MIC = 4
65a R = NH-iPr MIC = 0.5
65b R = NH-iPr MIC = 0.5
66b R = C≡CH MIC = 0.25
67b R = C≡CN MIC = 2
68b R = C≡C$CH_2$OH MIC = 4

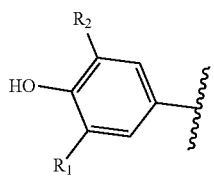

69b $R_1$ = OH, R = H MIC = 2
69c $R_1$ = OH, $R^2$ = H MIC = 4
70a $R_1$ = F, $R^2$ = H MIC = 4
70b $R_1$ = F, $R^2$ = H MIC = 2
70c $R_1$ = F, $R^2$ = H MIC = 2
71b $R_1$ = F, $R^2$ = F MIC = 2
71c $R_1$ = F, $R^2$ = F MIC = 8

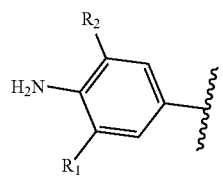

72b $R_1$ = F, $R^2$ = H MIC = 2
73a $R_1$ = F, $R^2$ = F MIC = 8
73b $R_1$ = F, $R^2$ = F MIC = 4

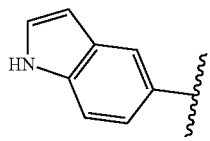

75a MIC = 2
75b MIC = 4
75c MIC = 1

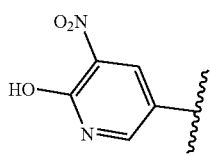

77b MIC = 8
77c MIC = 8

-continued

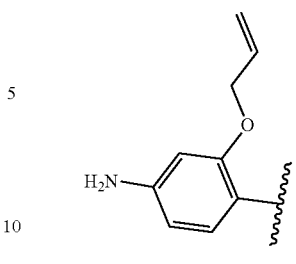

79a MIC = 8

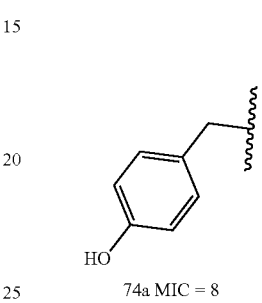

74a MIC = 8

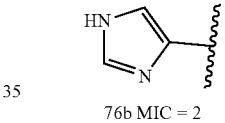

76b MIC = 2

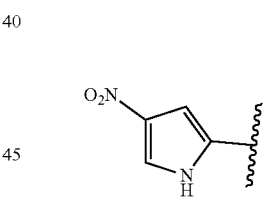

78c MIC = 8

Scheme 4. Antibacterial activities of 1,2,4-oxadiazoles (MIC > 8 μg/mL vs. *S. aureus*).

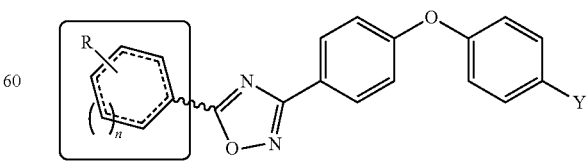

a: Y = H
b: Y = CF3
c: Y = F

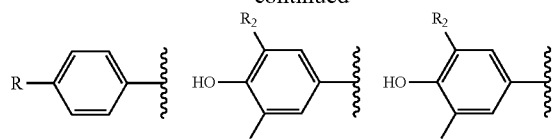
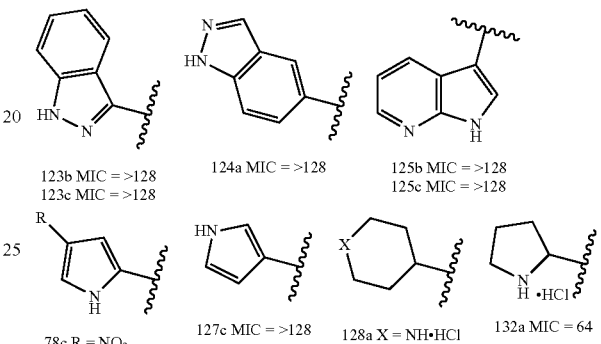
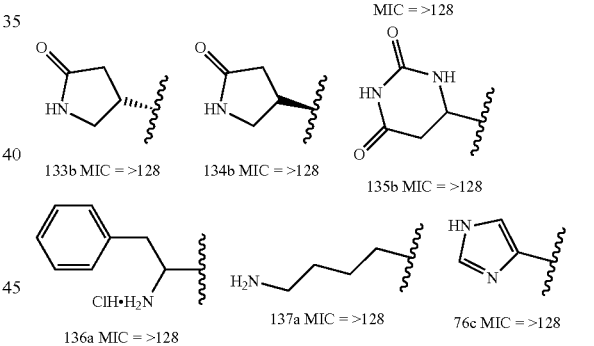

In Schemes 3 and 4, the functionality within the A Ring (shown within the box) was altered to generate a series of synthetic compounds, whereas Y was limited to the three entities that are indicated. The MIC values (in μg/mL) measured for *S. aureus* ATCC 29213 are shown, with highly active compounds shown in Scheme 3 (MIC≤8 μg/mL). Compounds 60b, 60c, 65b, 66b, 75b, and 76b underwent in vivo evaluation, discussed below. Compound 57b is identical to compound 1 and will be referred to as compound 1 in the remainder of the text.

Replacement of the phenol or aniline moieties in ring A with certain heterocyclic rings improved antibacterial activity. Introduction of 4-halogen-substituted pyrazoles (60a-c, 61a-b, 62a-c) maintained MIC values of ≤1 μg/mL. The pyrazolyl compounds also tolerated NO₂ (63a-c) and NH₂ (64b) substitution in this position, however introduction of an isopropyl group on the amine (65a-b) caused the MIC to drop further to 0.5 μg/mL. The lowest observed MIC value of 0.25 μg/mL came from the ethynyl substituted derivative 66b. Other sp-hybridized functional group substitutions (67b and 68b) also maintained good activity.

Addition of a 3-hydroxyl group (69b-c) retained activity, and the addition of fluorine atoms in the 3- and 5-positions on the phenol (70a-c and 71b-c) and the aniline (72b, 73a-b) was possible without significant loss of activity, but an additional methylene spacer between the 1,2,4 oxadiazole and the phenol ring (74a) increased the MIC to 8 μg/mL. The other heterocyclic substitutions that retained good activity were the indolyl compounds (75a-c), the imidazolyl compound (76b), the substituted pyridinyl compounds (77b-c) and the nitro substituted pyrrolyl compound (78b).

Replacement of the hydrogen-bond donating phenol and aniline groups with aryl halogens (80a-b, 81b-c) resulted in loss of activity, as did replacement with other hydrogen-bond accepting aryl moieties (82a-b, 84c). Interestingly, the aniline derivative with a 4-F substitution on the biphenyl ether (58c) had no antibiotic activity despite the low MIC values for the 4-H and 4-CF$_3$ substituted compounds (58a-b). All other substituted aryl systems failed to show significant activity (87b-c, 88c, 89c, 90c, 91c, 92c, 93b), including changing the hydroxyl group to the 2- or 3-positions (95a, 96a, 97a). No activity was seen for unsubstituted pyrazoles (102b-c) and the activity seen in the secondary amine series did not extend to larger straight chain alkyl or cyclic alkyl substitution (104b, 105b, 106b, 107b) or acylation (108b, 109b). Complete replacement of an aryl moiety with a simple hydroxyl (112a) or methyl (113a) abolishes activity and underlines the significance for activity of a spacing group between the 1,2,4-oxadiazole ring and the hydrogen-bond donating group. No activity was observed for any of the other heteroaromatic substituents that were introduced (114a, 115a, 116b, 117b, 118c, 119c, 120b-c, 121b-c, 122b-c, 123b-c, 124a, 125b-c, 78c, 126c, 127c).

In a similar trend observed with the inactive 4-F diphenyl ether substituted aniline (58c), the 4-F di-phenyl ether substituted imidazole derivative (76c) showed no activity compared to the active 4-CF$_3$ derivative (76b). The effect of the 4-position diphenyl ether substitutions on activity in these cases is yet to be resolved. Several derivatives with saturated cyclic substitutions were also synthesized, however activities were poor (≥32 μg/mL) (128a, 132a, 133b, 134b, 135b, 136a, 137a).

Activity Against Gram-Positive Organisms.

Compounds 60b, 60c, 65b, 66b, 75b, and 76b were evaluated against a panel of Gram-positive organisms. The pyrazoles showed activity against S. aureus MSSA (ATCC 29213) and MRSA (ATCC 27660, NRS119, VRS1, and VRS2) strains, including vancomycin-resistant strains (Table 1). The pyrazoles were not active against S. aureus NRS120 and other Gram-positive organisms. Replacement of the pyrazole with an indole (75b) broadened the spectrum of activity against Gram-positive organisms. The activity of the indole 75b was similar to that of the phenol derivative 1 (see Table 1 below).

TABLE 1

Minimal-inhibitory concentrations (MICs) of oxadiazoles. The compounds were screened against E. coli and the ESKAPE panel of bacteria; they exhibited antibacterial activity against Gram-positive bacteria.

| | MIC (μg/mL) | | | | | | | | |
|---|---|---|---|---|---|---|---|---|---|
| | 60b | 60c | 65b | 66b | 75b | 76b | 1 | vancomycin[h] | linezolid[h] |
| S. aureus ATCC 29213[a] | 1 | 1 | 0.5 | 0.25 | 2 | 4 | 2 | 1 | 4 |
| S. aureus ATCC 27660[b] | 2 | 0.5 | 0.5 | 0.5 | 4 | 8 | 2 | 1 | 2 |
| S. aureus NRS100 (COL)[b] | >128 | >128 | >128 | >128 | 2 | 32 | 2 | 2 | 2 |
| S. aureus NRS119[c] | 1 | 2 | 2 | 32 | 2 | 4 | 2 | 2 | 32 |
| S. aureus NRS120[c] | 64 | 64 | >128 | >128 | 2 | 16 | 2 | 2 | 32 |
| S. aureus VRS1[d] | 1-2 | 1 | 1 | 1 | 1 | 1 | 2 | 1-2 | 2 |
| S. aureus VRS2[e] | 0.5-1 | 0.5 | 4 | 0.5 | 4 | 16 | 2 | 64 | 2 |
| S. epidermis ATCC 35547 | >128 | >128 | >128 | >128 | 4 | 32 | 2 | 16 | 1 |
| S. haemolyticus ATCC 29970 | >128 | >128 | >128 | >128 | 8 | 16 | 2 | 2 | 2 |
| S. oralis ATCC 9811 | >128 | >128 | >128 | >128 | 128 | >128 | 32 | 0.5 | 1 |
| S. pyogenes ATCC 49399 | >128 | >128 | >128 | >128 | 64 | 128 | 32 | 0.6 | 1 |
| B. cereus ATCC 13061 | >128 | >128 | >128 | >128 | 16 | 16 | 2 | 1 | 1 |
| B. licheniformis ATCC 12759 | >128 | >128 | >128 | >128 | 8 | 16 | 2 | 0.5 | 1 |
| E. faecalis ATCC 29212[a] | >128 | >128 | >128 | >128 | 4 | 16 | 2 | 2 | 2 |
| E. faecalis 201 (Van S)[f] | >128 | >128 | >128 | >128 | 8 | 16 | 2 | 1 | 2 |
| E. faecalis 99 (Van R)[g] | >128 | >128 | >128 | >128 | 16 | 16 | 2 | 128 | 1 |
| E. faecium 119-39A (Van S)[f] | >128 | >128 | >128 | >128 | 8 | 16 | 1 | 0.5 | 2 |
| E. faecium 106 (Van R)[g] | >128 | >128 | >128 | >128 | 8 | 16 | 2 | 256 | 1 |
| E. faecium NCTC 7171 | 16 | 32 | 32 | >128 | 2-4 | 8-16 | 2 | 0.5 | 2 |

For Table 1:
[a]A quality-control strain to monitor accuracy of MIC testing;
[b]mecA positive, resistant to methicillin, oxacillin, and tetracycline; susceptible to vancomycin and linezolid;
[c]mecA positive, resistant to ciprofloxacin, gentamicin, oxacillin, penicillin, and linezolid;
[d]vancomycin-resistant MRSA (vanA) clinical isolate from Michigan;
[e]vancomycin-resistant MRSA (vanA) clinical isolate from Pennsylvania;
[f]vancomycin-susceptible clinical isolate;
[g]vancomycin-resistant clinical isolate.

Plasma-Protein Binding.

Protein binding for compounds 60b, 60c, 65b, 66b, 75b and 76b was determined in human plasma using equilibrium dialysis. Results are shown in Table 2. Protein binding of the pyrazoles 60b, 60c, 65b, 66b, and the imidazole 76b was lower than that of the indole 75b (98.2±3.2%). Although plasma protein binding was high, 43% of the 1,500 most frequently prescribed drugs have protein binding >90%, and 12 of the 100 most prescribed drugs have >98% plasma protein binding. Plasma protein binding of many antibiotics on the market include daptomycin, oxacillin, teicoplanin, rifampicin, and clindamycin is >91%.

TABLE 2

In vitro and in vivo evaluation of selected oxadiazole analogs.

| Antibiotic | Human plasma protein binding (%) | PK Parameters[a] AUC$_{0-8 h}$ (μg · min/mL) | CL (mL/min/kg) | XTT HepG2 IC$_{50}$ (μg/mL) | Mouse peritonitis (survived/total)[b] |
|---|---|---|---|---|---|
| 60b | 97.8 ± 0.3 | 910 | 22.0 | 24.1 ± 1.6 | 4/6 |
| 60c | 94.5 ± 2.1 | 446 | 44.9 | 18.2 ± 2.9 | 2/6 |
| 65b | 91.6 ± 0.3 | 1313 | 15.2 | 3.9 ± 0.8 | 1/6 |
| 66b | 96.4 ± 2.7 | 8261 | 2.4 | 9.8 ± 4.0 | 2/6 |
| 75b | 98.2 ± 3.2 | 1283 | 15.2 | 75.7 ± 7.3 | 5/6 |
| 76b | 93.5 ± 2.4 | 2054 | 9.7 | 31.5 ± 0.5 | 3/6 |
| 1 | 99.9 ± 0.1 | 2650[c] | 18.9[c] | 25.8 | ED$_{50}$ = 40 mg/kg[c] |

[a]PK parameters after a single iv dose at 20 mg/kg (n = 2 mice per 5 time points).
[b]Mouse peritonitis, *S. aureus* ATCC27660 given ip at 5 e7 cfu/mL with 5% mucin. Compounds were given iv at 20 mg/kg at 30 min and 7.5 h after infection.
[c]PK parameters for compound 1 at 50 mg/kg iv.

Fast Pharmacokinetic (PK) Studies.

To rapidly ascertain the PK properties of the compounds, fast PK studies were conducted. These studies involve administration of the compounds using a limited number of animals (n=2 mice per time point) for a few time points. This allows us to rapidly compare the preliminary PK properties of the compounds, so that full PK studies are conducted only with the most promising compound(s). All compounds were administered intravenously (iv) with a single dose at 20 mg/kg. The alkyne substituted pyrazole 66b had the lowest clearance and the highest systemic exposure, as measured by area under the curve (AUC, Table 2). The highest clearance was observed for 60c, and as a result it had the lowest systemic exposure.

In Vitro Cytotoxicity.

We used the XTT assay with HepG2 cells to evaluate the in vitro toxicity of compounds 60b, 60c, 65b, 66b, 75b and 76b (Table 2). The highest toxicity was observed for 65b and the lowest for the indole 75b. Compared to the lead 1, indole 75b was 5-fold less toxic.

In Vivo Efficacy.

Compounds 60b, 60c, 65b, 66b, 75b and 76b were evaluated in the mouse peritonitis model of infection (Table 2). We used the ICR out-bred strain of mice that provides a heterogeneous population, similar to the human situation, thus, ensuring the relevance of the antibacterial effect. This animal model of infection is widely used, it is easy to carry out, and the end points (death or survival) are rapidly assessed, making it less resource-intensive compared to other infection models. In addition, excellent correlation between MIC and ED$_{50}$ has been shown for 14 β-lactam antibiotics using this model (Kratochwil et al., *Biochem. Pharmacol.* 2002, 64, 1355). The mouse peritonitis infection model continues to be an important model for evaluation of the efficacy of antibiotics against human pathogens. We use the iv route of administration in initial efficacy studies, as this allows us to test the efficacy without knowledge of the oral bioavailability of the lead. Evaluation was done at 20 mg/kg. The highest efficacy was observed for indole 75b (Table 2).

Minimal-Bactericidal Concentration (MBC).

The MBC of compound 75b was determined using *S. aureus* ATCC 29213, *S. aureus* ATCC 277660, and *E. faecium* NCTC 7171. For *S. aureus* ATCC 29213 (an MSSA strain), the MBC was the same as the MIC value, while for the two other strains, the MBC was 2-fold above the MIC values. These data indicated that compound 75b is bactericidal at concentrations that inhibit bacterial growth.

Full PK Study.

A full PK study was conducted with indole 75b after iv and oral (po) administration. This compound had the lowest in vitro toxicity and the highest efficacy in the mouse peritonitis infection model. Results are summarized in Tables 3-4. Antibiotic 75b was characterized by low clearance of 5.68 mL/min/kg (less than 10% of hepatic blood flow), a high volume of distribution of 4.73 L/kg, and a terminal half-life after iv administration of 9.6 hours. After oral administration, maximum concentrations were observed at 6 hours, after which time relatively high concentrations were sustained. The terminal half-life after oral administration was long (18.6 h). The oral bioavailability of 75b at 97% was high, and was similar to that of compound 1. Antibiotic 75b had 13-fold higher volume of distribution and 3-fold lower clearance than 1 and was more rapidly absorbed than 1 ($t_{1/2abs}$ of 0.8 h vs 3.3 h) (Table 4). Thus, antibiotic 75b has superior PK properties compared to 1.

TABLE 3

In vivo efficacy of compound 75b in the mouse peritonitis model.

| Compound | Route of administration | Dose frequency | ED$_{50}$ (mg/kg) |
|---|---|---|---|
| 75b | iv | 2 doses given at 30 min and 7.5 h after infection | 7.6 |
| 75b | po | | 1.7 |
| 1 | iv | | 40 |
| 75b | po | single dose given at 1 h after infection | 3.1 |
| 1 | po | | 44 |
| linezolid | po | | 2.8 |

TABLE 4

Pharmacokinetic parameters of 75b.

| Dose (mg/kg) | $AUC_{0-24h}$ (μg·min/mL) | $AUC_{0-\infty}$ (μg·min/mL) | $C_{max}$ (μg/mL) | $T_{max}$ (h) | CL (mL/min/kg) | $V_d$ (L/kg) | $t_{1/2}$ | F (%) |
|---|---|---|---|---|---|---|---|---|
| 20 iv | 3140 | 3520 | — | — | 5.68 | 4.73 | $t_{1/2\alpha}$ = 0.54 min<br>$t_{1/2\beta}$ = 9.6 h | 97 |
| 20 po | 3060 | 4060 | 2.34 | 6 | — | — | $t_{1/2abs}$ = 0.83 h<br>$t_{1/2dist}$ = 15.9 h<br>$t_{1/2elim}$ = 18.6 h | |

In Vivo Efficacy of 75b.

Antibiotic 75b was evaluated in the mouse peritonitis infection model using *S. aureus* ATCC 27660 (MRSA) after iv and po administration (Table 3). The mean effective dose ($ED_{50}$) values were 7.6 mg/kg and 1.7 mg/kg after iv and po doses given at 30 min and 7.5 h after infection, respectively. The excellent oral efficacy was attributed to the sustained plasma concentrations of 75b following po administration. The $ED_{50}$ value after iv administration of 75b is 6-fold better than that of 1. The $ED_{50}$ of compound 75b was also evaluated after a single po dose given at 1 h after infection. Compound 75b has an excellent $ED_{50}$ of 3.1 mg/kg, comparable to that of linezolid of 2.8 mg/kg (Table 3) and 14-fold better than that of 1. These data indicated that antibiotic 75b is significantly superior than 1 and comparable in efficacy to linezolid.

In summary, the recent discovery of the oxadiazole class of anti-MRSA antibiotics provided the opportunity to explore the structural space for these cell-wall-active antibiotics. We have disclosed in the present work the SAR for this class by synthesis and evaluation of 120 structural variants, of which a few dozen exhibit antibacterial activity against *S. aureus* and MRSA strains. Certain heterocycles with the ability to donate hydrogen bonds are well tolerated at ring A. Thus, the 4-phenol (57a-59b, 69b-71c) and 4-aniline (72b-73b) analogs are active against *S. aureus*, but substituents such as phosphates (84c), sulfonamides (87b, 87c), amides (88c), and carboxylic acids (89c) attenuate or abrogate activity. Hydrogen bond-accepting substituents on ring A abolish activity (e.g. 80a-82b, 91c, 93b, 94a, 99a-101c). Replacing the phenyl moiety of ring A for an aromatic heterocyclic ring retains activity in some cases. Pyrazoles substituted with halogens (60a-62c), a nitro group (63a-63c), an isopropylamino group (65a, 65b), or sp-hybridized groups (66b-68b) are all active, as are indoles (75a-75c) and an imidazole (76b). Pyrazoles containing amino groups with larger substituents (104b-110b) lead to abolishment of antibacterial activity. Heteroaromatic systems such as pyridines (114a, 115a, 120b-122c), triazoles (116b, 117b), and pyroles (78c, 126c, 127c) generally abolish antibacterial activity, as do aliphatic heterocycles (128a-135b).

Although introducing a pyrazole at ring A generally results in compounds that are potently active in vitro with living bacteria, they are also generally cytotoxic. Thus, while pyrazole derivatives 65b and 66b are among the most active compounds reported here, they also exhibit the highest toxicity toward mammalian cells. Replacing the pyrazole with an indole circumvents these toxicity, while retaining antibacterial activity. One compound, antibiotic 75b, shows excellent efficacy in vivo with a long half-life, a high volume of distribution, and low clearance. Antibiotic 75b is bactericidal and is 97% orally bioavailable. This class of antibiotics holds great promise in treatment of infections by these difficult human pathogens.

Further Analysis of Oxadiazole Structure-Activity Relationships

The compound numbering of this section refers to the compounds shown below in Schemes 5-6 and Table 5, therefore a compound number that is repeated in this section does not refer to the compound numbering referenced above for the compounds described in Schemes 2-4 and Tables 1-4, above, and Examples 1-3 below.

The class of 1,2,4-oxadiazole antibiotics exhibits Gram-positive activity, particularly against *Staphylococcus aureus*. We define the structure-activity relationship (SAR) of this class of antibiotics with the synthesis and evaluation of a series of 59 derivatives with variations in the C ring or C and D rings. A total of 17 compounds showed activity against *S. aureus*. Four derivatives were evaluated against a panel of 16 Gram-positive strains, inclusive of several methicillin-resistant *S. aureus* strains. These compounds are broadly active against Gram-positive bacteria.

The Gram-positive bacterium *Staphylococcus aureus* is commensal to humans and exists on the skin and mucosa of 30% of the population. It is a principal cause of hospital infections, the most frequent and serious of which are bacteremia and endocarditis in hospitalized patients. This organism has become resistant to many different classes of antibiotics. Of special concern are the strains designated as methicillin-resistant *S. aureus* (MRSA), which are broadly resistant to most β-lactam antibiotics, agents of historic choice for treatment of infections by *S. aureus*. There has been recent activity in the discovery of novel antibiotics for treatment of *S. aureus* infections, but emergence of antibiotic-resistant variants is inevitable, necessitating search for novel classes of antibiotics effective against these organisms.

The 1,2,4-oxadiazole class of antibiotics targets the cell wall for inhibition, it exhibits good in vitro and in vivo activity, and it is orally bioavailable. The 1,2,4-oxadiazoles described herein are generally comprised of four rings, designated as A, B, C and D, as indicated by the representative compound 1.

1

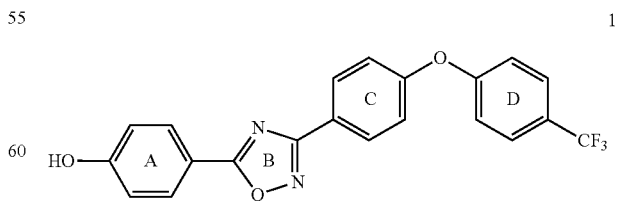

A hydrogen-bond donor in the A ring enhances antibacterial activity. The phenol, aniline and some heterocycles with hydrogen-bonding capability, such as pyrazoles, are tolerated. However, some substituents at this site such as sulfonamides, amides and carboxylic acids reduce the antibacterial activity or are inactive. Hydrogen-bond acceptors on the A ring are not favored. As indicated, pyrazoles with halogen substituents are all active, as is the indole at the A ring. Other variants with heteroaromatic systems such as pyridines, triazoles and pyrroles generally lose activity, as do the ones with aliphatic heterocycles.

We outline here our preparation and evaluation of a series of 59 additional oxadiazole analogs. In general, the derivatives have attempted to explore the effect of structural diversity on the antibacterial activity on the right-hand side of the molecule as shown for compound 1 above (i.e., the C and D rings). The diverse analogs were selected for variation in rings C or in rings C and D, inclusive of fused-ring variants (see Scheme 6 below). These studies further define the structure-activity relationship (SAR) for this class of antibacterials.

The general synthesis of this library followed the methodology shown in Scheme 5. Nitrile intermediates with the C and D rings fused are generally commercially available (examples 26 and 33). The nitrile intermediates 2-50 were key to the formation of the 1,2,4-oxadiazole derivatives. The biphenyl ether fragment can be formed through Ullmann reaction or aromatic substitution. The former takes place between aryl iodides and phenol in the presence of CuI, $Cs_2CO_3$ and N,N-dimethylglycine.HCl at 90° C. Nucleophilic aromatic substitution between the aryl fluorides and phenol was accomplished using $K_2CO_3$ as base. With the nitriles 2-50 in hand, the amidoximes were easily generated from the reaction between the nitrile and hydroxylamine in ethanol. Under the standard conditions, the acyl chloride was allowed to react with amidoxime in the presence of pyridine under reflux to afford the key 1, 2, 4-oxadiazole intermediates. Removal of the protective groups furnished the final compounds. For example, the Boc group was removed by exposure to acid and deprotection of the benzyl was performed in the presence of $BBr_3$.

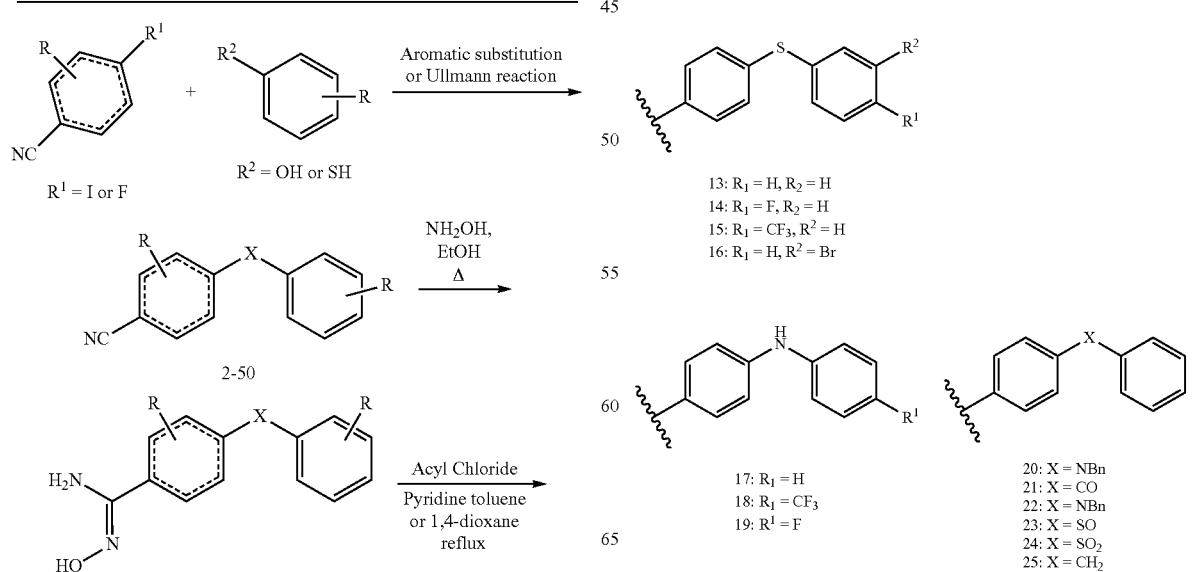

Scheme 5. General synthetic route to the 1,2,4-oxadiazoles, and the intermediates (2-50) used for variations within the C ring or the C and D rings fused.

-continued

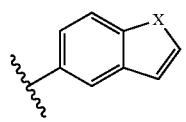

26: X = NCH₃
27: X = O
28: X = S
29: X = NBn

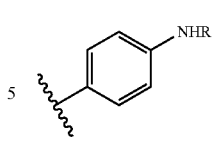

40: R = Boc
41: R = 4-piperidinyl•HCl
42: R = COCH₃
43: R = COPh

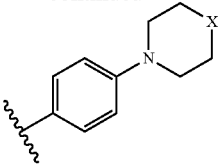

44: X = NBoc
45: X = NCH₃
46: X = O

Ring C and D =

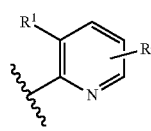

30: R₁ = H, R₂ = 3-(4-CF₃PhO)
31: R₁ = NO₂, R² = 3-(4-CF₃PhO)
32: R¹ = H, R² = 2-(4-CF₃PhO)

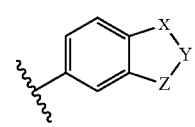

33: X = CO, Y = O, Z = CH₂
34: X = O, Y = CH₂, Z = O

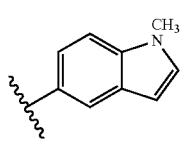

47

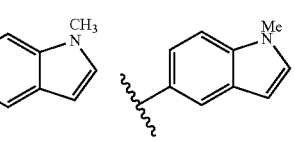

48    49

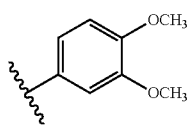

50

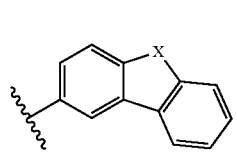

35: X = NCH₃
36: X = NH

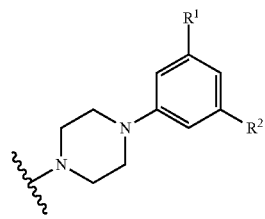

37: R₁ = H, R₂ = H
38: R₁ = Cl, R₂ = H
39: R₁ = R² = Cl

These compounds were screened for antibacterial activity by determination of minimal-inhibitory concentrations (MICs) against the ESKAPE panel of bacteria, including *S. aureus* ATCC29213. Active compounds were designated as those with MIC values of ≤8 µg/mL, which encompassed 17 of the synthetic compounds. The MIC data and the corresponding structures are listed in Scheme 6.

Scheme 6. Results in vitro antibacterial activity against *S. aureus* ATCC29213.

Ring A Variations:

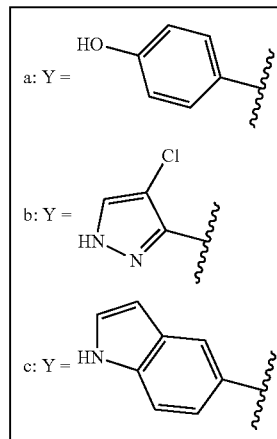

a: Y =
b: Y =
c: Y =

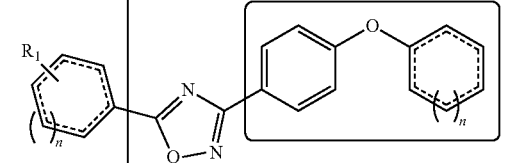

Ring C, C/D Variations Below:

Part A: Highly active against *S. aureus*.

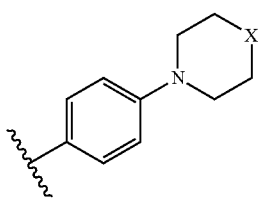

101a X = NH MIC = 32
102a X = NCH₃ MIC = >128
1037a X = O MIC = >128
104b X = NBoc MIC = >128
105b X = NH MIC = >128

The functional groups in ring C were changed to produce the synthetic compounds in this series and Y was limited to the three indicated entities. MIC values were measured in μg/mL and active compounds (Part A of Scheme 6) have an MIC≤8 μg/mL.

All the active derivatives (51a-67a) have the phenol moiety as the A ring. Compounds 51a and 52a displayed identical antibacterial potency with an MIC value of 2 μg/mL, which indicated that both the electron-withdrawing group chlorine and the electron-donating hydroxyl were well tolerated. Other substituents such as iodine, fluorine and the nitro group at the $R^1$ and $R^2$ positions showed the same trend. Interestingly, compound 68a with the $NH_2$ group at $R^2$ did not have any antibacterial activity. A small difference in antibacterial activity was observed between 55a and 58a with the switching of the $NO_2$ group between the $R^1$ and $R^2$ positions (MIC=4 μg/mL versus MIC=8 μg/mL). On the contrary, when the position of the azide was changed between $R^1$ and $R^2$, one compound (53a) demonstrated activity and the other (69a) was inactive. Intriguingly, chlorine as a substituent exhibited the opposite trend between the $R^1$ and $R^2$ positions (52a and 70a). Replacement of the bridging oxygen with sulfur, compounds 61a, 62a, 63a and 65a, did not alter the activity. Also, substitution of oxygen by the NH group (64a) retained activity, although there was a two-fold effect on the MIC value. It is of note that, compound 86a with the oxygen substituted by $CH_2$ resulted in inactivity, so did replacement of oxygen with NH (85a). The CO, SO and $SO_2$ groups at the same location behaved the same way, resulting in the loss of activity (87a, 89a and 90a). The more polar piperidine derivative 67a was active (MIC=8 μg/mL).

Other attempts to introduce piperidine (93a) or piperazine (102a) failed to produce active compounds. Compounds 74a-76a with pyridine rings were devoid of activity. Most of the compounds with the C and D rings fused were inactive, except 59a and 60a, which exhibited activity with an MIC of 8 μg/mL. Isomeric compounds 59a and 60a showed the same activity, indicating that the different positions for the indole nitrogen did not affect the antibacterial activity. The substitution of the indole nitrogen by O, S or NBn resulted in inactive compounds (71a, 72a and 73a). As described herein above, several derivatives with 4-chloro pyrazole or indole as the A ring and the biphenyl ether for the C and D rings have potent antibacterial activity. However, the variants prepared in the present study in which the C and D rings were fused did not result in active compounds.

This SAR effort based on a library of 59 compounds established a number of important observations on the oxadiazole antibiotics. These are: (i) structural variations on the C ring can support antibacterial activity; (ii) substitutions of oxygen for sulfur at the bridging moiety between rings C and D can generally be tolerated, but other moieties at the same site are detrimental; (iii) fusion of rings C and D with the phenol as the A ring retains activity; (iv) variations on the C ring abolish activity, if the A ring is either pyrazole or indole.

Antibiotics 51a-53a and 63a were evaluated with a larger panel of 16 Gram-positive bacteria, including antibiotic-resistant strains (Table 5). The properties of these strains are given in the footnotes to the table. These compounds in general exhibit broad activity against many of these leading Gram-positive bacterial pathogens.

TABLE 5

Minimal-Inhibitory Concentrations (MICs) of Oxadiazoles[a]

| | MIC (μg/mL) | | | | |
|---|---|---|---|---|---|
| microorganism | 51a | 52a | 53a | 63a | vancomycin[j] |
| S. aureus ATCC 29213[b] | 2 | 2 | 2 | 2 | 1 |
| S. aureus ATCC 27660[c] | 16 | 8 | 4 | 2 | 1 |
| S. aureus NRS100 (COL)[c] | 16 | 8 | 4 | 2 | 2 |
| S. aureus NRS119[d] | 8 | 4 | 4 | 2 | 2 |
| S. aureus NRS120[d] | 8 | 4 | 4 | 2 | 2 |
| S. aureus VRS1[e] | 8 | 2 | 2 | 2 | 512 |
| S. aureus VRS2[f] | 8 | 2 | 2 | 2 | 64 |
| S. epidermis ATCC 35547 | 16 | 4 | 2 | 2 | 16 |
| S. hemolyticus ATCC 29970 | 8 | 4 | 2 | 2 | 2 |
| B. cereus ATCC 13061 | 8 | 4 | 4 | 8 | 1 |
| B. licheniformis ATCC 12759 | 16 | 2 | 4 | 1 | 0.5 |
| E. faecalis ATCC 29212[b] | 8 | 4 | 2 | 2 | 2 |
| E. faecalis 201(Van S)[g] | 8 | 4 | 4 | 2 | 1 |
| E. faecalis 99(Van R)[h] | 16 | 4 | 4 | 2 | 128 |
| E. faecium 119-39A (Van S)[g] | 8 | 4 | 4 | 2 | 0.5 |
| E. faecium 106 (Van R)[h] | 8 | 4 | 4 | 2 | 256 |
| E. faecium C68[i] | 8 | 4 | 4 | 2 | 64[k] |

[a]Whereas the compounds were screened against the ESKAPE panel of bacteria, they exhibited antibacterial activity only against Gram-positive bacteria.
[b]A quality-control strain susceptible to methicillin to monitor accuracy of MIC testing.
[c]mecA positive, resistant to methicillin, oxacillin, and tetracycline; susceptible to vancomycin and linezolid.
[d]mecA positive, resistant to ciprofloxacin, gentamicin, oxacillin, penicillin, and linezolid.
[e]Vancomycin-resistant MRSA (vanA) clinical isolate from Michigan.
[f]Vancomycin-resistant MRSA (vanA) clinical isolate from Pennsylvania.
[g]Vancomycin-susceptible clinical isolate.
[h]Vancomycin-resistant clinical isolate.
[i]Clinical strain isolated in Cleveland hospitals; most prevalent vancomycin-resistant E. faecium strain from Cleveland hospitals.
[j]Data from reference 10; reproduced here for the sake of comparison.
[k]Data from reference 12; reproduced here for the sake of comparison.

We have thus described the design, synthesis and the antibacterial activity against Gram-positive bacteria of a series of 1,2,4-oxadiazole analogs with modifications on the C ring or on the fused C and D rings. This study defines the structural properties of this novel class of antibacterials, which emerged from an in silico search and screening.

Selected spectral data for representative compounds are provided in Example 4 below.

Useful compounds, compositions, methods and techniques that can be used in combination with the disclosure herein are described in U.S. Pat. No. 9,045,442 (Mobashery et al.), which is incorporated herein by reference.

Methods of the Invention

The binding of the compounds described herein to the allosteric site can predispose PBP2a to inactivation by β-lactam antibiotics. Additionally, the compounds described herein can synergize with β-lactams. This synergy can therefore resurrect presently obsolete β-lactam antibiotics in treatment of MRSA. Thus, the invention provides compositions of two or more antibiotics, which can be a synergistic combination for the treatment of a bacterial infection, such as MRSA.

Embodiments of the invention provide methods for killing bacteria or inhibiting the growth of bacteria using compounds described herein. In one embodiment, a method for inhibiting growth of bacteria is provided, comprising providing a source containing bacteria, and contacting the source with at least one compound described herein, such as a compound of a formula described herein, individually or in combination with other antibacterial compounds. In one embodiment, a bacterial infection in a human or an animal can be treated by administration of a compound described herein. In another embodiment, bacteria can be contacted with a compound described herein in vitro, for example, on an extracted sample or testing sample. In some embodiments, gram positive bacteria, and in particular, the PBPs on gram positive bacteria, can be effectively killed or inhibited. In certain embodiments, strains of *Enterococcus* and/or *Staphylococcus aureus* can be effectively killed or inhibited. In other embodiments, other bacterial strains may be targeted, such as but not limited to *M. tuberculosis, B. anthraces*, or others.

The compounds described herein can bind to the allosteric site of PBP2a and trigger opening of the active site. Beta-lactam antibiotics are not active against MRSA because they do not bind to the active site of PBP2a because the site is normally closed. Because the compounds described herein can bind to the allosteric site of PBP2a and trigger opening of the active site, they can act synergistically with other antibacterial agents, including beta-lactams. Thus, the compounds open a new strategy for resurrection of now defunct beta-lactam antibiotics for the effective treatment of bacterial infections.

Accordingly, the invention provides compositions that include a compound of a formula described herein, or a specific compound described herein, in combination with a second antibacterial agent. One class of antibacterial agents that can act synergistically when combined with a compound described herein for the treatment of a bacterial infection is the beta-lactam antibiotics. One specific antibacterial agent that can be combined with a compound described herein is ceftaroline. Other classes of antibacterial agents that can act synergistically when combined with a compound described herein for the treatment of a bacterial infection include aminoglycosides, tetracyclines, sulfonamides, fluoroquinolones, macrolides, polymyxins, glycylcyclines, and lincosamides.

Other antibacterial agent that can be used in combination with a compound described herein include, but are not limited to, amoxicillin, ampicillin, azlocillin, mezlocillin, apalcillin, hetacillin, bacampicillin, carbenicillin, sulbenicillin, ticarcillin, azlocillin, mecillinam, pivmecillinam, methicillin, ciclacillin, talampicillin, aspoxicillin, oxacillin, cloxacillin, dicloxacillin, flucloxacillin, nafcillin, pivampicillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefinenoxime, cefinetazole, cephaloglycin, cefonicid, cefodizime, cefpirome, ceftazidime, ceftriaxone, cefpiramide, cefbuperazone, cefozopran, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil cefditoren pivoxil, cefuroxime, cefuroxime axetil, daptomycin, loracarbacef, latamoxef and pharmaceutically acceptable salts, solvates or prodrugs thereof.

Additional antibacterial agent that can be used in combination with a compound described herein include, but are not limited to, cephalosporins, such as cefepime or a pharmaceutically acceptable salt, solvate or prodrug thereof; monobactams such as aztreonam or carumonam or a pharmaceutically acceptable salt, solvate or prodrug thereof; glycylcyclines such as tigecycline or a pharmaceutically acceptable salt, solvate or prodrug thereof, aminoglycosides, including, but not limited to, amikacin, gentamicin, kanamycin, neomycin, netilmicin, paromomycin, streptomycin, tobramycin and pharmaceutically acceptable salts, solvates or prodrugs thereof; carbapenems, including, but not limited to, imipenem, biapenem, meropenem, ertapenem, faropenem, doripenem, panipenem, PZ-601 and pharmaceutically acceptable salts, solvates or prodrugs thereof, macrolide, including, but not limited to, erythromycin, azithromycin, dirithromycin, telithromycin, clarithromycin and pharmaceutically acceptable salts, solvates or prodrugs thereof; fluoroquinolones, including, but not limited to, levofloxacin, ciprofloxacin, ofloxacin, gatifloxacin, norfloxacin, moxifloxacin, trovafloxacin and pharmaceutically acceptable salts, solvates or prodrugs thereof; acylaminopenicillins, such as piperacillin or a pharmaceutically acceptable salt, solvate or prodrug thereof; tazobactam or a pharmaceutically acceptable salt, solvate or prodrug thereof; daptomycin or a pharmaceutically acceptable salt, solvate or prodrug thereof.

The two antibacterial agents can be administered together, or they can be administered sequentially. In various embodiments, a compound described herein and a second antibacterial agents, for example, one recited above, can be administered in a combined dose of about 1 mg to 20 g/day in single or multiple administrations. In other embodiments, the combined dose may range from about 10 mg to 10 g/day. In still other embodiments, the combined dose may range from about 20 mg to 5 g/day. In certain embodiments, the combined dose may range from about 30 mg to 2 g/day. In certain specific embodiments, the combined daily dose may be about 20 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2750 mg, 2800 mg, 2850 mg, 2900 mg, 2950 mg, 3000 mg, 3.5 g, 4 g, 4.5 g, 5 g, 5.5 g, 6 g, 6.5 g, 7 g, 7.5 g, 8 g, 8.5 g, 9 g, 9.5 g or 10 g.

In certain embodiments, a compound described herein or a pharmaceutically acceptable salt, solvate or prodrug thereof can be administered in a daily dose ranging from about 0.5 mg/kg to about 400 mg/kg, preferably from about 2 mg to 40 mg/kg, of body weight of a human or an animal infected with pathogenic bacteria. In still other embodiments, the daily dose may range from about 5 to 30 mg/kg of body weight. In some embodiments, the daily dose may be about 20 mg/kg of body weight. In some embodiments, the daily dose may be administered in a singular dose, for example, every 24 hours. In other embodiments, the daily dose may be administered in two to six divided doses, for example, every 4 hours, 6 hours, 8 hours or 12 hours.

In some embodiments, a compound described herein or a pharmaceutically acceptable salt, solvate or prodrug thereof can be administered in doses ranging from about 1 mg to about 3000 mg per day in single or multiple administrations. In some embodiments, a compound described herein or a pharmaceutically acceptable salt, solvate or prodrug thereof may be administered in single or multiple doses of about 10 mg, 20 mg, 30 mg, 40 mg, 50 mg, 100 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg and 1800 mg per day. For example, the daily dose of a compound described herein or a pharmaceutically acceptable salt, solvate or prodrug thereof can be about 400 mg, about 600 mg, about 800 mg or about 1200 mg. The duration of treatment can be, for example, between five to seven days, five to ten days, five to fourteen days, or five to 21 days.

In some embodiments, the bacterial infection may be due to Gram-positive bacteria, including, but not limited to, methicillin resistant *Staphylococcus aureus* (MRSA), community-acquired methicillin resistant *Staphylococcus aureus* (CAMRSA), vancomycin-intermediate-susceptible *Staphylococcus aureus* (VISA), methicillin-resistant coagulase-negative staphylococci (MR-CoNS), vancomycin-intermediate-susceptible coagulase-negative staphylococci (VI-CoNS), methicillin susceptible *Staphylococcus aureus* (MSSA), *Streptococcus pneumoniae* (including penicillin-resistant strains [PRSP]) and multi-drug resistant strains [MDRSP]), *Streptococcus agalactiae, Streptococcus pyogenes* and *Enterococcus faecalis*. In particular embodiments, the bacterial infection may include, but is not limited to, complicated skin and skin structure infections (cSSSI); community acquired pneumonia (CAP); complicated intra-abdominal infections, such as, complicated appendicitis, peritonitis, complicated cholecystitis and complicated diverticulitis; uncomplicated and complicated urinary tract infections, such as, pyelonephritis; and respiratory and other nosocomial infections.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like.

The ability of a compound of the invention to treat an infection may be determined by using assays well known to the art. For example, the design of treatment protocols, toxicity evaluation, data analysis, quantification of cell kill, and the biological significance of the use of various screens are known. In addition, ability of a compound to treat an infection may be determined using the Tests as described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General experimental procedures for MIC determination and further information on synthetic procedures are provided below. Selected spectral data and their MIC values against Gram-positive organisms of the ESKAPE panel are also provided (see also FIG. 2).

Abbreviations: AUC, area under the curve; DMAP, Dimethyl amino pyridine; DMF, N,N-dimethylformamide; DMSO, dimethylsulfoxide; Et$_3$N, triethylamine; MIC, minimum-inhibitory concentration; MRSA, methicillin-resistant *Staphylococcus aureus*; PK, pharmacokinetics; TBS, tert-butyldimethylsilyl; THF, tetrahydrofuran; TLC, thin layer chromatography; UPLC, ultraperformance liquid chromatography; UV, ultraviolet.

Example 1. Non-Beta Lactam Antibiotics

In Silico Screening.

A library of 1.2 million drug-like compounds from the ChemDiv subset of the ZINC database (Irwin et al., *J. Chem. Inf. Model.* 2005, 45, 177) was prepared for high-throughput virtual screening against the X-ray structure of PBP2a (PDB ID: 1VQQ) (Lim et al., *Nat. Struct. Mol. Biol.* 2002, 9, 870). The protein was prepared using the Schrödinger Preparation Wizard (Schrödinger, LLC, 2009). The top scoring 10% of the compounds by Schrödinger Glide were cross-docked with Glide-SP, Autodock, Gold-chemscore, Gold-goldscore, and Gold-PLP. The top-scoring 2,000 poses from each were extracted and refined using Glide-XP mode. The best 2,500 compounds were clustered according to structural similarity using hierarchical clustering. Binding poses of these clusters were inspected visually. From these, 29 compounds were selected and purchased from ChemDiv for in vitro activity experiments.

Syntheses.

The synthetic procedures for the six compounds chosen for in vivo evaluation are detailed below. These are representative of the methods that were used for the preparation of other derivatives. Purity of the final products was generally >95%, as confirmed by HPLC. Detailed conditions are provided in the HPLC section.

Methyl 1H-indole-5-carboxylate (40)

1H-Indole-5-carboxylic acid (0.843 g, 5.23 mmol), methyl iodide (3.21 g, 22.7 mmol) and NaHCO$_3$ (1.76 g, 20.92 mmol) were stirred in DMF (24 mL) at room temperature for 3 days at which point water (50 mL) was added to the mixture forming a milky precipitate that was extracted with ethyl acetate (3×30 mL). The combined organic layer was washed with 5% LiCl (2×50 mL), dried over anhydrous Na$_2$SO$_4$, and the suspension was filtered. The filtrate was concentrated to dryness in vacuo to produce an off white solid, which was purified by silica-gel chromatography (ethyl acetate/hexanes, 1:10) to give the desired product as a white solid (0.820 g, 90%). $^1$H NMR (400 MHz, CDCl$_3$) δ 3.93 (s, 3H), 6.64 (m, 1H), 7.26 (m, 1H), 7.39 (dt J=8.6 Hz, 0.8 Hz, 1H), 7.91 (dd J=8.6 Hz, 1.6 Hz, 1H), 8.42 (m, 1H), 8.48 (s, 1H); $^{13}$C NMR (100 MHz, CDCl$_3$) 52.07, 104.24, 110.94, 122.15, 123.59, 124.00, 125.72, 127.69, 138.62, 168.50; HRMS (ESI): calcd for C$_{10}$H$_{10}$NO$_2$ [M+H]$^+$ 176.0706, found 176.0710.

5-(4-Chloro-1H-pyrazol-3-yl)-3-(4-(4-(trifluoromethyl)phenoxy)phenyl)-1,2,4-oxadiazole (60b)

This compound was synthesized using the same procedure as for 63b and purified by silica-gel chromatography (EtOAc/hexanes, 1:4) to yield the product as an off-white powder (58%). mp 193-195° C.; $^1$H NMR (400 MHz, CDCl$_3$) δ 7.16-7.19 (m, 4H), 7.66 (d, J=8.8 Hz, 2H), 8.02 (s, 1H), 8.17-8.20 (m, 2H), 13.58 (br, 1H); $^{13}$C NMR (100 MHz, DMSO-d$_6$) δ 110.8, 119.8, 120.6, 122.6, 124.8, 125.1, 128.3 (q, J=3.6 Hz), 130.1, 130.9, 134.1, 158.8, 159.9, 168.0, 170.2; HRMS (ESI): calcd for C$_{18}$H$_{11}$ClF$_3$N$_4$O$_2$ [M+H]$^+$ 407.0517, found 407.0540.

5-(4-Chloro-1H-pyrazol-3-yl)-3-(4-(4-fluorophenoxy)phenyl)-1,2,4-oxadiazole (60c)

This compound was synthesized using the same procedure as for 63b and was purified by silica-gel chromatography (EtOAc/hexanes, 1:6) to yield the product as an off-white powder (61%). mp 212-214° C.; $^1$H NMR (400 MHz, CDCl$_3$) δ 7.07-7.13 (m, 6H), 7.91 (s, 1H), 8.16 (d, J=9.2 Hz, 2H); $^{13}$C NMR (100 MHz, DMSO-d$_6$) δ 110.1, 116.8, 117.0, 117.9, 120.6, 121.8, 121.9, 129.3, 130.3, 133.5, 151.2, 151.3, 157.6, 160.0, 160.2, 167.4, 169.4; HRMS (ESI): calcd for C$_{17}$H$_{11}$ClFN$_4$O$_2$ [M+H]$^+$ 357.0549, found 357.0544.

5-(4-Iodo-1H-pyrazole-3-yl)-3-(4-(4-trifluoromethyl)phenoxy)phenyl)-1,2,4-oxadiazole (62b)

This compound was synthesized according to the procedure for 63b and was purified by silica-gel chromatography (EtOAc/hexanes, 1:3.5) to afford compound 62b as an off-white powder (64.0%). mp 222-225° C.; $^1$H NMR (400 MHz, DMSO-d$_6$) δ 7.29-7.36 (m, 4H), 7.80 (d, J=8.8 Hz, 2H), 8.16 (d, J=8.4 Hz, 2H), 8.31 (s, 1H); $^{13}$C NMR (100 MHz, DMSO-d$_6$) δ 60.4, 119.1, 120.0, 122.1, 122.8, 124.1, 124.4, 125.5, 127.6 (q, J=3.5 Hz), 129.4, 137.4, 138.3, 158.1, 159.2, 167.3, 170.4; HRMS (ESI): calcd for C$_{18}$H$_{11}$F$_3$IN$_4$O$_2$ [M+H]$^+$ 498.9873, found 498.9879.

5-(4-Nitro-1H-pyrazole-3-yl)-3-(4-(4-(trifluoromethyl)phenoxy)phenyl)-1,2,4-oxadiazole (63b)

4-Nitropyrazole-3-carboxylic acid (34, 0.24 g, 1.50 mmol) was dissolved in SOCl$_2$ (2.2 mL, 30.548 mmol) and the solution was stirred at reflux for 2 h. The excess SOCl$_2$ was evaporated to dryness in vacuo and the residue was taken up in toluene (15 mL) and pyridine (0.61 mL, 7.0 mmol), followed by the addition of (Z)—N'-hydroxy-4-(4-(trifluoromethyl)phenoxy)benzimidamide (6b, 0.30 g, 1.0 mmol). The resultant mixture was stirred at reflux overnight. The solvent was evaporated to dryness in vacuo and the residue was purified by silica-gel chromatography (CH$_2$Cl$_2$/MeOH, 100:1) to afford the title compound as a yellow powder (0.20 g, 48.0%). mp 204-206° C.; $^1$H NMR (400 MHz, CDCl$_3$) δ 7.15-7.18 (m, 4H), 7.65 (d, J=8.4 Hz, 2H), 8.18-8.20 (m, 2H), 8.55 (s, 1H); $^{13}$C NMR (100 MHz, CDCl$_3$) δ 120.0, 120.5, 122.2, 123.5, 125.0, 125.3, 126.2, 128.3 (q, J=3.5 Hz), 130.2, 133.1, 134.8, 159.2, 159.8, 168.4, 169.3; HRMS (ESI): calcd for C$_{18}$H$_{10}$F$_3$N$_5$NaO$_4$ [M+Na]$^+$ 440.0577, found 440.0579.

3-(3-(4-(4-(Trifluoromethyl)phenoxy)phenyl)-1,2,4-oxadiazol-5-yl)-1H-pyrazol-4-amine (64b)

Anhydrous THF (5 mL) was slowly added to a mixture of sulfur (0.22 g, 6.86 mmol) and sodium borohydride (74.4 mg, 1.96 mmol) in a round-bottom flask at room temperature. After stirring for 10 minutes, compound 63b (0.10 g, 0.24 mmol) in THF (2.0 mL) was added dropwise to the above mixture before heating it to 65° C. for 2.5 h. Upon cooling to room temperature, water (6 mL) and diethyl ether (6 mL) were added and the mixture was stirred for five minutes. The layers were separated and the aqueous portion was extracted with diethyl ether (3×12 mL). The combined organic layer was washed with brine, dried (Na$_2$SO$_4$) and was concentrated to dryness in vacuo. The residue was purified by silica-gel chromatography (EtOAc/hexanes, 1:2 to 2:1) to yield the title compound as a yellow foam (75.4 mg, 80.0%). mp 184-187° C.; $^1$H NMR (400 MHz, CDCl$_3$) δ 7.07-7.13 (m, 4H), 7.48 (s, 1H), 7.63 (d, J=8.4 Hz, 2H), 8.08 (d, J=8.4 Hz, 2H); $^{13}$C NMR (100 MHz, DMSO-d$_6$) δ 118.3, 119.0, 119.2, 122.3, 124.1, 126.0, 126.3, 127.5 (q, J=4.0 Hz), 129.5, 132.4, 158.6, 159.2, 167.3, 170.0; HRMS (ESI): calcd for C$_{18}$H$_{13}$F$_3$N$_5$O$_2$ [M+H]$^+$ 388.1016, found 388.1010.

N-Isopropyl-3-(3-(4-(4-(trifluoromethyl)phenoxy)phenyl)-1,2,4-oxadiazol-5-yl)-1H-pyrazol-4-amine (65b)

To a solution of compound 64b (75.4 mg, 0.19 mmol) and acetone (17 μL, 0.23 mmol) in 5 mL CH$_2$Cl$_2$ were added activated 3-Å molecular sieves and sodium triacetoxyborohydride (62.0 mg, 0.29 mmol). The mixture was stirred at room temperature for 7 days. The mixture was filtered through Celite, which was washed with EtOAc. The filtrate was concentrated to dryness and the residue was purified by silica-gel chromatography (EtOAc/hexanes, 1:3) to afford the desired product as a viscous oil (44 mg, 53%). mp 158-161° C.; $^1$H NMR (400 MHz, CDCl$_3$) δ 1.33 (s, 3H), 1.35 (s, 3H), 3.50-3.56 (m, 1H), 7.15-7.20 (m, 4H), 7.47 (s, 1H), 7.65 (d, J=8.8 Hz, 2H), 8.18-8.21 (m, 2H); $^{13}$C NMR (100 MHz, CDCl$_3$) δ 23.2, 47.8, 116.0, 119.1, 119.6, 122.8, 122.9, 125.9, 126.2, 127.6 (q, J=3.7 Hz), 129.8, 135.7, 158.9, 159.6, 167.6, 170.6; HRMS (ESI): calcd for C$_{21}$H$_{19}$F$_3$N$_5$O$_2$ [M+H]$^+$ 430.1485, found 430.1489.

5-(4-Ethynyl-1H-pyrazol-3-yl)-3-(4-(4-(trifluoromethyl)phenoxy)phenyl)-1,2,4-oxadiazole (66b)

Compound 103b (0.12 g, 0.26 mmol), KF (31 mg, 0.53 mmol) and 10 mL MeOH were placed in a round-bottom flask. The mixture was stirred at room temperature for 17 h. After the completion of the reaction, the solvent was removed in vacuo and the residue was purified by silica-gel chromatography (EtOAc/hexanes, 1:4) to give the compound as an off-white powder (84.7 mg, 81%). mp 206-209° C.; $^1$H NMR (500 MHz, CDCl$_3$) δ 3.39 (s, 1H), 7.14-7.19 (m, 4H), 7.64 (d, J=8.5 Hz, 2H), 8.06 (s, 1H), 8.21-8.23 (m, 2H); $^{13}$C NMR (100 MHz, CDCl$_3$) δ 72.8, 83.1, 119.2, 119.8, 122.5, 122.9, 125.6, 126.0, 126.4, 127.6 (q, J=3.6 Hz), 129.9, 159.1, 159.5, 168.5, 169.6; HRMS (ESI): calcd for C$_{20}$H$_{12}$F$_3$N$_4$O$_2$ [M+H]$^+$ 397.0907, found 397.0914.

5-(1H-Indol-5-yl)-3-(4-(4-(trifluoromethyl)phenoxy)phenyl)-1,2,4-oxadiazole (75b)

A solution of N-hydroxy-4-(4-(trifluoromethyl)phenoxy)benzimidamide (6b, 1.02 g, 3.44 mmol) in anhydrous THF (15 mL) was stirred under an argon atmosphere and sodium hydride (60% in mineral oil, 0.172 g, 4.30 mmol) was added to the flask. The mixture was left to stir for 1 h at room temperature, then a solution of methyl 1H-indole-5-carboxylate (40, 0.302 g, 1.72 mmol) in anhydrous THF (15 mL) was added and the mixture heated at reflux for 3.5 h. Once the solution had cooled to room temperature, water (50 mL) was added and the resulting mixture was extracted with ethyl acetate (3×50 mL). The combined organic layer was dried over anhydrous Na$_2$SO$_4$, then filtered and the filtrate was evaporated to leave an orange residue. This was purified using column chromatography on silica gel (dichloromethane/hexanes, 9:1) to give the desired product as a white solid (0.190 g, 26%). mp 138-141° C.; $^1$H NMR (400 MHz, CDCl$_3$) δ 6.69 (m, 1H), 7.11 (d, J=9.0 Hz, 2H), 7.14 (d, J=8.9 Hz, 2H), 7.29 (m, 1H), 7.48 (dt J=8.5 Hz, 1.6 Hz 1H), 7.61 (d, J=9.0 Hz 2H), 8.03 (dd, J=8.6 Hz, 1 Hz, 1.6 Hz 1H), 8.20 (d, J=8.9 Hz, 2H), 8.55 (m, 1H), 8.63 (s, 1H); $^{13}$C NMR (100 MHz, CDCl$_3$) δ 104.22, 111.92, 116.20, 118.90, 119.75, 122.09, 122.32, 123.49, 124.31 (q, J=272.2 Hz), 125.90 (q, J=32.9 Hz), 126.22, 127.50 (q, J=3.6 Hz), 128.19, 129.71, 138.38, 158.56, 159.72, 168.34, 177.40; $^{19}$F NMR (376 MHz, CDCl$_3$) δ 99.90 (s, 3F); HRMS (ESI): calcd for C$_{23}$H$_{14}$F$_3$N$_3$O$_2$ [M+H]$^+$ 422.1111, found 422.1078.

5-(1H-Imidazol-4-yl)-3-(4-(4-(trifluoromethyl)phenoxy)phenyl)-1,2,4-oxadiazole (76b)

The compound was synthesized according to the procedure used for 63b and purified by silica-gel chromatography (EtOAc/hexanes, 1:4 to 1:1.5) to afford the product as an off-white powder (72.0%). mp 243-245° C.; $^1$H NMR (400 MHz, DMSO-d$_6$) δ 7.29-7.31 (m, 4H), 7.80 (d, J=8.8 Hz, 2H), 7.99 (s, 1H), 8.12 (d, J=8.4 Hz, 2H), 8.24 (s, 1H), 13.00 (br, 1H); $^{13}$C NMR (100 MHz, DMSO-d$_6$) δ 119.2, 119.8, 122.4, 122.5, 124.1, 124.4, 126.3, 127.7 (d, J=3.0 Hz), 129.4, 138.3, 158.0, 159.2, 167.2, 172.2; HRMS (ESI): calcd for C$_{18}$H$_{12}$F$_3$N$_4$O$_2$ [M+H]$^+$ 373.0907, found 373.0911.

3-(4-(4-Trifluoromethyl)phenoxy)phenyl)-5-(4-((trimethylsilyl)ethynyl-1H-pyrazol-3-yl)-1,2,4-oxadiazole (103b)

Compound 62b (0.19 g, 0.38 mmol) was placed in a 10-mL round-bottom flask and 5 mL anhydrous THF was added to the flask. Ethynyltrimethylsilane (0.12 mL, 0.84 mmol), Pd(Ph$_3$P)$_2$Cl$_2$ (21.4 mg, 0.03 mmol), CuI (9.00 mg, 0.05 mmol) and Et$_3$N (0.14 mL, 0.99 mmol) were added to the above mixture. The resultant solution was heated in reflux for 5 h. After completion of the reaction, the solvent was evaporated to dryness in vacuo and the residue was purified by silica-gel chromatography (EtOAc/hexanes, 1:6) to afford the product as a white foam (0.14 g, 79.5%). $^1$H NMR (400 MHz, CDCl$_3$) δ 0.32 (s, 9H), 7.15-7.19 (m, 4H), 7.65 (d, J=8.8 Hz, 2H), 8.18 (s, 1H), 8.22 (d, J=8.8 Hz, 2H); $^{13}$C NMR (100 MHz, CDCl$_3$) δ 0.1, 93.7, 100.8, 105.5, 119.2, 119.7, 122.6, 122.9, 125.6, 126.0, 126.4, 127.6 (q, J=3.7 Hz), 129.9, 135.6, 138.5, 159.1, 159.4, 159.5, 168.5, 169.8; HRMS (ESI): calcd for C$_{23}$H$_{20}$F$_3$N$_4$O$_2$Si [M+H]$^+$ 469.1303, found 469.1336.

High Performance Liquid Chromatography (HPLC).

The system used was a PerkinElmer Series 200 Chromatography System (PerkinElmer, Waltham, Mass., USA) equipped with an autosampler, UV/VIS detector, LC pump, NCI 900 Network Chromatography Interface, and 600 Series Link Chromatography Interface. The samples were analyzed on a Zorbax RX-C8 analytical column (5.0 μm, 4.6 mm i.d.×250 mm, Agilent Technologies, Santa Clara, Calif., USA). The mobile phase consisted of isocratic elution for 10 min with a 1:1 mixture of water/0.1% trifluoroacetic acid (TFA) and acetonitrile/0.1% TFA at a flow rate of 1.0 mL/min, with the effluent monitored by UV detection (detection window set to 250-255 nm).

Example 2. General Experimental Procedures and Spectral Data

General Procedure for Synthesis of Benzoyl Chlorides and Heteroaryl Acyl Chlorides.

The general procedure for synthesis of various benzoyl chlorides has been previously described by, for example, O'Daniel et al., J. Am. Chem. Soc. 2014, 136, 3664-3672. For heteroaryl acyl chlorides, the carboxylic acid (1.0 equiv) was dissolved in thionyl chloride (25 equiv), and the mixture was heated to reflux for 2.5 hours. The excess thionyl chloride was removed in vacuo, and the resulting solid was used without further purification.

General Procedure for Synthesis of Diphenyl Ethers, Method A (Nucleophilic Aromatic Substitution).

A 4-fluorobenzonitrile derivative (1.0 equiv.), a phenol derivative (1.0 equiv.), and K$_2$CO$_3$ (2.0 equiv.) were dissolved in either DMSO or DMF, and the mixture was stirred at 100° C. for 16 h. The mixture was cooled to room temperature and was diluted with water (2× volume of DMSO or DMF used), then it was extracted with ethyl acetate (3×). The combined organic layer was washed with water (3×), then once with brine, and dried (anhydrous Na$_2$SO$_4$). After being concentrated in vacuo, the crude material was purified by column chromatography on silica gel.

General Procedure for Synthesis of Diphenyl Ethers, Method B (Ullmann Coupling).

The synthesis of diphenyl ethers was carried out generally as described by O'Daniel et al., *J. Am. Chem. Soc.* 2014, 136, 3664-3672.

Procedure for Nitro Reduction Using Fe/HCl.

The procedure for nitro reduction was carried out generally as described by O'Daniel et al., *J. Am. Chem. Soc.* 2014, 136, 3664.

General Procedure for Nitro Reduction Using $SnCl_2 \cdot H_2O$.

Using an adaptation of a literature procedure (Bellamy et al., *Tetrahedron Lett.* 1984, 25, 839-842), the starting material (1.0 equiv.) was dissolved in ethanol (6.0 mL/mmol starting material), and $SnCl_2 \cdot 2H_2O$ (5.0 equiv.) was added. The mixture was stirred at 70° C. for 4 hours, then cooled to room temperature (~23° C.) and poured onto ice. The pH was adjusted to ~7-8 with saturated $NaHCO_3$, and the aqueous layer was extracted 3× with ethyl acetate. The combined organic layers were dried (anhydrous $Na_2SO_4$), and the solvent was removed in vacuo. The crude product was purified by column chromatography on silica gel.

General Procedure for Synthesis of N'-Hydroxybenzimidamides.

The procedure for synthesis of N'-hydroxybenzimidamides was carried out generally as described by O'Daniel et al., *J. Am. Chem. Soc.* 2014, 136, 3664-3672.

General Procedure for Synthesis of Allyl-Protected Phenols.

Allyl-protected phenols 9 (Yi et al., *Bioorg. Med. Chem.* 2013, 21, 4730-4743), 12 (Wilson et al., *Tetrahedron Lett.* 1995, 36, 6333-6336), 13 (Liu et al., *J. Med. Chem.* 2012, 55, 8493-8501), and 20 (Coppola et al., *J. Med. Chem.* 2005, 48, 6696-6712), are known compounds and were synthesized using previously described procedures (Yi et al., *Bioorg. Med. Chem.* 2013, 21, 4730-4743). Compounds 52, 14, and 15 were synthesized using previously described procedures (O'Daniel et al., *J. Am. Chem. Soc.* 2014, 136, 3664-3672; Perez et al., *J. Med. Chem.* 2009, 52, 5826-5836).

TABLE 2.1

Spectral data of compounds of Schemes 2-4.

| Compound Number | Structure and data |
|---|---|
| 57a | 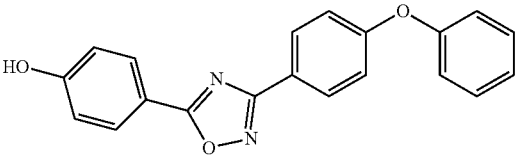 Lit. |
| 57b | 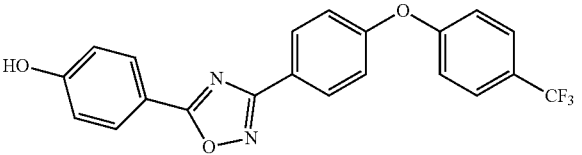 Lit. |
| 57c | 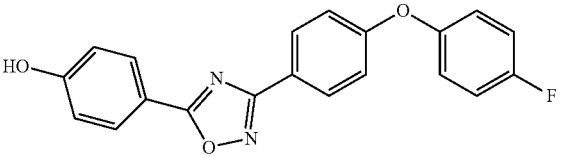 [SMILES: Oc1ccc(-c2nc(-c3ccc(Oc4ccc(F)cc4)cc3)no2)cc1] |
| | $^1$H NMR (500 MHz, DMSO-$d_6$) δ 6.99 (d, J = 8.6 Hz, 2H), 7.14 (d, J = 8.6 Hz, 2H), 7.19-7.22 (m, 2H), 7.28-7.32 (m, 2H), 8.02 (d, J = 8.6 Hz, 2H), 8.06 (d, J = 8.6 Hz, 2H). |
| | $^{19}$F NMR (282 MHz, DMSO-$d_6$) δ −118.89. |
| | HRMS (ESI) calcd for $C_{21}H_{14}FN_2O_3$ 349.0983, found 349.0978 $[MH]^+$ |
| 58 | 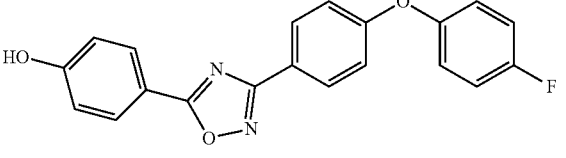 |
| | $^1$H NMR (600 MHz, CDCl$_3$) δ 4.13 (s, 2H), 6.71 (d, J = 8.5 Hz, 2H), 7.04-7.10 (m, 6H), 8.00 (d, J = 8.5 Hz, 2H), 8.11 (d, J = 8.5 Hz, 2H). |
| | HRMS (ESI) calcd for $C_{20}H_{15}FN_3O_2$ 348.1143, found 348.11563 $[MH]^+$ |
| 58a | 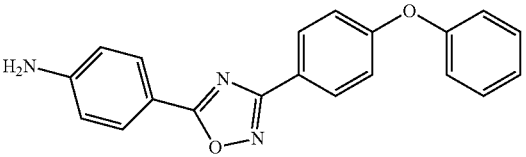 [SMILES: Nc1ccc(-c2nc(-c3ccc(Oc4ccccc4)cc3)no2)cc1] |

TABLE 2.1-continued

Spectral data of compounds of Schemes 2-4.

Compound
Number    Structure and data

¹H NMR    (600 MHz, acetone-d₆) δ 5.63 (br s, 2H), 6.84 (d, J = 8.8 Hz, 2H), 7.13 (d, J = 7.5 Hz, 2H), 7.14 (d, J = 8.8 Hz, 2H), 7.22 (t, J = 7.5 Hz, 1H), 7.45 (t, J = 7.5 Hz, 2H), 7.92 (d, J = 8.8 Hz, 2H), 8.13 (d, J = 8.8 Hz, 2H).
HRMS (ESI)    calcd for C₂₀H₁₅N₃O₂ 330.1237, found 330.1234 [MH]⁺

58b

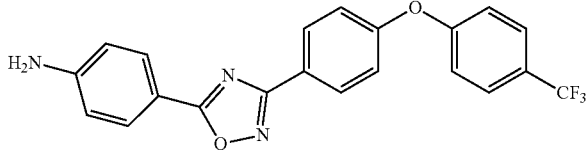

Lit.

58c

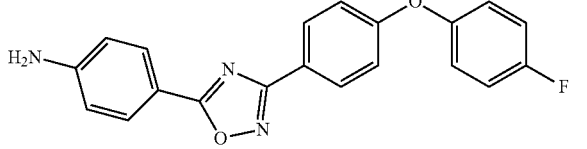

¹H NMR    (600 MHz, CDCl₃) δ 4.13 (s, 2H), 6.71 (d, J = 8.5 Hz, 2H), 7.04-7.10 (m, 6H), 8.00 (d, J = 8.5 Hz, 2H), 8.11 (d, J = 8.5 Hz, 2H).
¹⁹F NMR    (282 MHz, CDCl₃) δ -119.3
HRMS (ESI)    calcd for C₂₀H₁₅FN₃O₂ 348.1143, found 348.11563 [MH]⁺

59b

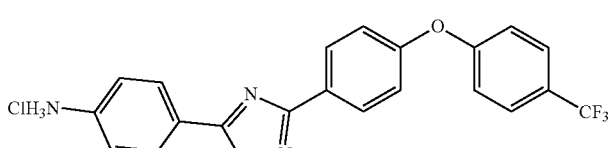

¹H NMR    (400 MHz, DMSO-d₆) δ 5.90 (br s, 3H), 6.81 (d, J = 8.6 Hz, 2H), 7.28 (d, J = 9.0 Hz, 2H), 7.29 (d, J = 8.6 Hz, 2H), 7.79 (d, J = 8.6 Hz, 2H), 7.88 (d, J = 8.6 Hz, 2H), 8.11 (d, J = 9.0 Hz, 2H).
HRMS (ESI)    calcd for C₂₁H₁₄F₃N₃O₂ 398.1111, found 398.1131 [MH]⁺

60a

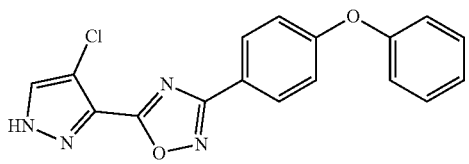 [SMILES: Clc1c[nH]nc1-c1nc(-c2ccc(Oc3ccccc3)cc2)no1]

¹H NMR    (400 MHz, DMSO-d₆) δ 7.16-7.20 (m, 4H), 7.26 (t, J = 7.4 Hz, 1H), 7.48 (t, J = 7.6 Hz, 2H), 8.11 (d, J = 8.4 Hz, 1H), 8.39 (s, 1H), 14.27 (s, 1H).
HRMS (ESI)    calcd for C₁₇H₁₁ClN₄O₂ 339.0643, found 339.0652 [MH]⁺

60b

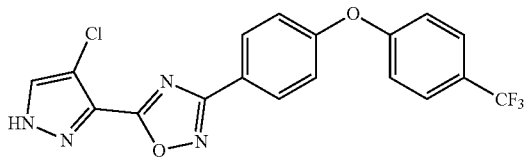 [SMILES: FC(F)(F)c1ccc(Oc2ccc(-c3noc(-c4n[nH]cc4Cl)n3)cc2)cc1]

¹H NMR    (400 MHz, CDCl₃) δ 7.16-7.19 (m, 4H), 7.66 (d, J = 8.8 Hz, 2H), 8.02 (s, 1H), 8.17-8.20 (m, 2H), 13.58 (br s, 1H).
HRMS (ESI)    calcd for C₁₈H₁₁ClF₃N₄O₂ 407.0517, found 407.0540 [MH]⁺

60c

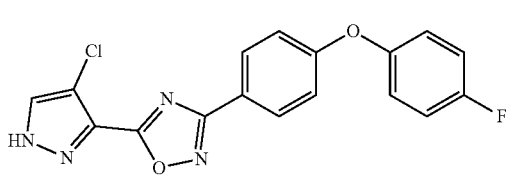 [SMILES: Fc1ccc(Oc2ccc(-c3noc(-c4n[nH]cc4Cl)n3)cc2)cc1]

TABLE 2.1-continued

Spectral data of compounds of Schemes 2-4.

Compound
Number    Structure and data

¹H NMR    (400 MHz, CDCl₃) δ 7.07-7.13 (m, 6H), 7.91 (s, 1H), 8.16 (d, J = 9.2 Hz, 2H).
HRMS (ESI) calcd for C₁₇H₁₁ClFN₄O₂ 357.0549, found 357.0544 [MH]⁺

61a

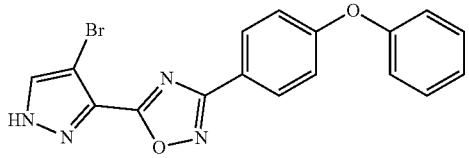 [SMILES: Brc1c[nH]nc1-c1nc(-c2ccc(Oc3ccccc3)cc2)no1]

¹H NMR    (400 MHz, CDCl₃) δ 7.10-7.14 (m, 4H), 7.20-7.22 (m, 1H), 7.39-7.44 (m, 2H), 7.97
          (s, 1H), 8.15-8.18 (m, 2H).
HRMS (ESI) calcd for C₁₇H₁₂BrN₄O₂ 383.0138, found 383.0120 [MH]⁺

61b

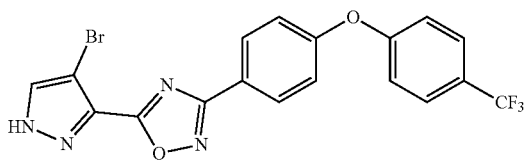 [SMILES: FC(F)(F)c1ccc(Oc2ccc(-c3noc(-c4n[nH]cc4Br)n3)cc2)cc1]

¹H NMR    (400 MHz, DMSO-d₆) δ 7.28-7.34 (m, 4H), 7.80 (d, J = 8.8 Hz, 2H), 8.14-8.16 (m,
          2H), 8.38 (s, 1H).
HRMS (ESI) calcd for C₁₈H₁₁BrF₃N₄O₂ 451.0012, found 450.9986 [MH]⁺

62a

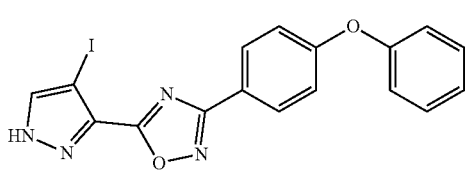 [SMILES: Ic1c[nH]nc1-c1nc(-c2ccc(Oc3ccccc3)cc2)no1]

¹H NMR    (400 MHz, CDCl₃) δ 7.11-7.15 (m, 4H), 7.18-7.22 (m, 1H), 7.39-7.44 (m, 2H), 8.05
          (s, 1H), 8.05-8.18 (m, 2H).
HRMS (ESI) calcd for C₁₇H₁₂IN₄O₂ 430.9999, found 430.9982 [MH]⁺

62b

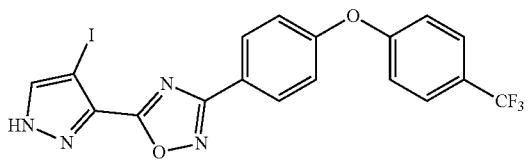 [SMILES: FC(F)(F)c1ccc(Oc2ccc(-c3noc(-c4n[nH]cc4I)n3)cc2)cc1]

¹H NMR    (400 MHz, DMSO-d₆) δ 7.29-7.36 (m, 4H), 7.80 (d, J = 8.8 Hz, 2H), 8.16 (d, J = 8.4
          Hz, 2H), 8.31 (s, 1H).
HRMS (ESI) calcd for C₁₈H₁₁F₃IN₄O₂ 498.9873, found 498.9879 [MH]⁺

63a

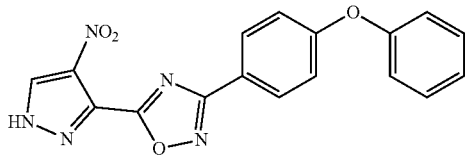 [SMILES: O=[N+]([O-])c1c[nH]nc1-c1nc(-c2ccc(Oc3ccccc3)cc2)no1]

¹H NMR    (400 MHz, CD₃OD) δ 7.12-7.14 (m, 4H), 7.20-7.24 (m, 1H), 7.41-7.45 (m, 2H),
          8.12-8.15 (m, 2H), 8.82 (s, 1H).
HRMS (ESI) calcd for C₁₇H₁₁N₅O₄ 372.0703, found 372.0707.

63c

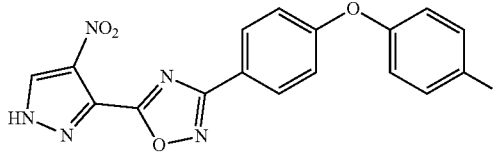

¹H NMR    (500 MHz, DMSO-d₆) δ 7.12-7.33 (m, 6H), 8.08 (t, J = 8.8 Hz, 2H), 9.2 (s, 1H).

TABLE 2.1-continued

Spectral data of compounds of Schemes 2-4.

Compound
Number  Structure and data

HRMS (ESI)  calcd for $C_{17}H_{11}FN_5O_4$ 368.0790, found 368.0790 [MH]$^+$

64a

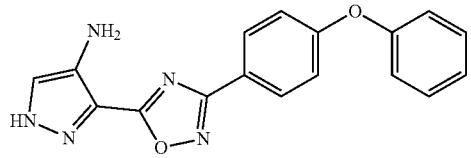

$^1$H NMR  (400 MHz, CDCl$_3$) δ 4.31 (br s, 2H), 7.09-7.12 (m, 4H), 7.18-7.22 (m, 1H), 7.39-7.43 (m, 3H), 8.12-8.14 (m, 2H).
HRMS (ESI)  calcd for $C_{17}H_{14}N_5O_2$ [M + H]$^+$ 320.1142, found 320.1158.

64c

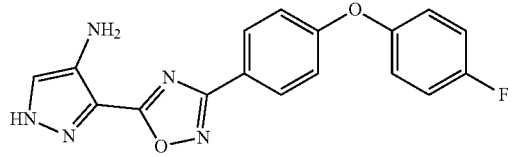 [SMILES: O=[N+]([O-])c1c[nH]nc1-c1nc(-c2ccc(Oc3ccc(F)cc3)cc2)no1]

$^1$H NMR  (400 MHz, CDCl$_3$) δ 6.79 (d, J = 8.8 Hz, 2H), 6.99-7.09 (m, 4H), 7.21 (s, 1H), 7.76 (d, J = 8.8 Hz, 2H).
HRMS (ESI)  calcd for $C_{17}H_{13}FN_5O_2$ 338.1048, found 338.1038 [MH]$^+$ 65a

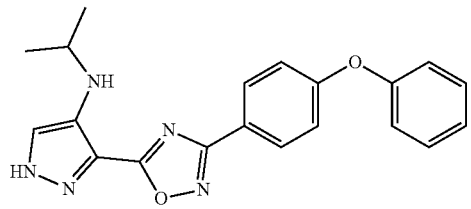 [SMILES: CC(C)Nc1c[nH]nc1-c1nc(-c2ccc(Oc3ccccc3)cc2)no1]

$^1$H NMR  (400 MHz, CDCl$_3$) δ 1.32 (s, 3H), 1.33 (s, 3H), 3.48-3.55 (m, 1H), 7.10-7.12 (m, 4H), 7.18-7.21 (m, 1H), 7.38-7.43 (m, 2H), 7.49 (s, 1H), 8.12-8.15 (m, 2H)
HRMS (ESI)  calcd for $C_{20}H_{20}N_5O_2$ [M + H]$^+$ 362.1612, found 362.1630.

67b

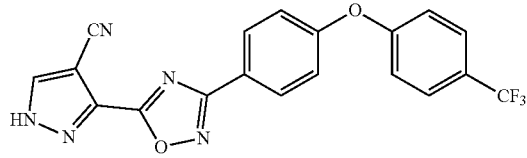 [SMILES: N#Cc1c[nH]nc1-c1nc(-c2ccc(Oc3ccc(C(F)(F)F)cc3)cc2)no1]

$^1$H NMR  (400 MHz, CDCl$_3$) δ 7.14-7.19 (m, 4H), 7.63-7.66 (m, 2H), 8.21-8.23 (m, 2H), 8.33 (s, 1H).
HRMS (ESI)  calcd for $C_{19}H_{11}F_3N_5O_2$ 398.0859, found 398.0824 [MH]$^+$ 69b

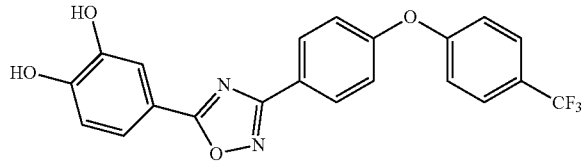 [SMILES: Oc1ccc(-c2nc(-c3ccc(Oc4ccc(C(F)(F)F)cc4)cc3)no2)cc1O]

$^1$H NMR  (400 MHz, DMSO-d$_6$) δ 6.96 (d, J = 8.4 Hz, 1H), 7.16-7.18 (m, 2H), 7.27-7.29 (m, 2H), 7.51-7.55 (m, 2H), 7.99-8.01 (m, 2H), 8.10-8.12 (m, 2H).
HRMS (ESI)  calcd for $C_{21}H_{13}F_3N_2O_4$ 415.0900, found 415.0900 [MH]$^+$ 69c

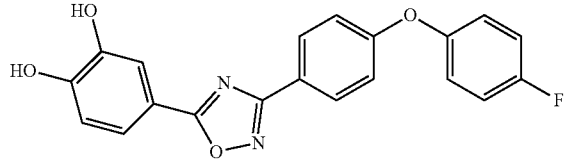 [SMILES: Oc1ccc(-c2nc(-c3ccc(Oc4ccc(F)cc4)cc3)no2)cc1O]

TABLE 2.1-continued

Spectral data of compounds of Schemes 2-4.

Compound Number — Structure and data

¹H NMR (400 MHz, DMSO-d$_6$) δ 6.95 (d, J = 8.4 Hz, 1H), 7.11-7.14 (m, 2H), 7.19-7.23 (m, 2H), 7.28-7.32 (m, 2H), 7.50-7.54 (m, 2H), 8.04-8.06 (m, 2H), 9.68 (br s, 1H), 10.06 (br s, 1H).
HRMS (ESI) calcd for C$_{20}$H$_{14}$FN$_2$O$_4$ 365.0932, found 365.0929 [MH]$^+$ 70a ¹H NMR (500 MHz, CDCl$_3$) δ 7.07-7.11 (m, 3H), 7.14 (t, J = 8.5 Hz, 1H), 7.18 (t, J = 7.4 Hz, 1H), 7.37-7.41 (m, 3H), 7.89-7.94 (m, 2H), 8.11 (d, J = 8.8 Hz, 2H).
HRMS (ESI) calcd for C$_{20}$H$_{14}$FN$_2$O$_3$ 349.0983, found 349.0974 [MH]$^+$ 70c ¹H NMR (500 MHz, CD$_3$OD) δ 7.03 (d, J = 9.0 Hz, 2H), 7.06-7.11 (m, 3H), 7.13-7.17 (m, 2H), 7.81-7.84 (m, 2H), 8.04 (d, J = 9.0 Hz, 2H).
¹⁹F NMR (282 MHz, CD$_3$OD) δ −121.2, −137.9.
HRMS (ESI) calcd for C$_{20}$H$_{13}$F$_2$N$_2$O$_3$ 367.0889, found 367.0889 [MH]$^+$ 71c ¹H NMR (500 MHz, CD$_3$OD) δ 7.09 (d, J = 8.5 Hz, 2H), 7.13-7.17 (m, 4H), 7.78 (d, J = 8.5 Hz, 2H), 8.10 (d, J = 9.0 Hz, 2H).
¹⁹F NMR (282 MHz, CD$_3$OD) δ −121.2, −134.0.
HRMS (ESI) calcd for C$_{20}$H$_{12}$F$_3$N$_2$O$_3$ 385.0795, found 385.0770 [MH]$^+$ 72a ¹H NMR (500 MHz, CDCl$_3$) δ 4.23 (br s, 2H), 6.85 (t, J = 8.6 Hz, 1H), 7.07-7.10 (m, 4H), 7.17 (t, J = 7.4 Hz, 1H), 7.38 (dd, J = 8.6, 7.6 Hz, 2H), 7.80-7.84 (m, 2H), 8.10 (d, J = 9.0 Hz, 2H).
¹⁹F NMR (282 MHz, CDCl$_3$) δ −135.26 (dd, J = 11.0, 8.6 Hz).
HRMS (ESI) calcd for C$_{20}$H$_{15}$FN$_3$O$_2$ 348.1143, 348.1117 found [MH]$^+$ 72b ¹H NMR (500 MHz, CDCl$_3$) δ 4.25 (br s, 2H), 6.85 (t, J = 8.6 Hz, 1H), 7.12-7.16 (m, 4H), 7.62 (d, J = 8.6 Hz, 2H), 7.80-7.84 (m, 2H), 8.16 (d, J = 8.8 Hz, 2H).
¹⁹F NMR (282 MHz, CDCl$_3$) δ −135.22 (dd, 1F, J = 12.2, 8.6 Hz), −62.21 (s, 3F).

TABLE 2.1-continued

Spectral data of compounds of Schemes 2-4.

Compound Number | Structure and data

73b

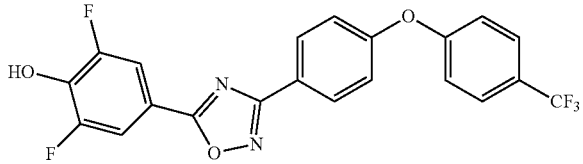 [SMILES: Oc1c(F)cc(-c2nc(-c3ccc(Oc4ccc(C(F)(F)F)cc4)cc3)no2)cc1F]

¹H NMR (400 MHz, CDCl₃) δ 7.13-7.17 (m, 4H), 7.64 (d, J = 8.5 Hz, 2H), 7.78 (dd, J = 6.7, 1.5 Hz, 2H), 8.16 (d, J = 9.0 Hz, 2H).
HRMS (ESI) calcd for $C_{21}H_{11}F_5N_2O_3$ 435.0763, found 435.0735 [MH]⁺

74a

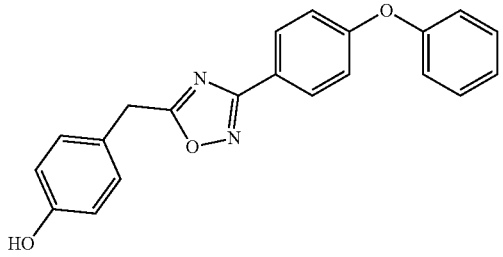 [SMILES: Oc1ccc(Cc2nc(-c3ccc(Oc4ccccc4)cc3)no2)cc1]

¹H NMR (400 MHz, CDCl₃) δ 4.18 (s, 2H), 6.36 (s, 1H), 6.74 (d, J = 8.6 Hz, 2H), 7.01-7.06 (m, 4H), 7.12-7.18 (m, 3H), 7.36 (m, 2H), 8.00 (d, 2H).
HRMS (ESI) calcd for $C_{21}H_{16}N_2O_3$ 345.1234, found 345.1211 [MH]⁺

75a

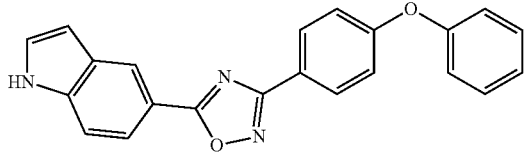 [SMILES: c1ccc(Oc2ccc(-c3noc(-c4ccc5[nH]ccc5c4)n3)cc2)cc1]

¹H NMR (400 MHz, DMSO-d₆) δ 6.68 (m, 1H), 7.14-7.18 (m, 4H), 7.24 (tt, J = 7.5, 1.2 Hz), 7.47 (m, 2H), 7.55 (t, J = 2.8 Hz, 1H), 7.63 (d, J = 8.5 Hz, 1H), 7.91 (dd J = 8.5, 1.7 Hz), 8.11 (d, J = 8.9 Hz), 8.46 (m, 1H), 11.64 (s, 1H).
HRMS (ESI) calcd for $C_{22}H_{15}N_3O_2$ 354.1237, found 354.1273 [MH]⁺

75b

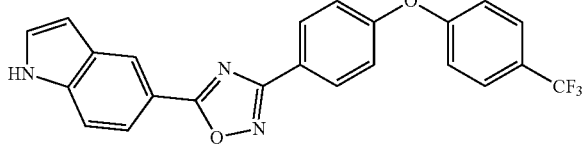

¹H NMR (400 MHz, CDCl₃) δ 6.71 (m, 1H), 7.13 (d, J = 8.7 Hz, 2H), 7.16 (d, J = 8.9 Hz, 2H), 7.32 (d, J = 8.7 Hz, 2H), 7.52 (d, J = 8.6 Hz, 1H), 7.63 (d, J = 8.9 Hz, 2H), 8.06 (d, d, J = 8.6, 1.61 Hz, 1H), 8.22 (d, J = 8.9 Hz, 2H), 8.52 (s, 1H), 8.57 (t, J = 0.8 Hz, 1H).
¹⁹F NMR (376 MHz, CDCl₃) δ 99.90 (s, 3F).
HRMS (ESI) calcd for $C_{23}H_{14}F_3N_3O_2$ 422.1111, found 422.1146 [MH]⁺

75c

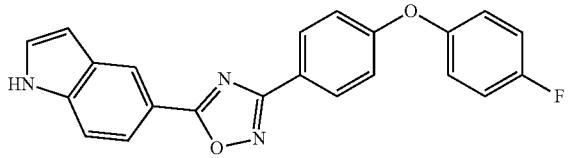 [SMILES: Fc1ccc(Oc2ccc(-c3noc(-c4ccc5[nH]ccc5c4)n3)cc2)cc1]

¹H NMR (400 MHz, DMSO-d₆) δ 6.68 (m, 1H), 7.15 (d, J = 8.8 Hz, 2H), 7.12-7.16 (m, 2H), 7.29-7.33 (m, 2H), 7.55 (t, J = 2.8 Hz, 1H), 7.66 (d, J = 8.5 Hz, 1H), 7.91 (dd J = 8.5, 1.6 Hz), 8.10 (d, J = 8.8 Hz, 2H), 8.46 (m, 1H), 11.64 (s, 1H).
HRMS (ESI) calcd for $C_{22}H_{14}FN_3O_2$ 371.1143, found 372.1166 [MH]⁺

TABLE 2.1-continued

Spectral data of compounds of Schemes 2-4.

| Compound Number | Structure and data |
|---|---|ах

76c

¹H NMR (400 MHz, DMSO-d₆) δ 7.12-7.14 (m, 2H), 7.19-7.22 (m, 2H), 7.28-7.32 (m, 2H), 7.98 (s, 1H), 8.04-8.06 (m, 2H), 8.23 (s, 1H), 12.98 (s, 1H).
HRMS (ESI) calcd for $C_{17}H_{12}FN_4O_2$ 323.0939, found 323.0948 [MH]⁺

77b

¹H NMR (400 MHz, DMSO-d₆) δ 7.29-7.31 (m, 4H), 7.81 (d, J = 8.8 Hz, 2H), 8.13 (d, J = 8.8 Hz, 2H), 8.78 (d, J = 2.4 Hz, 1H), 8.90 (d, J = 2.4 Hz, 1H), 13.76 (br s, 1H);
HRMS (ESI) calcd for $C_{20}H_{12}F_3N_4O_5$ 445.0754, found 445.0742 [MH]⁺

77c

¹H NMR (400 MHz, DMSO-d₆) δ 7.09-7.33 (m, 6H), 8.03-8.08 (m, 2H), 8.73-8.90 (m, 2H), 13.73 (br s, 1H).
HRMS (ESI) calcd for $C_{19}H_{12}FN_4O_5$ 395.0786, found 395.0779 [MH]⁺

78b

¹H NMR (400 MHz, CDCl₃) δ 7.14-7.18 (m, 4H), 7.64-7.67 (m, 3H), 7.91-7.92 (m, 1H), 8.11-8.15 (m, 2H), 9.66 (br, 1H).
HRMS (ESI) calcd for $C_{19}H_{11}F_3N_4O_4$ 417.0805, found 417.0805 [MH]⁺

78c

¹H NMR (400 MHz, CDCl₃) δ 7.05-7.11 (m, 6H), 7.62-7.63 (m, 1H), 7.89-7.91 (m, 1H), 8.04-8.07 (m, 2H), 9.66 (br, 1H).
HRMS (ESI) calcd for $C_{20}H_{11}FN_4O_4Na$ 389.0657, found 389.0654 [MNa]⁺

79a

TABLE 2.1-continued

Spectral data of compounds of Schemes 2-4.

Compound Number | Structure and data

¹H NMR (600 MHz, CDCl₃) δ 4.12 (br s, 2H), 4.65-4.67 (m, 2H), 5.36 (ddd, J = 10.9, 3.2, 1.8 Hz, 1H), 5.72 (ddd, J = 17.3, 3.5, 1.8 Hz, 1H), 6.12 (ddd, J = 17.3, 10.9, 4.7 Hz, 1H), 6.27 (d, J = 2.2 Hz, 1H), 6.37 (dd, J = 8.5, 2.2 Hz, 1H), 7.07-7.09 (m, 4H), 7.17 (dt, J = 7.5, 1.2 Hz, 1H), 7.37-7.40 (m, 2H), 8.00 (d, J = 8.5 Hz, 1H), 8.13 (d, J = 8.8 Hz, 2H).
HRMS (ESI) calcd for C₂₃H₁₉N₃NaO₃ 408.1319, found 408.1319 [MNa]⁺

80a

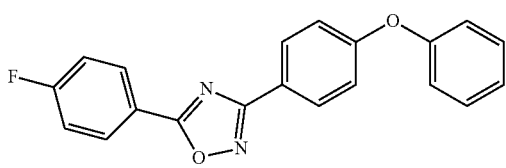 [SMILES: Fc1ccc(-c2nc(-c3ccc(Oc4ccccc4)cc3)no2)cc1]

¹H NMR (600 MHz, acetone-d₆) δ 7.12-7.16 (m, 2H), 7.15 (d, J = 9.0 Hz, 2H), 7.23 (tt, J = 7.4, 1.0 Hz, 1H), 7.42-7.47 (m, 4H), 8.14 (d, J = 9.0 Hz, 2H), 8.29 (dd, J = 8.8, 5.3 Hz, 2H).
HRMS (ESI) calcd for C₂₀H₁₄FN₂O₂ 333.1034, found 333.1004 [MH]⁺

80b

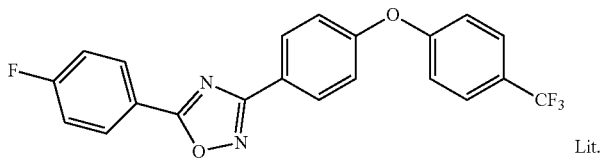 [SMILES: Fc1ccc(-c2nc(-c3ccc(Oc4ccc(C(F)(F)F)cc4)cc3)no2)cc1]

Lit.

81b

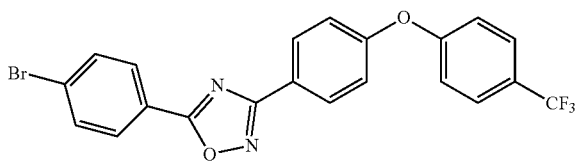 [SMILES: FC(F)(F)c1ccc(Oc2ccc(-c3noc(-c4ccc(Br)cc4)n3)cc2)cc1]

¹H NMR (600 MHz, acetone-d₆) δ 7.28-7.30 (m, 4H), 7.79 (d, J = 8.2 Hz, 2H), 7.86 (d, J = 8.2 Hz, 2H), 8.15 (d, J = 8.8 Hz, 2H), 8.20 (d, J = 8.8 Hz, 2H).
HRMS (ESI) calcd for C₂₁H₁₃BrF₃N₂O₂ 461.0107, found 461.0091 [MH]⁺

81c

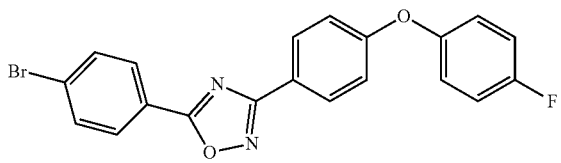 [SMILES: Fc1ccc(Oc2ccc(-c3noc(-c4ccc(Br)cc4)n3)cc2)cc1]

¹H NMR (400 MHz, CDCl₃) δ 7.00-7.05 (m, 6H), 7.65 (d, J = 8.4 Hz, 2H), 8.01-8.08 (m, 4H).
HRMS (ESI) calcd for C₂₀H₁₂BrFN₂O₂ 411.0139, found 411.0139 [MH]⁺

83b

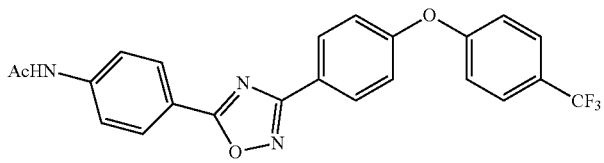 [SMILES: CC(=O)Nc1ccc(-c2nc(-c3ccc(Oc4ccc(C(F)(F)F)cc4)cc3)no2)cc1]

¹H NMR (600 MHz, acetone-d₆) δ 2.15 (s, 3H, CH₃), 7.29-7.32 (m, 4H, ArH),
HRMS (ESI) calcd for C₂₃H₁₇F₃N₃O₃ 440.1217, found 440.1233 [MH]⁺

TABLE 2.1-continued

Spectral data of compounds of Schemes 2-4.

Compound Number | Structure and data

85c

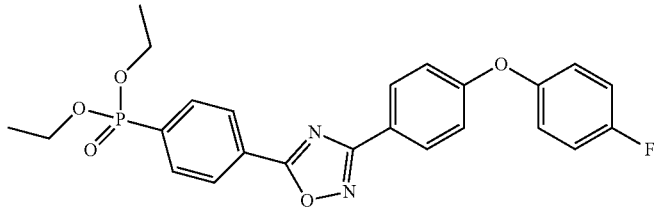 [SMILES: CCOP(=O)(OCC)c1ccc(-c2nc(-c3ccc(Oc4ccc(F)cc4)cc3)no2)cc1]

¹H NMR (400 MHz, CDCl₃) δ 1.35 (t, J = 7.2 Hz, 6H), 4.10-4.19 (m, 4H), 7.04-7.09 (m, 6H), 7.97-8.02 (m, 2H), 8.10-8.14 (m, 2H), 8.28-8.31 (m, 2H).
HRMS (ESI) calcd for $C_{24}H_{23}FN_2O_5P$ 469.1323, found 469.1324 [MH]⁺

86b

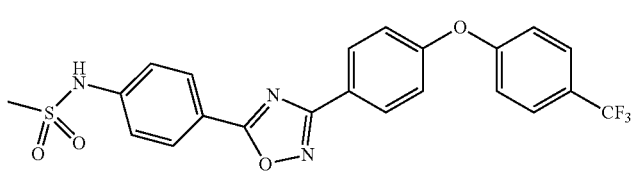 [SMILES: CS(=O)(=O)Nc1ccc(-c2nc(-c3ccc(Oc4ccc(C(F)(F)F)cc4)cc3)no2)cc1]

¹H NMR (600 MHz, CDCl₃) δ 3.14 (s, 3H), 6.76 (s, 1H), 7.14 (d, J = 8.5 Hz, 2H), 7.16 (d, J = 8.8 Hz, 2H), 7.37 (d, J = 8.8 Hz, 2H), 7.64 (d, J = 8.5 Hz, 2H), 8.18 (d, J = 8.8 Hz, 2H), 8.22 (d, J = 8.8 Hz, 2H).
HRMS (ESI) calcd for $C_{22}H_{17}F_3N_3O_4S$ 476.0886, found 476.0909 [MH]⁺

87b

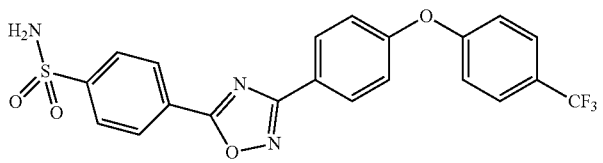 [SMILES: NS(=O)(=O)c1ccc(-c2nc(-c3ccc(Oc4ccc(C(F)(F)F)cc4)cc3)no2)cc1]

¹H NMR (400 MHz, DMSO-d₆) δ 7.30-7.34 (m, 4H), 7.66 (s, 2H), 7.82 (d, J = 9.2 Hz, 2H), 8.08 (d, J = 8.4 Hz, 2H), 8.16-8.18 (m, 2H), 8.40 (d, J = 8.0 Hz, 2H).
HRMS (ESI) calcd for $C_{21}H_{15}F_3N_3O_4S$ 462.0730, found 462.0752 [MH]⁺

87c

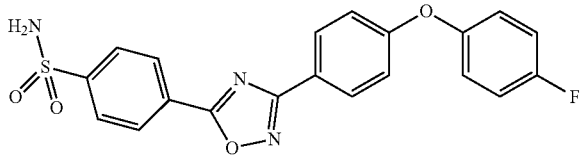 [SMILES: NS(=O)(=O)c1ccc(-c2nc(-c3ccc(Oc4ccc(F)cc4)cc3)no2)cc1]

¹H NMR (400 MHz, CD₃OD) δ 7.06-7.18 (m, 6H), 8.10-8.12 (m, 4H), 8.35 (d, J = 6.8 Hz, 2H).
HRMS (ESI) calcd for $C_{20}H_{15}FN_3O_4S$ 412.0762, found 412.0755 [MH]⁺

88c

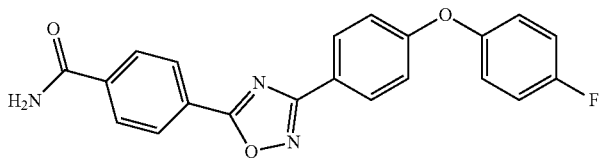 [SMILES: NC(=O)c1ccc(-c2nc(-c3ccc(Oc4ccc(F)cc4)cc3)no2)cc1]

¹H NMR (500 MHz, DMSO-d₆) δ 6.41 (s, 2H), 7.16 (d, J = 8.8 Hz, 2H), 7.21-7.24 (m, 2H), 7.30-7.33 (m, 2H), 8.10-8.13 (m, 4H), 8.26 (d, J = 8.2 Hz, 2H).
HRMS (ESI) calcd for $C_{21}H_{15}FN_3O_3$ 376.1092, found 376.1091 [MH]⁺

89c

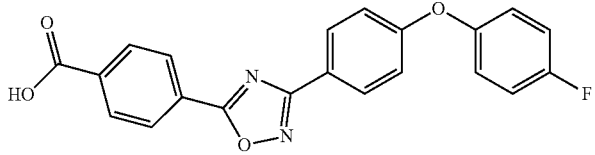 [SMILES: O=C(O)c1ccc(-c2nc(-c3ccc(Oc4ccc(F)cc4)cc3)no2)cc1]

¹H NMR (500 MHz, DMSO-d₆) δ 7.15 (d, J = 9.0 Hz, 2H), 7.13 (dd, J = 8.9, 4.5 Hz, 2H), 7.31

TABLE 2.1-continued

Spectral data of compounds of Schemes 2-4.

| Compound Number | Structure and data |
| --- | --- |

(t, J = 8.9 Hz, 2H), 8.10 (d, J = 9.0 Hz, 2H), 8.18 (d, J = 8.8 Hz, 2H), 8.30 (d, J = 8.8 Hz, 2H).
¹⁹F NMR (282 MHz, DMSO-d₆): δ −118.8.
HRMS (ESI) calcd for C$_{21}$H$_{12}$FN$_2$Na$_2$O$_4$ 421.0571, found 421.0572 [MH]⁺

90c

¹H NMR (500 MHz, CDCl₃) δ 3.98 (s, 3H), 7.05-7.11 (m, 6H), 8.14 (d, J = 9.0 Hz, 2H), 8.22 (d, J = 8.4 Hz, 2H), 8.29 (d, J = 8.4 Hz, 2H).
¹⁹F NMR (282 MHz, CDCl₃): δ −119.0.
HRMS (ESI) calcd for C$_{22}$H$_{16}$FN$_2$O$_4$ 391.1089, found 391.1099 [MH]⁺

91c

¹H NMR (400 MHz, CDCl₃) δ 7.06-7.13 (m, 6H), 7.36-7.39 (m, 1H), 8.12-8.15 (m, 2H), 8.40-8.42 (m, 1H), 9.00-9.01 (m, 1H), 10.95 (s, 1H).
HRMS (ESI) calcd for C$_{20}$H$_{13}$FN$_3$O$_5$ 394.0834, found 394.0834 [MH]⁺

92c

¹H NMR (400 MHz, DMSO-d₆) δ 5.02 (br, 2H), 6.84 (d, J = 8.4 Hz, 1H), 7.12-7.14 (m, 2H), 7.19-7.22 (m, 2H), 7.27-7.33 (m, 3H), 7.42 (d, J = 2.0 Hz, 1H), 8.03-8.06 (m, 2H).
HRMS (ESI) calcd for C$_{20}$H$_{15}$FN$_3$O$_3$ 364.1097, found 364.1099 [MH]⁺

94a

¹H NMR (600 MHz, DMSO-d₆) δ 3.98 (s, 3H), 4.30 (s, 2H), 6.77 (d, J = 8.2 Hz, 1H), 7.08-7.11 (m, 4H), 7.17 (tt, J = 7.5, 1.0 Hz, 1H), 7.39 (dd, J = 7.5, 1.0 Hz, 2H), 7.58 (d, J = 1.8 Hz, 1H), 7.70 (dd, J = 8.2, 1.8 Hz, 1H), 8.12 (d, J = 9.1 Hz, 2H).
HRMS (ESI) calcd for C$_{21}$H$_{18}$N$_3$O$_3$ 360.1343, found 360.1362 [MH]⁺

95a

¹H NMR (400 MHz, DMSO-d₆) δ 7.12 (m, 1H) 7.14-7.19 (m, 4H), 7.25 (tt, J = 7.5, 1.1 Hz, 1H), 7.45-7.50 (m, 3H), 7.56 (m, 1H), 7.62 (m, 1H), 8.09 (d, J = 8.9 Hz), 10.10 (s, H).
HRMS (ESI) calcd for C$_{20}$H$_{14}$N$_2$O$_3$ 331.1077, found 331.1104 [MH]⁺

TABLE 2.1-continued

Spectral data of compounds of Schemes 2-4.

Compound Number | Structure and data

96a

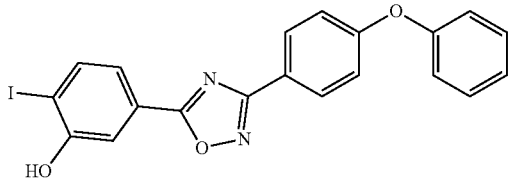 [SMILES: Oc1cc(-c2nc(-c3ccc(Oc4ccccc4)cc3)no2)ccc1I]

¹H NMR (400 MHz, DMSO-d₆) δ 7.14-7.18 (m, 4H), 7.25 (t, d, J = 7.3, 0.8 Hz, 1H), 7.38 (dd, J = 8.2, 1.9 Hz, 1H), 7.48 (t, J = 7.7 Hz, 2H), 7.64 (d, J = 1.9 Hz, 1H), 7.98 (td, J = 8.2, 1H), 8.08 (d, J = 8.8 Hz, 2H).
HRMS (ESI) calcd for $C_{20}H_{13}IN_2O_3$ 457.0044, found 457.0082 [MH]⁺

97a

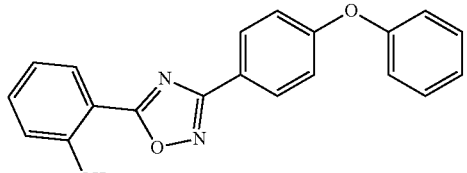

¹H NMR (400 MHz, CDCl₃) δ 7.05 (m, 1H), 7.09-7.14 (m, 4H), 7.15 (m, 1H), 7.20 (tt, J = 7.4, 1.1 Hz, 1H), 7.38-7.43 (m, 2H), 7.53 (m, 1H), 8.00 (dd, J = 8.0, 1.7 Hz, 1H), 8.09 (d, J = 9.0 Hz), 10.53 (s, 1H).
HRMS (ESI) calcd for $C_{20}H_{14}N_2O_3$ 323.1077, found 323.1105 [MH]⁺

98a

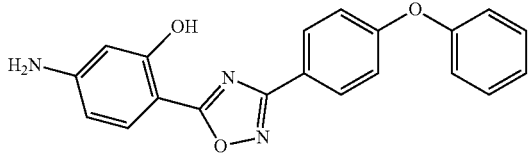 [SMILES: Nc1ccc(-c2nc(-c3ccc(Oc4ccccc4)cc3)no2)c(O)c1]

¹H NMR (600 MHz, CDCl₃) δ 4.17 (s, 2H), 6.31-6.33 (m, 2H), 7.08-7.10 (m, 4H), 7.19 (t, J = 7.4 Hz, 1H), 7.40 (dd, J = 7.4, 1.2 Hz, 2H), 7.76 (d, J = 8.8 Hz, 1H), 8.06 (d, J = 8.8 Hz, 2H), 10.59 (s, 1H).
HRMS (ESI) calcd for $C_{20}H_{16}N_3O_3$ 346.1186, found 346.1196 [MH]⁺

99a

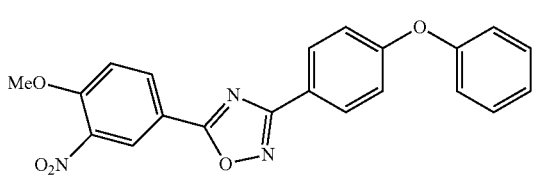 [SMILES: COc1ccc(-c2nc(-c3ccc(Oc4ccccc4)cc3)no2)cc1[N+](=O)[O-]]

¹H NMR (500 MHz, CDCl3) δ 4.08 (s, 3H), 7.08-7.11 (m, 2H), 7.10 (d, J = 9.0 Hz, 2H), 7.19 (tt, J = 7.5, 1.1 Hz, 1H), 7.27 (d, J = 8.8 Hz, 1H), 7.40 (dd, J = 7.4, 1.1 Hz, 2H), 8.12 (d, J = 9.0 Hz, 2H), 8.37 (dd, J = 8.8, 2.2 Hz, 1H), 8.71 (d, J = 2.2 Hz, 1H).
HRMS (ESI) calcd for $C_{21}H_{16}N_3O_5$ 390.1084, found 390.1068 [MH]⁺

99b

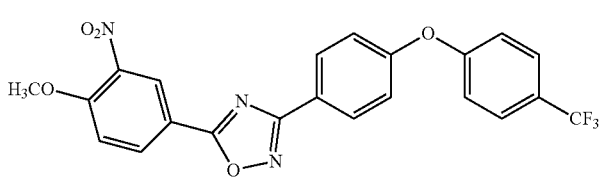 [SMILES: COc1ccc(-c2nc(-c3ccc(Oc4ccc(C(F)(F)F)cc4)cc3)no2)cc1[N+](=O)[O-]]

¹H NMR (400 MHz, CDCl₃) δ 4.09 (s, 3H), 7.14-7.19 (m, 4H), 7.27-7.29 (m, 1H), 7.64-7.66 (m, 2H), 8.17-8.20 (m, 2H), 8.38 (dd, J = 2.0 Hz, 1H), 8.72 (d, J = 2.4 Hz, 1H).
HRMS (ESI) calcd for $C_{22}H_{15}F_3N_3O_5$ 458.0958, found 458.0960 [MH]⁺

TABLE 2.1-continued

Spectral data of compounds of Schemes 2-4.

Compound Number | Structure and data

99c 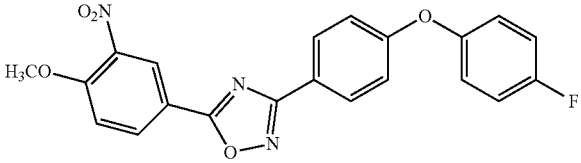 [SMILES: COc1ccc(-c2nc(-c3ccc(Oc4ccc(F)cc4)cc3)no2)cc1[N+](=O)[O-]]

¹H NMR (400 MHz, CDCl₃) δ 4.13 (s, 3H), 7.09-7.17 (m, 5H), 7.30-7.33 (m, 2H), 8.15-8.18 (m, 2H), 8.41-8.43 (m, 1H), 8.76 (d, J = 2.0 Hz, 1H).
HRMS (ESI) calcd for $C_{21}H_{14}FN_3NaO_5$ 430.0810, found 430.0840 [MNa]⁺

100a 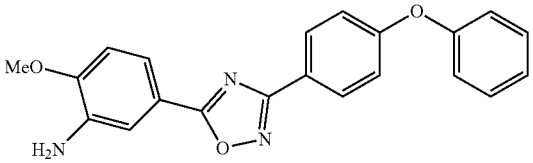

¹H NMR (600 MHz, DMSO-d₆) δ 3.88 (s, 3H), 7.02 (d, J = 8.5 Hz, 1H), 7.14-7.17 (m, 4H), 7.24 (tt, J = 7.4, 1.1 Hz, 1H), 7.39-7.41 (m, 1H), 7.45-7.49 (m, 3H), 8.06 (d, 2H, J = 8.8 Hz).
HRMS (ESI) calcd for $C_{21}H_{18}N_3O_3$ 360.1343, found 360.1355 [MH]⁺

101b 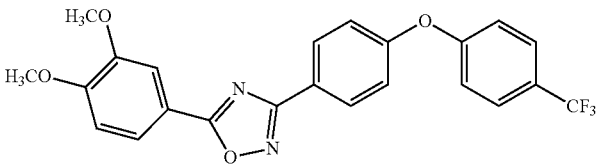 [SMILES: COc1ccc(-c2nc(-c3ccc(Oc4ccc(C(F)(F)F)cc4)cc3)no2)cc1OC]

¹H NMR (400 MHz, CDCl₃) δ 3.99 (s, 3H), 4.03 (s, 3H), 7.02 (d, J = 8.8 Hz, 1H), 7.13-7.19 (m, 4H), 7.62-7.65 (m, 2H), 7.70 (d, J = 2.0 Hz, 1H), 7.85 (dd, J = 2.0 Hz, 1H), 8.19-8.21 (m, 2H).
HRMS (ESI) calcd for $C_{23}H_{18}F_3N_2O_4$ 443.1213, found 443.1235 [MH]⁺

101c 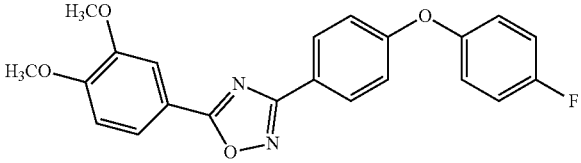 [SMILES: COc1ccc(-c2nc(-c3ccc(Oc4ccc(F)cc4)cc3)no2)cc1OC]

¹H NMR (400 MHz, CDCl₃) δ 3.96 (s, 3H), 3.99 (s, 3H), 6.98 (d, J = 8.4 Hz, 1H), 7.03-7.10 (m, 5H), 7.67 (d, J = 2.0 Hz, 1H), 7.82 (dd, J = 2.0 Hz, 1H), 8.10-8.13 (m, 2H).
HRMS (ESI) calcd for $C_{22}H_{18}FN_2O_4$ 393.1245, found 393.1264 [MH]⁺

102b 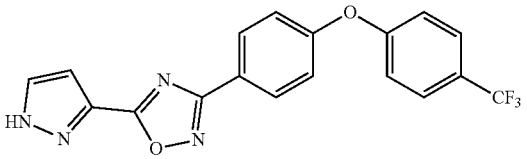 [SMILES: FC(F)(F)c1ccc(Oc2ccc(-c3noc(-c4cc[nH]n4)n3)cc2)cc1]

¹H NMR (400 MHz, CDCl₃) δ 7.15-7.19 (m, 5H), 7.65 (d, J = 8.8, 2H), 8.04 (d, J = 2.4 Hz, 1H), 8.20-8.22 (m, 2H).
HRMS (ESI) calcd for $C_{18}H_{12}F_3N_4O_2$ 373.0907, found 373.0907 [MH]⁺

102c 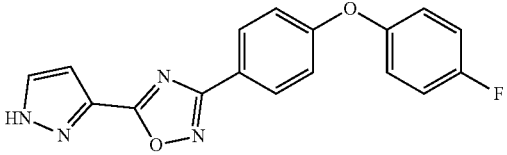 [SMILES: Fc1ccc(Oc2ccc(-c3noc(-c4cc[nH]n4)n3)cc2)cc1]

¹H NMR (400 MHz, CD₃OD) δ 7.07-7.16 (m, 7H), 7.90 (s, 1H), 8.09-8.12 (m, 2H).

TABLE 2.1-continued

Spectral data of compounds of Schemes 2-4.

Compound Number — Structure and data

HRMS (ESI) calcd for $C_{17}H_{12}FN_4O_2$ 323.0939, found 323.0941 $[MH]^+$

103b

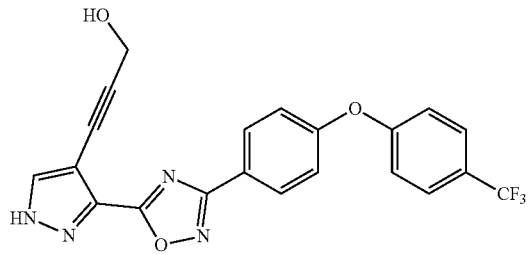 [SMILES: OCC#Cc1c[nH]nc1-c1nc(-c2ccc(Oc3ccc(C(F)(F)F)cc3)cc2)no1]

$^1$H NMR (400 MHz, DMSO-$d_6$) δ 4.37 (d, J = 6.0 Hz, 2H), 5.38 (t, J = 6.0 Hz, 1H), 7.29-7.33 (m, 4H), 7.81 (d, J = 8.4 Hz, 2H), 8.16 (d, J = 8.4 Hz, 2H), 8.37 (s, 1H).
HRMS (ESI) calcd for $C_{21}H_{14}F_3N_4O_3$ 427.1013, found 427.1013 $[MH]^+$ 104b

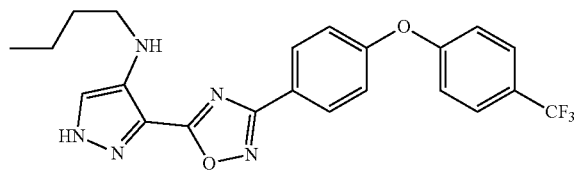 [SMILES: CCCCNc1c[nH]nc1-c1nc(-c2ccc(Oc3ccc(C(F)(F)F)cc3)cc2)no1]

$^1$H NMR (400 MHz, CDCl$_3$) δ 0.98-1.01 (m, 3H), 1.44-1.50 (m, 2H), 1.67-1.75 (m, 2H), 3.20 (t, J = 8.0 Hz, 2H), 4.81 (br s, 1H), 7.14-7.18 (m, 4H), 7.43 (s, 1H), 7.64 (d, J = 8.0 Hz, 2H), 8.15-8.19 (m, 2H).
HRMS (ESI) calcd for $C_{22}H_{21}F_3N_5O_2$ 444.1642, found 444.1668 $[MH]^+$ 105b

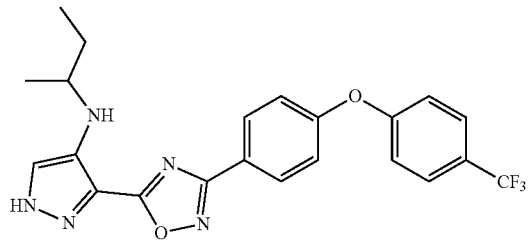 [SMILES: CCC(C)Nc1c[nH]nc1-c1nc(-c2ccc(Oc3ccc(C(F)(F)F)cc3)cc2)no1]

$^1$H NMR (400 MHz, CDCl$_3$) δ 1.02 (t, J = 7.2 Hz, 3H), 1.29 (d, J = 6.4 Hz, 4H), 1.58-1.76 (m, 2H), 3.28-3.33 (m, 1H), 7.14-7.18 (m, 4H), 7.45 (s, 1H), 7.64 (d, J = 8.4 Hz, 2H), 8.17-8.19 (m, 2H).
HRMS (ESI) calcd for $C_{22}H_{21}F_3N_5O_2$ 444.1642, found 444.1647 $[MH]^+$ 106b

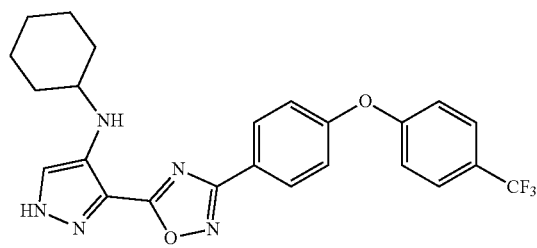 [SMILES: FC(F)(F)c1ccc(Oc2ccc(-c3noc(-c4n[nH]cc4NC4CCCCC4)n3)cc2)cc1]

$^1$H NMR (400 MHz, CDCl$_3$) δ 1.36-1.45 (m, 5H), 1.64-1.82 (m, 3H), 2.10 (d, J = 10.4 Hz, 2H), 3.18 (br s, 1H), 4.90 (d, J = 3.2 Hz, 1H), 7.14-7.19 (m, 3H), 7.37 (s, 1H), 7.63-7.65 (m, 2H), 8.16-8.20 (m, 2H).
HRMS (ESI) calcd for $C_{24}H_{23}F_3N_5O_2$ 470.1798, found 470.1812 $[MH]^+$ TABLE 2.1-continued Spectral data of compounds of Schemes 2-4.

Compound Number | Structure and data

107b

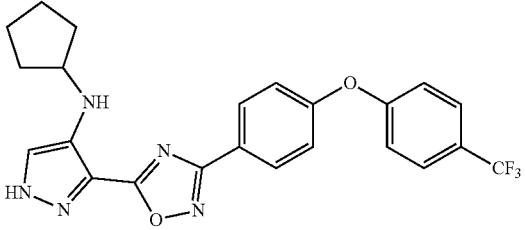 [SMILES: FC(F)(F)c1ccc(Oc2ccc(-c3noc(-c4n[nH]cc4NC4CCCC4)n3)cc2)cc1]

¹H NMR (400 MHz, CDCl₃) δ 1.59-1.71 (m, 4H), 1.77-1.82 (m, 2H), 2.01-2.07 (m, 2H), 3.73-3.75 (m, 1H), 4.87-4.88 (m, 1H), 7.14-7.17 (m, 3H), 7.36 (d, J = 1.2 Hz, 1H), 7.64 (d, J = 8.8 Hz, 2H), 8.15-8.18 (m, 2H).
HRMS (ESI) calcd for $C_{23}H_{21}F_3N_5O_2$ 456.1642, found 456.1679 [MH]⁺

110b

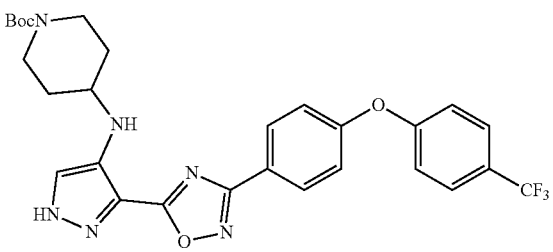 [SMILES: CC(C)(C)OC(=O)N1CCC(Nc2c[nH]nc2-c2nc(-c3ccc(Oc4ccc(C(F)(F)F)cc4)cc3)no2)CC1]

¹H NMR (400 MHz, CDCl₃) δ 1.45-1.54 (m, 2H), 1.47 (s, 9H), 2.09-2.12 (m, 2H), 3.00-3.06 (m, 2H), 3.32-3.37 (m, 1H), 4.03 (br, 2H), 7.14-7.19 (m, 4H), 7.40 (s, 1H), 7.63-7.65 (m, 2H), 8.14-8.16 (m, 2H).
HRMS (ESI) calcd for $C_{28}H_{30}F_3N_6O_4$ 571.2275, found 571.2261 [MH]⁺

111b

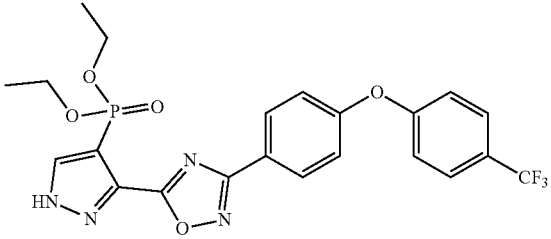 [SMILES: CCOP(=O)(OCC)c1c[nH]nc1-c1nc(-c2ccc(Oc3ccc(C(F)(F)F)cc3)cc2)no1]

¹H NMR (400 MHz, CDCl₃) δ 1.23-1.26 (m, 6H), 4.09-4.20 (m, 4H), 7.02-7.10 (m, 4H), 7.60 (d, J = 8.4, 2H), 8.03-8.09 (m, 3H).
HRMS (ESI) calcd for $C_{22}H_{21}F_3N_4O_5P$ 509.1196, found 509.1206 [MH]⁺

112a

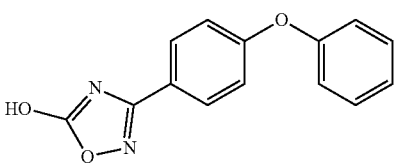 [SMILES: Oc1nc(-c2ccc(Oc3ccccc3)cc2)no1]

¹H NMR (400 MHz, DMSO-d₆) δ 7.11-7.16 (m, 4H), 7.25 (tt, J = 7.4, 1.1 Hz, 1H), 7.44-7.49 (m, 2H), 7.82 (d, J = 8.8 Hz, 2H), 12.94 (s, 1H).
HRMS (ESI) calcd for $C_{14}H_{10}N_2O_3$ 255.0784, found 255.0785 [MH]⁺

113b

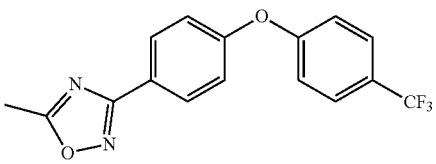 [SMILES: Cc1nc(-c2ccc(Oc3ccc(C(F)(F)F)cc3)cc2)no1]

¹H NMR (600 MHz, acetone-d₆) δ 2.66 (s, 3H), 7.25 (d, J = 8.8 Hz, 2H), 7.27 (d, J = 8.5 Hz, 2H), 7.78 (d, J = 8.5 Hz, 2H), 8.11 (d, J = 8.8 Hz, 2H).
HRMS (ESI) calcd for $C_{16}H_{12}F_3N_2O_2$ 321.0845, found 321.0847 [MH]⁺

TABLE 2.1-continued

Spectral data of compounds of Schemes 2-4.

Compound Number  Structure and data

114a

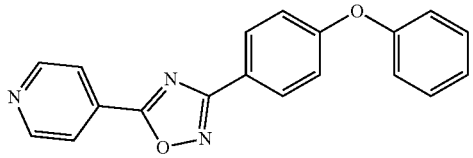 [SMILES: c1ccc(Oc2ccc(-c3noc(-c4ccncc4)n3)cc2)cc1]

¹H NMR (400 MHz, CDCl₃) δ 7.09-7.12 (m, 4H), 7.20 (t, J = 7.5 Hz, 1H), 7.48-7.43 (m, 2H), 8.06 (d, J = 6.1 Hz, 2H), 8.13 (m, 2H), 8.89 (d, J = 6.1 Hz, 2H).
HRMS (ESI) calcd for C₁₉H₁₃N₃O₂ 316.1081, found 316.1103 [MH]⁺

115a

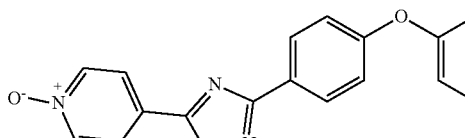

¹H NMR (400 MHz, DMSO-d₆) δ 7.09-7.28 (m, 5H), 7.39-7.55 (m, 2H), 7.94-8.20 (m, 4H), 8.43 (m, 2H).
HRMS (ESI) calcd for C₁₉H₁₃N₃O₃ 332.1030, found 332.1028 [MH]⁺

116b

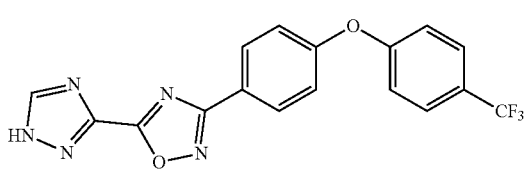 [SMILES: FC(F)(F)c1ccc(Oc2ccc(-c3noc(-c4nc[nH]n4)n3)cc2)cc1]

¹H NMR (400 MHz, DMSO-d₆) δ 7.09 (d, J = 7.2 Hz, 4H), 7.54 (d, J = 7.2 Hz, 2H), 7.71 (d, J = 6.8 Hz, 2H), 8.77 (s, 1H).
HRMS (ESI) calcd for C₁₇H₁₁F₃N₅O₂ 374.0859, found 374.0859 [MH]⁺

117b

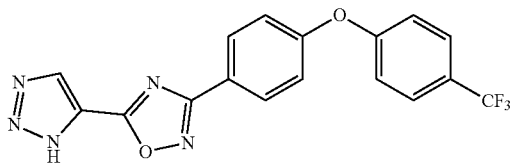 [SMILES: FC(F)(F)c1ccc(Oc2ccc(-c3noc(-c4cnn[nH]4)n3)cc2)cc1]

¹H NMR (400 MHz, DMSO-d₆) δ 7.29-7.33 (m, 4H), 7.81 (d, J = 8.8 Hz. 2H), 8.13-8.16 (m, 2H), 8.99 (d, J = 7.2, 1H).
HRMS (ESI) calcd for C₁₁H₁₁F₃N₅O₂ 374.0859, found 374.0831 [MH]⁺

119c

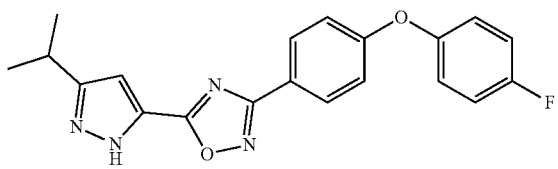 [SMILES: CC(C)c1cc(-c2nc(-c3ccc(Oc4ccc(F)cc4)cc3)no2)[nH]n1]

¹H NMR (400 MHz, CDCl₃) δ 1.37 (s, 3H), 1.39 (s, 3H), 3.10-3.17 (m, 1H), 6.82 (s, 1H), 6.83-7.12 (m, 5H), 8.13-8.16 (m, 2H), 10.76 (br s, 1H).
HRMS (ESI) calcd for C₂₀H₁₈FN₄O₂ 365.1408, found 365.1429 [MH]⁺

120b

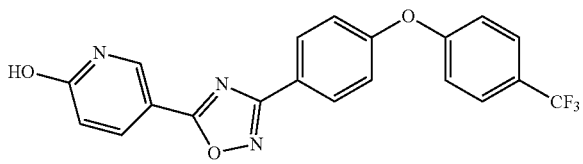 [SMILES: Oc1ccc(-c2nc(-c3ccc(Oc4ccc(C(F)(F)F)cc4)cc3)no2)cn1]

¹H NMR (400 MHz, DMSO-d₆) δ 6.54 (d, J = 9.6 Hz, 1H), 7.27-7.30 (m, 4H), 7.80 (d, J = 8.4 Hz, 2H), 8.01-8.04 (m, 1H), 8.08-8.11 (m, 2H), 8.35 (d, J = 2.8 Hz, 1H), 12.46 (s, 1H).

TABLE 2.1-continued

Spectral data of compounds of Schemes 2-4.

Compound Number | Structure and data

HRMS (ESI) calcd for $C_{20}H_{13}FN_3O_3$ 400.0904, found 400.0892 [MH]$^+$

120c

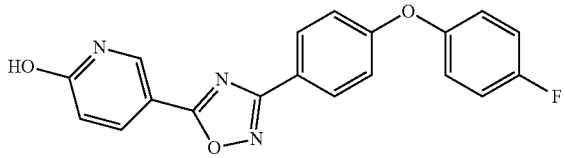 [SMILES: Oc1ccc(-c2nc(-c3ccc(Oc4ccc(F)cc4)cc3)no2)cn1]

$^1$H NMR (400 MHz, DMSO-d$_6$) δ 6.52-6.55 (m, 1H), 7.11-7.14 (m, 2H), 7.19-7.22 (m, 2H), 7.27-7.32 (m, 2H), 8.00-8.05 (m, 3H), 8.34 (d, J = 2.0 Hz, 1H), 12.45 (s, 1H).
HRMS (ESI) calcd for $C_{19}H_{13}FN_3O_3$ 350.0935, found 350.0935 [MH]$^+$ 121b

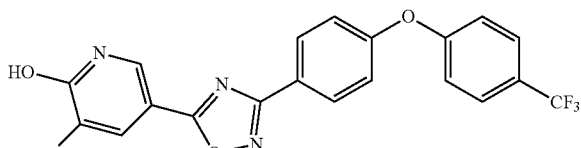

$^1$H NMR (400 MHz, DMSO-d$_6$) δ 5.56 (s, 2H), 7.02 (d, J = 2.4 Hz, 1H), 7.28-7.30 (m, 4H), 7.64 (d, J = 1.6 Hz, 1H), 7.80 (d, J = 8.4 Hz, 2H), 8.08-8.11 (m, 2H), 12.10 (s, 1H).
HRMS (ESI) calcd for $C_{20}H_{14}F_3N_4O_3$ 415.1013, found 415.0997 [MH]$^+$ 121c

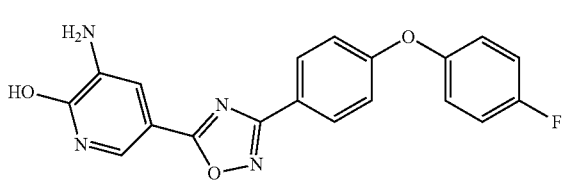

$^1$H NMR (400 MHz, DMSO-d$_6$) δ 5.55 (s, 2H), 7.01 (d, J = 2.4 Hz, 1H), 7.10-7.13 (m, 2H), 7.18-7.22 (m, 2H), 7.23-7.32 (m, 2H), 7.62 (d, J = 2.0 Hz, 1H), 8.01-8.04 (m, 2H).
HRMS (ESI) calcd for $C_{19}H_{14}FN_4O_3$ 365.1044, found 365.1031 [MH]$^+$ 122b

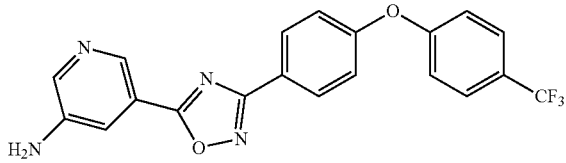 [SMILES: Nc1cncc(-c2nc(-c3ccc(Oc4ccc(C(F)(F)F)cc4)cc3)no2)c1]

$^1$H NMR (400 MHz, CDCl$_3$) δ 4.01 (br, 2H), 7.14-7.19 (m, 4H), 7.63-7.65 (m, 2H), 7.73-7.74 (m, 1H), 8.17-8.20 (m, 2H), 8.31 (d, J = 2.4 Hz, 1H), 8.83 (d, J = 1.6 Hz, 1H).
HRMS (ESI) calcd for $C_{20}H_{14}F_3N_4O_2$ 399.1063, found 399.1057 [MH]$^+$ 122c

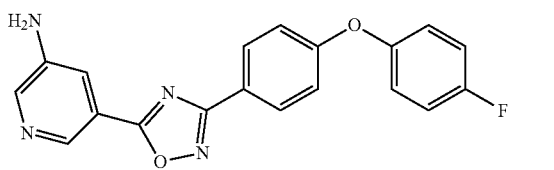 [SMILES: Nc1cncc(-c2nc(-c3ccc(Oc4ccc(F)cc4)cc3)no2)c1]

$^1$H NMR (400 MHz, CDCl$_3$) δ 3.99 (br, 2H), 7.05-7.12 (m, 6H), 7.72-7.73 (m, 1H), 8.10-8.14 (m, 2H), 8.30 (d, J = 2.4 Hz, 1H), 8.82 (d, J = 1.6 Hz, 1H).
HRMS (ESI) calcd for $C_{19}H_{14}FN_4O_2$ 349.1095, found 349.1098 [MH]$^+$ 123b

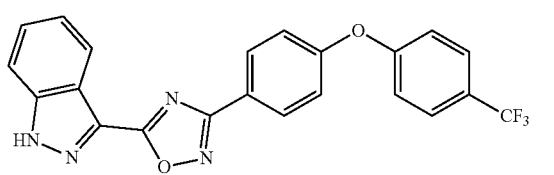 [SMILES: FC(F)(F)c1ccc(Oc2ccc(-c3noc(-c4n[nH]c5ccccc45)n3)cc2)cc1]

$^1$H NMR (400 MHz, DMSO-d$_6$) δ 7.29-7.36 (m, 4H), 7.43-7.46 (m, 1H), 7.54-7.58 (m, 1H),

TABLE 2.1-continued

Spectral data of compounds of Schemes 2-4.

| Compound Number | Structure and data |
|---|---|

7.76-7.82 (m, 3H), 8.23-8.25 (m, 2H), 8.34 (d, J = 8.4 Hz, 1H).
HRMS (ESI) calcd for $C_{22}H_{14}F_3N_4O_2$ 423.1063, found 423.1050 [MH]$^+$ 123c

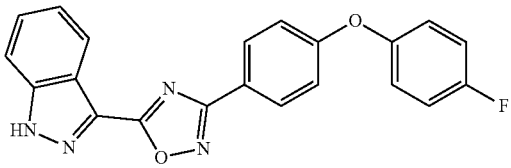 [SMILES: Fc1ccc(Oc2ccc(-c3noc(-c4n[nH]c5ccccc45)n3)cc2)cc1]

$^1$H NMR (400 MHz, DMSO-d$_6$) δ 7.17-7.24 (m, 4H), 7.29-7.34 (m, 2H), 7.42-7.46 (m, 1H), 7.54-7.76 (m, 1H), 7.77 (d, J = 8.4 Hz, 1H), 8.17-8.19 (m, 2H), 8.33 (d, J = 8.4 Hz, 1H).
HRMS (ESI) calcd for $C_{21}H_{14}FN_4O_2$ 373.1095, found 373.1112 [MH]$^+$ 124a

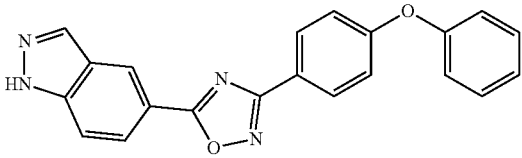 [SMILES: c1ccc(Oc2ccc(-c3noc(-c4ccc5[nH]ncc5c4)n3)cc2)cc1]

$^1$H NMR (400 MHz, CDCl$_3$) δ 7.09-7.13 (m, 4H), 7.19 (tt, J = 7.4, 1.1 Hz, 1H), 7.40 (dd, J = 8.6, 8.4 Hz, 2H), 7.66 (d, J = 8.8 Hz, 1H), 8.16 (d, J = 8.8 Hz, 2H), 8.24-8.27 (m, 2H), 8.72 (s, 1H).
HRMS (ESI) calcd for $C_{21}H_{14}N_4O_2$ 377.1009, found 377.1012 [MNa]$^+$ 125b

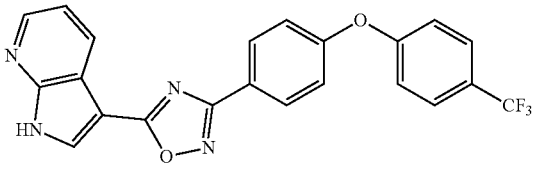 [SMILES: FC(F)(F)c1ccc(Oc2ccc(-c3noc(-c4c[nH]c5ncccc45)n3)cc2)cc1]

$^1$H NMR (400 MHz, CDCl$_3$) δ 7.15-7.21 (m, 4H), 7.41-7.44 (m, 1H), 7.65 (d, J = 8.4 Hz, 2H), 8.23-8.26 (m, 2H), 8.35 (s, 1H), 8.52-8.54 (m, 1H), 8.76-8.78 (m, 1H).
HRMS (ESI) calcd for $C_{22}H_{14}F_3N_4O_2$ 423.1063, found 423.1082 [MH]$^+$ 125c

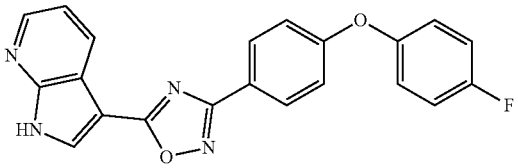 [SMILES: Fc1ccc(Oc2ccc(-c3noc(-c4c[nH]c5ncccc45)n3)cc2)cc1]

$^1$H NMR (400 MHz, DMSO-d$_6$) δ 7.13-7.16 (m, 2H), 7.19-7.23 (m, 2H), 7.28-7.33 (m, 2H), 7.35-7.38 (m, 1H), 8.11 (d, J = 2.4 Hz, 1H), 8.14 (s, 1H), 8.42-8.43 (m, 1H), 8.55 (d, J = 8.0 Hz, 1H), 8.60 (d, J = 2.4 Hz, 1H), 12.87 (s, 1H).
HRMS (ESI) calcd for $C_{21}H_{14}FN_4O_2$ 373.1095, found 373.1093 [MH]$^+$ 126c

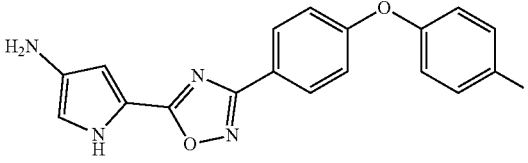

$^1$H NMR (400 MHz, CDCl$_3$) δ 3.21 (br s, 2H), 6.61 (s, 1H), 6.69 (s, 1H), 7.02-7.09 (m, 6H), 8.01-8.06 (m, 2H), 9.01 (s, 1H).
HRMS (ESI) calcd for $C_{18}H_{14}FN_4O_2$ 337.1095, found 337.1093 [MH]$^+$ TABLE 2.1-continued Spectral data of compounds of Schemes 2-4.

| Compound Number | Structure and data |
|---|---|
| 127c | 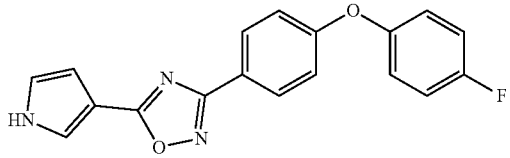 [SMILES: Fc1ccc(Oc2ccc(-c3noc(-c4cc[nH]c4)n3)cc2)cc1] |
| ¹H NMR | (400 MHz, CDCl₃) δ 6.40-6.43 (m, 1H), 7.03-7.16 (m, 7H), 8.06-8.10 (m, 2H), 9.34 (br s, 1H). |
| HRMS (ESI) | calcd for $C_{18}H_{13}FN_3O_2$ 322.0986, found 322.0984 [MH]⁺ |
| 128a | 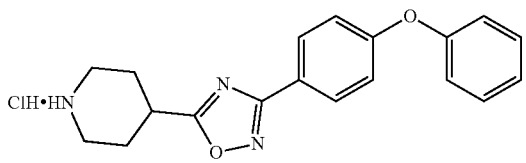 |
| ¹H NMR | (400 MHz, DMSO-d₆) δ 1.98-2.28 (m, 4H), 3.03-3.36 (m, 4H), 3.51 (m, 1H), 7.12-7.15 (m, 4H), 7.24 (tt, J = 7.4, 1.1 Hz), 7.47 (m, 2H), 8.01 (d, J = 8.9 Hz), 9.06 (m, 2H). |
| HRMS (ESI) | calcd for $C_{19}H_{19}N_3O_2$ 322.1550, found 322.1552 [MH]⁺ |
| 131a | 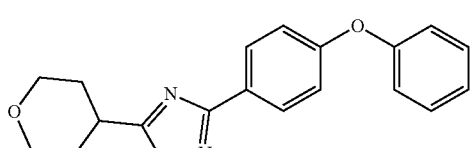 |
| ¹H NMR | (400 MHz, CDCl₃) δ 2.02-2.10 (m, 4H), 3.25 (m, 1H), 3.58 (m, 2H), 4.07 (m, 2H), 7.05-7.09 (m, 4H), 7.18 (tt, J = 7.4, 1.1 Hz, 1H), 7.39 (m, 2H), 8.04 (d, J = 8.9 Hz, 2H). |
| HRMS (ESI) | calcd for $C_{19}H_{18}N_2O_3$ 323.1390, found 323.1403 [MH]⁺ |
| 132a | 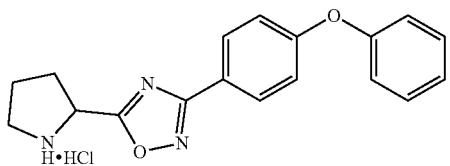 |
| ¹H NMR | (400 MHz, DMSO-d₆) δ 2.22 (s, 2H), 2.44 (s, 1H), 2.58 (s, 1H), 3.65 (m, 2H), 5.18, (s, 1H), 7.01-7.06 (m, 4H), 7.17 (t, J = 7.5 Hz, 1H), 7.37 (t, J = 7.8 Hz, 2H), 8.00 (d, J = 8.3 Hz, 2H), 10.23 (s, 1H), 11.14 (s, 1H). |
| HRMS (ESI) | calcd for $C_{18}H_{18}N_3O_2$ 308.1394, found 308.1403 [MH]⁺ |
| 133b | 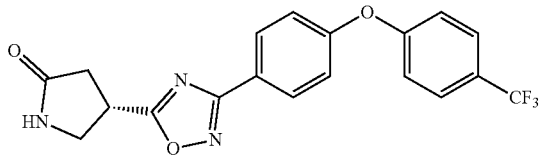 [SMILES: O=C1C[C@H](c2nc(-c3ccc(Oc4ccc(C(F)(F)F)cc4)cc3)no2)CN1] |
| ¹H NMR | (500 MHz, CDCl₃) δ 2.43-2.53 (m, 2H), 2.57-2.64 (m, 1H), 2.68-2.76 (m, 1H), 5.05-5.06 (m, 1H), 6.83 (s, 1H), 7.12 (d, J = 8.5 Hz, 4H), 7.62 (d, J = 8.5 Hz, 2H), 8.07 (d, J = 8.5 Hz, 2H). |
| 134b | 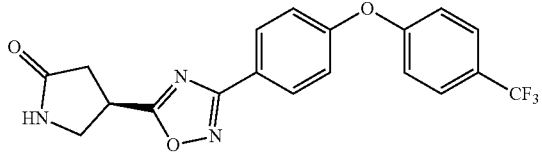 [SMILES: O=C1C[C@@H](c2nc(-c3ccc(Oc4ccc(C(F)(F)F)cc4)cc3)no2)CN1] |
| ¹H NMR | (500 MHz, CDCl₃) δ 2.42-2.51 (m, 2H), 2.57-2.63 (m, 1H), 2.66-2.74 (m, 1H), 5.04- |

TABLE 2.1-continued

Spectral data of compounds of Schemes 2-4.

| Compound Number | Structure and data |
|---|---|
| | 5.07 (m, 1H), 7.11 (d, J = 8.5 Hz, 4H), 7.62 (d, J = 8.5 Hz, 2H), 8.06 (d, J = 8.5 Hz, 2H). |
| 135b | 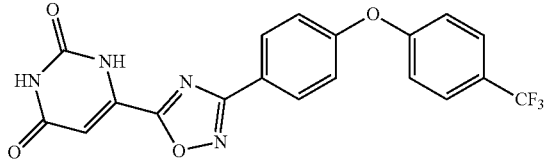 [SMILES: O=c1cc(-c2nc(-c3ccc(Oc4ccc(C(F)(F)F)cc4)cc3)no2)[nH]c(=O)[nH]1] |
| ¹H NMR | (400 MHz, DMSO-d₆) δ 6.40 (d, J = 1.6 Hz, 1H), 7.29-7.34 (m, 4H), 7.81 (d, J = 8.8 Hz, 2H), 8.13-8.15 (m, 2H), 11.56 (s, 1H), 11.87 (s, 1H). |
| HRMS (ESI) | calcd for $C_{19}H_{11}F_3N_4O_4$ 417.0805, found 417.0805 [MH]⁺ |
| 136a | 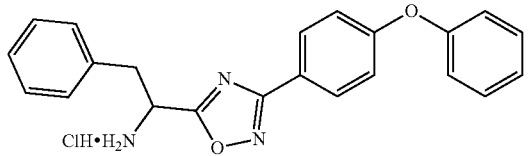 |
| ¹H NMR | (400 MHz, DMSO-d₆) δ 3.29-3.33 (m, 1H), 3.50-3.54 (m, 1H), 5.15-5.18 (m, 1H), 7.13-7.16 (m, 4H), 7.21-7.32 (m, 6H), 7.47 (t, J = 8.3 Hz, 2H), 7.99 (d, J = 8.6 Hz, 2H), 9.34 (s, 3H). |
| HRMS (ESI) | calcd for $C_{22}H_{20}N_3O_2$ 358.1550, found 358.1547 [MH]⁺ |
| 137a | 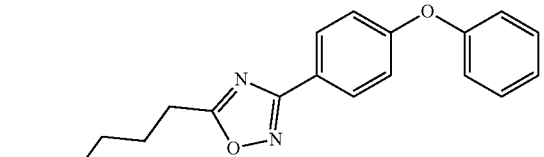 |
| ¹H NMR | (600 MHz, DMSO-d₆) δ 1.49 (quint, J = 7.4 Hz, 2H), 1.81 (quint, J = 7.4 Hz, 2H), 2.63 (t, J = 7.4 Hz, 2H), 3.00 (t, J = 7.4 Hz, 2H), 7.12-7.14 (m, 4H), 7.24 (t, J = 7.4 Hz, 1H), 7.46 (t, J = 7.4 Hz, 2H), 8.00 (d, J = 8.8 Hz, 2H). |
| HRMS (ESI) | calcd for $C_{18}H_{20}N_3O_2$ 310.1550, found 310.1523 [MH]⁺ |

TABLE 2.2

MIC data for various compounds of the invention.

| Oxadiazole antibacterials Compound structure | ID No. | LogP | CLogP | *E. faecium* NCTC 7171 MH | MH+ BSA | *S. aureus* ATCC 29213 MH | MH+ BSA |
|---|---|---|---|---|---|---|---|
| 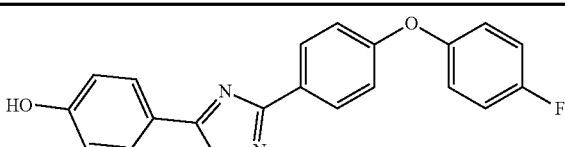 | EL-188B | 5.68 | 5.51 | 1 | 64 | 1 1 | 64 64 |
| 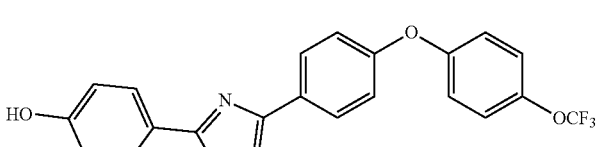 | MAB-02-185 | 7.05 | 6.4 | 1 | 32 | 2 | 32 |

TABLE 2.2-continued

MIC data for various compounds of the invention.

| Oxadiazole antibacterials Compound structure | ID No. | LogP | CLogP | E. faecium NCTC 7171 MH | MH+ BSA | S. aureus ATCC 29213 MH | MH+ BSA |
|---|---|---|---|---|---|---|---|
| | EL-228(b) | 5.84 | 5.84 | 2 | 128 | 2 | 128 |
| | SAT-207-036 | 6.61 | 6.33 | 2 | 61 2 | 4 | 64 64 |
| | ES202060 | 6.7 | 6.32 | 2 | >128 2 | 2 | >128 128 |
| | ES175037 | 6.35 | 6.24 | 1 | >64 | 2 | >256 |
| | MAB-01-151A | 6.08 | 5.84 | 2 | 128 | 2 | 128 |
| | MAB-01-162A | 6.08 | 5.86 | 2 | 64 | 2 | 64 |
| | ES181071 | 5.98 | 5.37 | 2 | >128 | 4 | 128 |

TABLE 2.2-continued

MIC data for various compounds of the invention.

| Oxadiazole antibacterials Compound structure | ID No. | LogP | CLogP | E. faecium NCTC 7171 MH | MH+ BSA | S. aureus ATCC 29213 MH | MH+ BSA |
|---|---|---|---|---|---|---|---|
| [4-hydroxyphenyl-oxadiazole-phenyl-O-phenyl(NO2)] | MAB-01-258A | ? | 4.84 | 2 | 128 | 4 | >128 |
| [4-hydroxyphenyl-oxadiazole-phenyl(I)-O-phenyl] | ES175081 | 6.88 | 6.22 | 2 | 64 | 4 | >128 |
| [4-hydroxyphenyl-oxadiazole-phenyl-O-phenyl(I)] | MAB-01-82A | 6.88 | 6.22 | 2 | 128 | 2 | 128 |
| [4-hydroxyphenyl-oxadiazole-phenyl-O-phenyl(3-I)] | MAB-01-140A | 6.88 | 6.5 | 2 | 128 | 4 | 128 |
| [4-hydroxyphenyl-oxadiazole-phenyl-O-phenyl(4-I)] | MAB-01-250A | 6.88 | 6.5 | 0.5 | 64 | 4 | 128 |
| [4-hydroxyphenyl-oxadiazole-phenyl-O-phenyl(Br)] | ES181085 | 6.35 | 6.24 | 1 | 128 | 4 | 128 |
| [4-hydroxyphenyl-oxadiazole-phenyl-O-phenyl(OMe)] | MAB-02-148A | 5.4 | 5.3 | 1 | 64 | 2 | 128 |
| [4-hydroxyphenyl-oxadiazole-phenyl-O-cyclohexenyl(Br)] | SAT-187-096 | 5.36 | 5.88 | 1 | 128 | 4 | 128 |

TABLE 2.2-continued

MIC data for various compounds of the invention.

| Oxadiazole antibacterials Compound structure | ID No. | LogP | CLogP | *E. faecium* NCTC 7171 MH | MH+ BSA | *S. aureus* ATCC 29213 MH | MH+ BSA |
|---|---|---|---|---|---|---|---|
| | SAT-207-008 | 4.95 | 5.32 | 1 | 128 | 4 | 128 |
| | EL-119(a) | 5.45 | 5.02 | 1 | 128 | 4 | >128 |
| | SAT-187-065 | 4.66 | 5.22 | 2 | 64 | 0.5 8 | 64 >128 |
| | SAT-187-085 | 5.58 | 6.11 | 2 | 64 | 0.5 1 | 64 64 |
| | EL-76(a) | 6.09 | 5.66 | 1 | 64 | 2 | 128 |
| | EL-78(a) | 6.25 | 5.83 | 1 | 64 | 2 | 128 |
| | EL-91(b) | 7.01 | 6.61 | 1 | 32 | 2 | 64 |
| | DR-03-235 | 4.99 | 4.79 | 2 | 32 | 0.5-1 | 32 |

TABLE 2.2-continued

MIC data for various compounds of the invention.

| Oxadiazole antibacterials Compound structure | ID No. | LogP | CLogP | *E. faecium* NCTC 7171 MH | MH+ BSA | *S. aureus* ATCC 29213 MH | MH+ BSA |
|---|---|---|---|---|---|---|---|
| | POD-125-81 | 5.11 | 4.8 | 2 | 64 | 4 | 64 |
| | POD-125-89 | 6.19 | 5.87 | 2 | >128 | 2 | >128 |
| | | | | | | 4 | >128 |
| | SAT-169-090 | 6.35 | 5.98 | 4 | 32 | 2 | 32 |
| | | | | | | 4 | >128 |
| | ES202053A | 5.46 | 5.78 | 2 | 32 | 2 | 32 |
| | | | | | | 2 | 32 |
| | ES215039 | 5.61 | 5.92 | 2 | 32 | 2 | 32 |
| | ES215031 | 6.38 | 6.66 | 2 | 16 | 4 | 16 |
| | DR-01-203 | 4.19 | 4.87 | 4 | 64 | 2 | 32 |
| | DR-01-291 | 5.92 | 5.74 | 2 | 128 | 1 | 16 |

TABLE 2.2-continued

MIC data for various compounds of the invention.

| Oxadiazole antibacterials Compound structure | ID No. | LogP | CLogP | E. faecium NCTC 7171 MH | MH+ BSA | S. aureus ATCC 29213 MH | MH+ BSA |
|---|---|---|---|---|---|---|---|
| 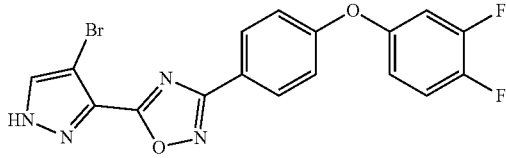 [SMILES: Fc1ccc(Oc2ccc(-c3noc(-c4n[nH]cc4Br)n3)cc2)cc1F] | DR-02-273 | 5.58 | 5.18 | 4 | 32 | 1 | 16 |

MH = Mueller Hinton broth;
BSA = bovine serum albumin.

Example 3. Minimal-Inhibitory Concentrations (MICs)

Microbial Strains.

The ESKAPE organisms (*E. faecium* NCTC (ATCC 19734), *S. aureus* ATCC 29213, *K. pneumonia* ATCC 700603, *A. baumannii* ATCC 17961, *P. aeruginosa* ATCC 17853, *E. aerogenes* ATCC 35029) and *E. coli* ATCC 25922) in the initial screen, *S. aureus* ATCC 27660, *S. epidermis* ATCC 35547, *S. haemolyticus* ATCC 29970, *S. oralis* ATCC 9811, *S. pyogenes* ATCC 49399, *B. cereus* ATCC 13061, *B. licheniformis* ATCC 12759, and *E. faecalis* ATCC 29212 were purchased from the American Type Culture Collection (Manassas, Va., USA). *S. aureus* strains NRS100, NRS119, NRS120, VRS1, and VRS2 were obtained from the Network on Antimicrobial Resistance in *Staphylococcus aureus* (Chantilly, Va., USA). *E. faecalis* strains 201 and 99, and *E. faecium* strains 119-39A and 106 were collected from Wayne State University School of Medicine.

Minimal-Inhibitory Concentration (MIC) Determination.

The procedure for MIC determination was the same as previously reported (Tran et al., *Am. J. Clin. Dermatol.* 2015; doi 10.1007/S40257-015-0125-9).

Minimal-Bactericidal Concentration (MBC) Determination.

The MBC of indolyl antibiotic 75b was determined by incubation of $1.5\times10^5$ cells of *S. aureus* ATCC29213, *S. aureus* ATCC 27660, and *E. faecium* NCTC7171 at MIC, 2×MIC, and 4×MIC. Aliquots of 10 μL (corresponding to $1.5\times10^4$ cells) were plated on agar plates, incubated for 48 h, and colonies were counted in the presence and absence of antibiotic 75c. The MBC was the concentration of antibiotic 75b that resulted in >1000-fold reduction in colonies.

Plasma Protein Binding.

Plasma protein binding was determined using human plasma and a rapid equilibrium dialysis device (Pierce Biotechnology, Thermo Scientific, Waltham, Mass., USA). Human plasma was thawed and centrifuged at 1200 g for 10 min to remove particulates. A 200-4 aliquot of human plasma was added to the sample chamber and 350 μL of 0.1 M phosphate buffered saline (pH 7.4) containing 0.15 mM sodium chloride was added to the adjacent chamber. A 2-μL aliquot of a stock solution of the compounds at a concentration of 1 mM in DMSO was diluted with human plasma to a final drug concentration of 10 μM and added to the sample chamber. The compounds were dialyzed at 37° C. in an orbital shaker for 6 h. Aliquots (50 μL) were taken from the buffer chamber (representing the free concentration) and from the plasma chamber (representing the total concentration) and mixed with 100 μL of internal standard in acetonitrile to a final concentration of 5 μM. Samples were analyzed by UPLC with UV detection at 285 nm. The plasma protein binding ratio (B %) was calculated according to the following equation:

$$B\% = (C_p - C_f)/C_p \times 100$$

where $C_p$ and $C_f$ are the total plasma concentration and the free concentration of compound, respectively.

XTT Cytotoxicity Assay.

The XTT cytotoxicity assay was performed in triplicated using HepG2 cells (ATCC HB-8065), as previously described (Tran et al., *Am. J. Clin. Dermatol.* 2015; doi 10.1007/S40257-015-0125-9). The $IC_{50}$ values were calculated with GraphPad Prism 5 (GraphPad Software, Inc., San Diego, Calif., USA).

Animals.

Female ICR mice (6-8 weeks old, ~20-g body weight) were used for the PK and peritonitis studies. Animals were purchased from Harlan Laboratories, Inc. (Indianapolis, Ind., USA) and given Teklad 2019 Extruded Rodent Diet and water ad libitum. Mice were maintained in polycarbonate shoebox cages with ¼" corncob (The Andersons Inc., Maumee, Ohio) and Alpha-dri (Sheperd Specialty Papers, Inc., Richland, Mich.) bedding under 12-h light/12-h dark cycle at 72±2° F.

Fast Pharmacokinetic (PK) Studies.

For fast PK studies, the compounds were dissolved in 10% DMSO/25% Tween-80/65% water at a concentration of 5 mg/mL. The dosing formulations were sterilized by filtration through a 0.2 μm, 13 mm diameter PTFE membrane attached to an Acrodisc syringe filter (Pall Life Sciences, Ann Arbor, Mich., USA). Mice (n=2 per time point) were given 100 μL of the test compound(s) intravenously (iv), equivalent to 20 mg/kg. Terminal blood was collected at 5 min, 40 min, 2 h, 4 h, and 8 h; blood was centrifuged at 1200 g for 10 min to harvest plasma.

Full PK Studies.

Antibiotic 75b was dissolved in 10% DMSO/25% Tween-80/65% water at a concentration of 5 mg/mL. Mice (n=3 per time point per route of administration) were administered 100 μL of 75b (equivalent to 20 mg/kg) iv. A separate group of mice was given 100 μL of 75b (equivalent to 20 mg/kg) orally (po). Terminal blood was collected in heparin by cardiac puncture at 2, 5, 10, 20, and 40 min, and at 1, 2, 3, 4, 8, and 24 h after iv administration and at 0.5, 1, 2, 3, 4, 6, 9, 24, and 36 h after po administration. Blood was centrifuged at 1200 g for 10 min to obtain plasma. Plasma samples were stored at −80° C. until analysis.

Bioanalytical Method.

Plasma (50-4, aliquot) was mixed with 100 µL of acetonitrile containing internal standard (final concentration 8 µg/mL). After centrifugation at 10000 g for 10 min, the supernatant was analyzed by ultraperformance liquid chromatography (UPLC) with UV detection at 285 nm. A Waters Acquity UPLC System (Waters Corporation, Milford, Mass., USA), consisting of a binary pump, an autosampler, a column heater, and a photodiode array detector was used. An Acquity UPLC C18 1.7 µm, 2.1 mm i.d.×50 mm column was used. Elution was at 0.5 mL/min with 70% A/30% B for 2 min, followed by a 10-min linear gradient to 10% A/90% B, then 70% A/30% B for 2 min, where A=0.1% formic acid/water and B=0.1% formic acid/acetonitrile. Monitoring was by UV detection at 285 nm. Calibration curves for each compound were prepared in control plasma containing internal standard. The concentrations in the PK samples were obtained using peak area ratio to the internal standard and the calibration curve regression analysis parameters. The methods were linear from 0.01 to 100 µg/mL; coefficients of determination $R^2$ range from 0.98 to 0.99.

Pharmacokinetic Parameters.

The area under the curve (AUC), clearance (CL), volume of distribution (Vd), and terminal half-life were calculated using Phoenix WinNonlin 6.3 (Certara LP, St Louis, Mo., USA) noncompartmental analysis using uniform weighing. Half-lives were estimated from the linear portion of the initial or terminal phase of the concentration-time data by linear regression, where the slope of the line was the rate constant k and $t_{1/2}=\ln 2/k$.

Mouse Peritonitis Studies.

The mouse peritonitis model was used with *S. aureus* ATCC 27660, as described previously (Tran et al., *Am. J. Clin. Dermatol.* 2015; doi 10.1007/S40257-015-0125-9). The final bacterial inocula contained $5 \times 10^7$ cfu/mL and 5% mucin (Sigma-Aldrich Chemical Co., St Louis, Mo., USA). Just prior to inoculation, bacteria at $10^8$ cfu/mL were mixed 1:1 with 10% mucin. Mice (n=6 per group) were given 0.5 mL of the bacterial inocula intraperitoneally. Mice were given two iv doses of the compounds at 30 min and 7.5 h after infection by tail vein injection. Vehicle and positive control (vancomycin at 5 mg/kg) groups were included. Mice were monitored for 48 h, at which time the number of surviving mice were counted.

$Ed_{50}$ Determination.

The effective dose that results in survival of 50% of the mice was determined using Probit analysis (XLSTAT, New York, N.Y.). Groups of six mice per dose level were evaluated in the mouse peritonitis infection model at iv doses of 2.5, 5, 7.5, 10, 15, and 20 mg/kg and after po doses at 2.5, 5, 10, 20, and 40 mg/kg. The doses were given at 30 min and 7.5 h after infection. In addition, $ED_{50}$ values were determined for compound 75b and linezolid after a single po dose given at 1 h after infection.

TABLE 3.1

Minimal-Inhibitory concentrations (MICs) (compounds of Schemes 2-4).

| Cmpd. No. | *E. faecium* NCTC 7171 MIC (µg/mL) | *S. aureus* ATCC 29213 MIC (µg/mL) |
|---|---|---|
| 57a | 1 | 1 |
| 57b | 1 | 1 |
| 57c | 1 | 1 |
| 58a | 2 | 4 |
| 58b | 2 | 1 |
| 58c | >128 | >128 |
| 59b | 2 | 1 |
| 60a | >128 | 1 |
| 60c | 8 | 0.5 |
| 60b | 2 | 1 |
| 61a | 16 | 1 |
| 61b | >128 | 1 |
| 62a | 32 | 1 |
| 62b | 32 | 2 |
| 63a | 4 | 2 |
| 63b | 2 | 2 |
| 63c | 4 | 1 |
| 64a | 32 | 16 |
| 64b | 16 | 4 |
| 64c | 32 | 16 |
| 65a | >128 | 0.5 |
| 65b | >128 | 0.5 |
| 66b | >128 | 0.25 |
| 67b | >128 | 2 |
| 68b | 128 | 4 |
| 69b | 128 | 2 |
| 69c | 8 | 4 |
| 70a | 4 | 4 |
| 70b | 2 | 2 |
| 70c | 2 | 2 |
| 71b | 2 | 2 |
| 71c | 4 | 8 |
| 72a | >32 | >128 |
| 72b | 2 | 2 |
| 73a | 4 | 8 |
| 73b | 4 | 4 |
| 74a | 8 | 8 |
| 75a | 2 | 2 |
| 75b | 2 | 4 |
| 75c | 2 | 2 |
| 76b | 4 | 2 |
| 76c | 128 | >128 |
| 77b | 4 | 8 |
| 77c | 4 | 8 |
| 78b | 64 | 8 |
| 78c | 128 | >128 |
| 79a | >128 | 8 |
| 80a | — | >1000 |
| 80b | — | >1200 |
| 81b | — | >1000 |
| 81c | >128 | >128 |
| 82a | >32 | >32 |
| 82b | — | >1000 |
| 83b | — | 256 |
| 84c | 32 | >128 |
| 85c | >128 | >128 |
| 86b | 32 | >128 |
| 87b | 128 | >128 |
| 87c | >128 | >128 |
| 88c | 64 | >128 |
| 89c | 128 | >128 |
| 90c | >128 | >128 |
| 91c | >128 | >128 |
| 92c | 128 | >128 |
| 93b | >128 | >128 |
| 94a | >128 | >128 |
| 95a | >128 | >128 |
| 96a | 32 | >128 |
| 97a | >128 | >128 |
| 98a | >128 | >128 |
| 99a | 128 | >128 |
| 99b | >128 | >128 |
| 99c | >128 | >128 |

TABLE 3.1-continued

Minimal-Inhibitory concentrations (MICs)
(compounds of Schemes 2-4).

| Cmpd. No. | E. faecium NCTC 7171 MIC (µg/mL) | S. aureus ATCC 29213 MIC (µg/mL) |
|---|---|---|
| 100a | >128 | >128 |
| 101b | >128 | >128 |
| 101c | >128 | >128 |
| 102b | 64 | >128 |
| 102c | 32 | >128 |
| 103b | >128 | >128 |
| 104b | >128 | >128 |
| 105b | 128 | >128 |
| 106b | 128 | >128 |
| 107b | >128 | >128 |
| 108b | 16 | >128 |
| 109b | >128 | >128 |
| 110b | >128 | >128 |
| 111b | >128 | >128 |
| 112a | >128 | >128 |
| 113a | — | >1200 |
| 114a | 64 | >128 |
| 115a | 64 | >128 |
| 116b | >128 | >128 |
| 117b | >128 | 16 |
| 118c | >128 | >128 |
| 119c | 64 | >128 |
| 120b | 32 | >128 |
| 120c | 64 | >128 |
| 121b | 64 | >128 |
| 121c | 128 | >128 |
| 122b | >128 | >128 |
| 122c | 128 | >128 |
| 123b | >128 | >128 |
| 123c | 16 | >128 |
| 124a | 64 | >128 |
| 125b | 32 | >128 |
| 125c | 64 | >128 |
| 126c | 64 | 128 |
| 127c | >128 | >128 |
| 128a | 16 | 32 |
| 129a | >128 | >128 |
| 129c | >128 | >128 |
| 130c | >128 | >128 |
| 131a | >128 | >128 |
| 132a | 64 | 64 |
| 133b | >128 | >128 |
| 134b | >128 | >128 |
| 135b | >128 | >128 |
| 136a | >128 | >128 |
| 137a | 32 | 64 |

Figure 2:
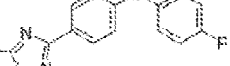
FIG. 2. Compounds and inhibitory data. MH=Mueller Hinton broth; BSA=bovine serum albumin.
Figure 2:
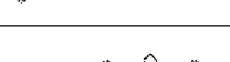
Figure 2:
Figure 2:
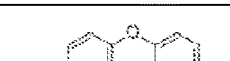
Figure 2:
Figure 2:
Figure 2:
Figure 2:
Figure 2:
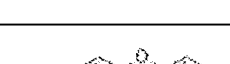
Figure 2:
Figure 2:
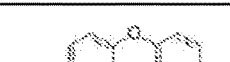
Figure 2:
Figure 2:
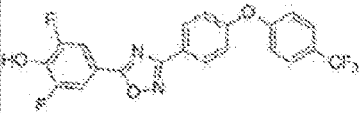
Figure 2:
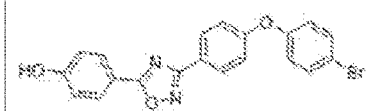
Figure 2:
Figure 2:
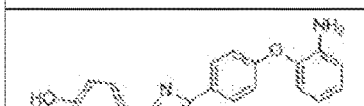
Figure 2:
Figure 2:
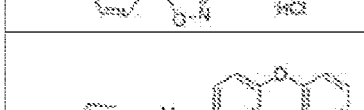
Figure 2:
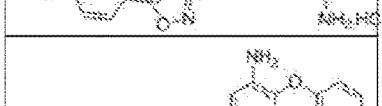
Figure 2:
Figure 2:
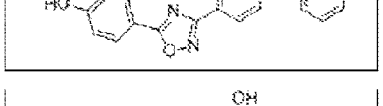
Figure 2:
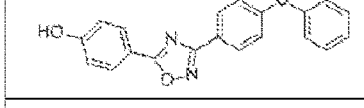
Figure 2:
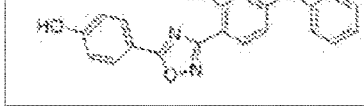
Figure 2:
Figure 2:
Figure 2:
Figure 2:
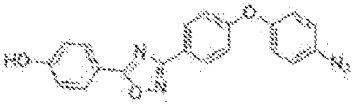
Figure 2:
Figure 2:
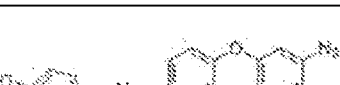
Figure 2:
Figure 2:
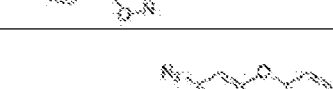
Figure 2:
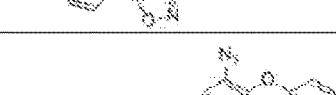
Figure 2:
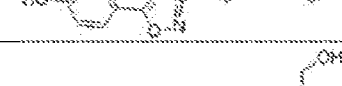
Figure 2:
Figure 2:
Figure 2:
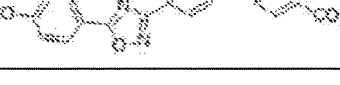
Figure 2:
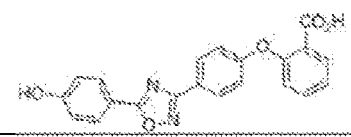
Figure 2:
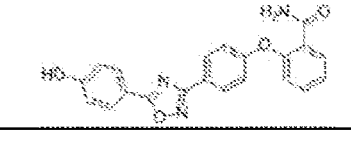
Figure 2:
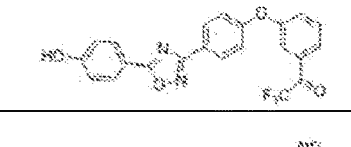
Figure 2:
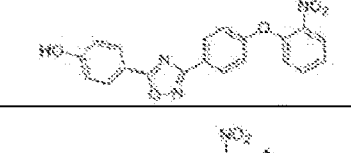
Figure 2:
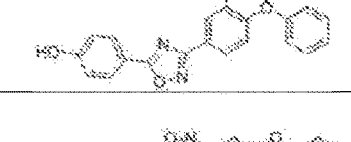
Figure 2:
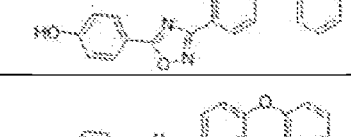
Figure 2:
Figure 2:
Figure 2:
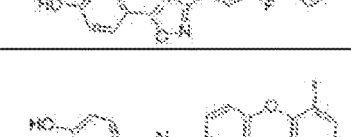
Figure 2:
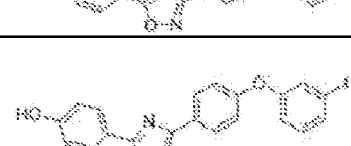
Figure 2:
Figure 2:
Figure 2:
Figure 2:
Figure 2:
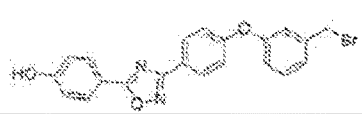
Figure 2:
Figure 2:
Figure 2:
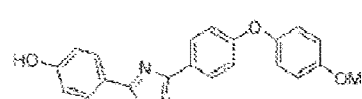
Figure 2:
Figure 2:
Figure 2:
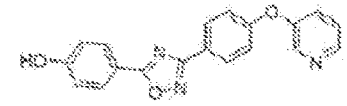
Figure 2:
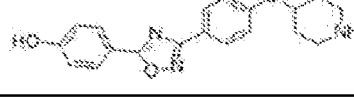
Figure 2:
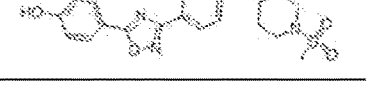
Figure 2:
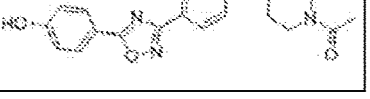
Figure 2:
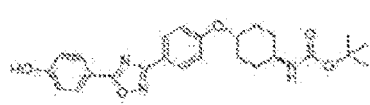
Figure 2:
Figure 2:
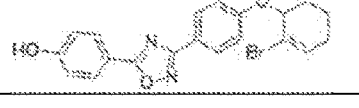
Figure 2:
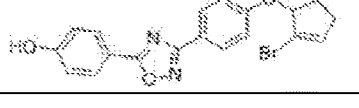
Figure 2:
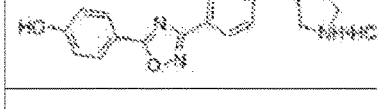
Figure 2:
Figure 2:
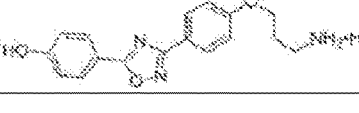
Figure 2:
Figure 2:
Figure 2:
Figure 2:
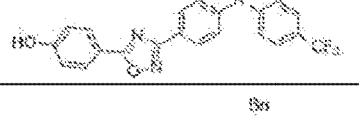
Figure 2:
Figure 2:
Figure 2:
Figure 2:
Figure 2:
Figure 2:
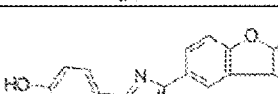
Figure 2:
Figure 2:
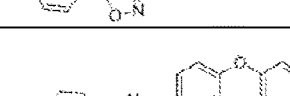
Figure 2:
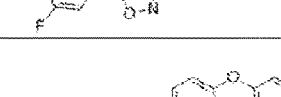
Figure 2:
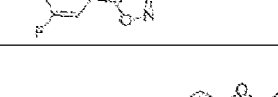
Figure 2:
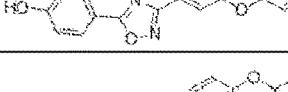
Figure 2:
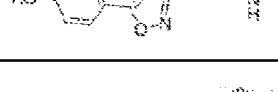
Figure 2:
Figure 2:
Figure 2:
Figure 2:
Figure 2:
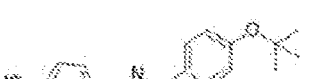
Figure 2:
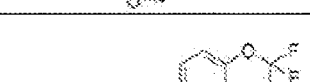
Figure 2:
Figure 2:
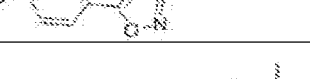
Figure 2:
Figure 2:
Figure 2:
Figure 2:
Figure 2:
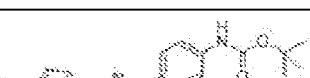
Figure 2:
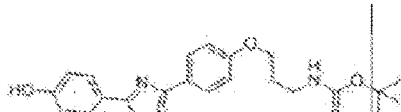
Figure 2:
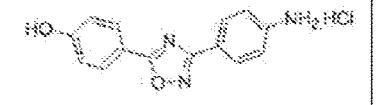
Figure 2:
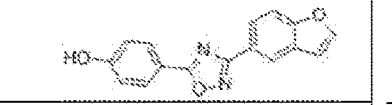
Figure 2:
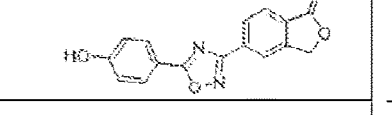
Figure 2:
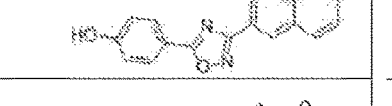
Figure 2:
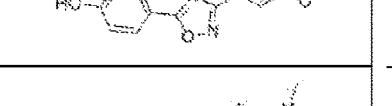
Figure 2:
Figure 2:
Figure 2:
Figure 2:
Figure 2:
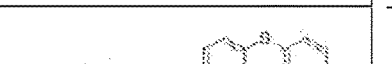
Figure 2:
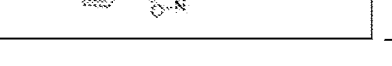
Figure 2:
Figure 2:
Figure 2:
Figure 2:
Figure 2:
Figure 2:
Figure 2:
Figure 2:
Figure 2:
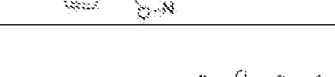
Figure 2:
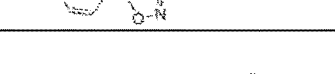
Figure 2:
Figure 2:
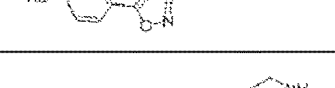
Figure 2:
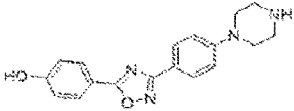
Figure 2:
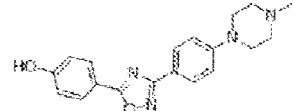
Figure 2:
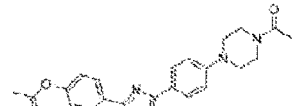
Figure 2:
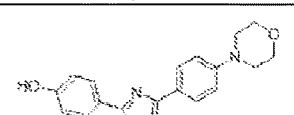
Figure 2:
Figure 2:
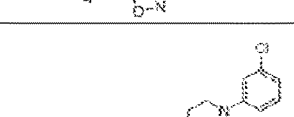
Figure 2:
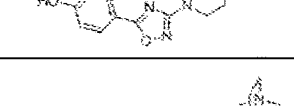
Figure 2:
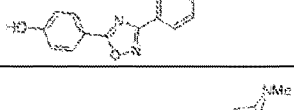
Figure 2:
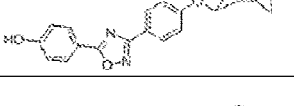
Figure 2:
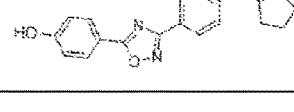
Figure 2:
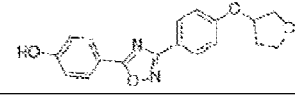
Figure 2:
Figure 2:
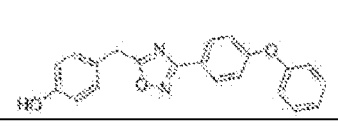
Figure 2:
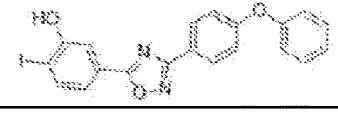
Figure 2:
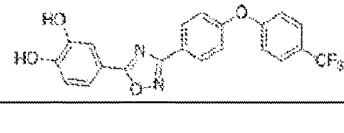
Figure 2:
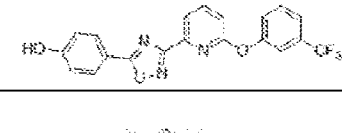
Figure 2:
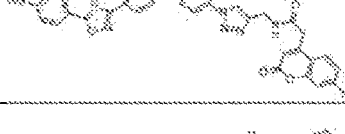
Figure 2:
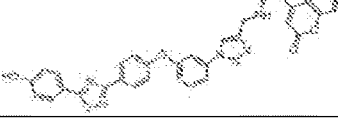
Figure 2:
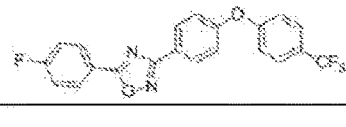
Figure 2:
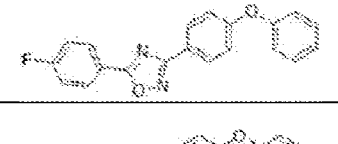
Figure 2:
Figure 2:
Figure 2:
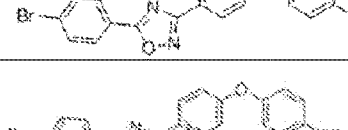
Figure 2:
Figure 2:
Figure 2:
Figure 2:
Figure 2:
Figure 2:
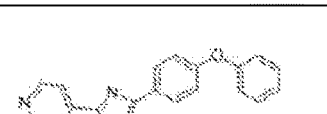
Figure 2:
Figure 2:
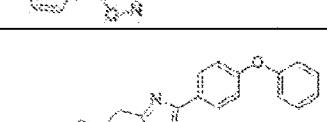
Figure 2:
Figure 2:
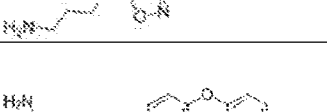
Figure 2:
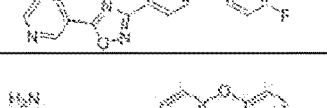
Figure 2:
Figure 2:
Figure 2:
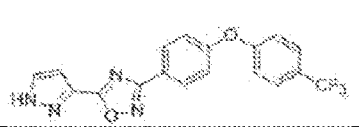
Figure 2:
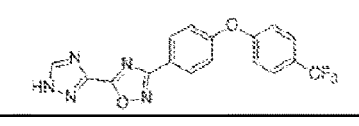
Figure 2:
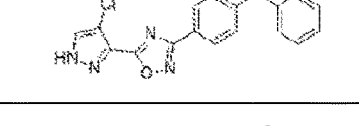
Figure 2:
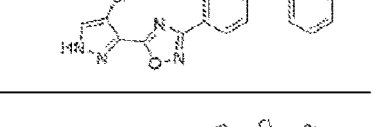
Figure 2:
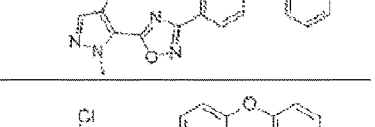
Figure 2:
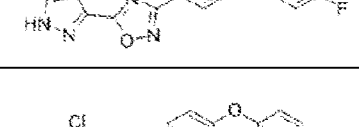
Figure 2:
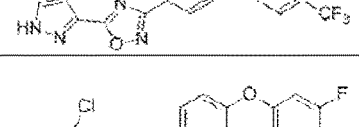
Figure 2:
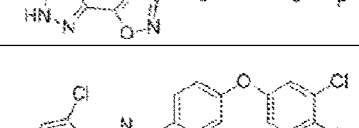
Figure 2:
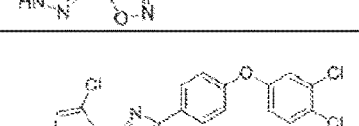
Figure 2:
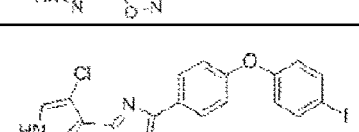
Figure 2:
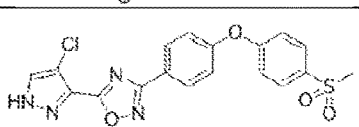
Figure 2:
Figure 2:
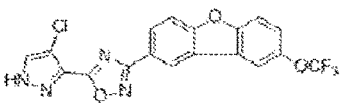
Figure 2:
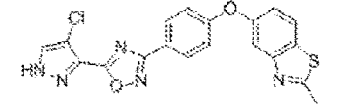
Figure 2:
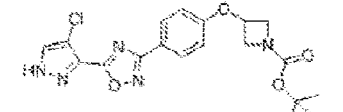
Figure 2:
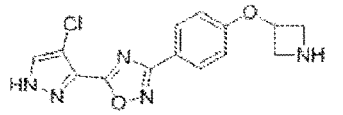
Figure 2:
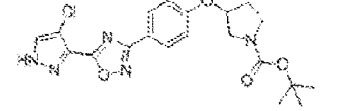
Figure 2:
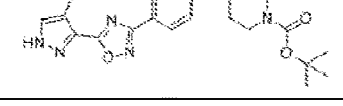
Figure 2:
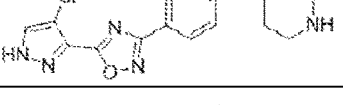
Figure 2:
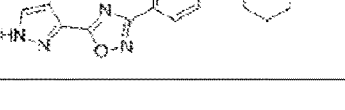
Figure 2:
Figure 2:
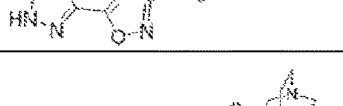
Figure 2:
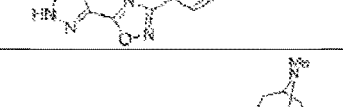
Figure 2:
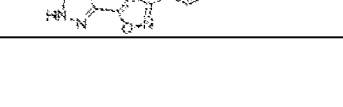
Figure 2:
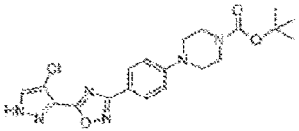
Figure 2:
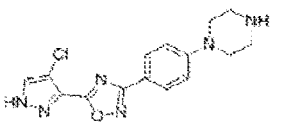
Figure 2:
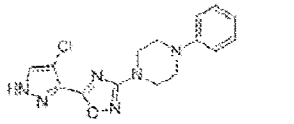
Figure 2:
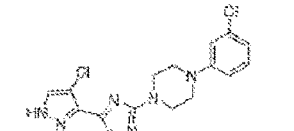
Figure 2:
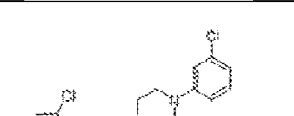
Figure 2:
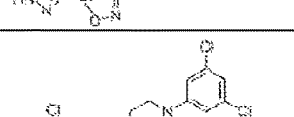
Figure 2:
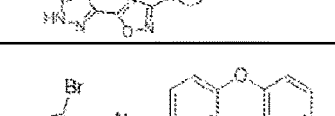
Figure 2:
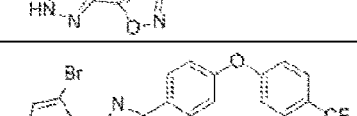
Figure 2:
Figure 2:
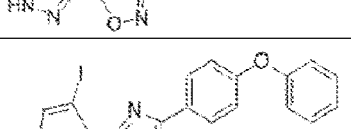
Figure 2:
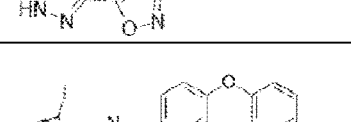
Figure 2:
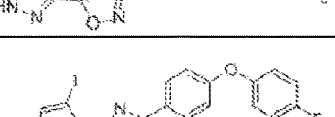
Figure 2:
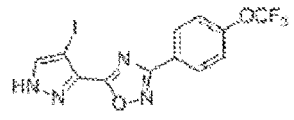
Figure 2:
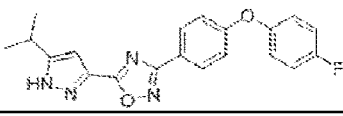
Figure 2:
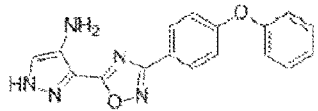
Figure 2:
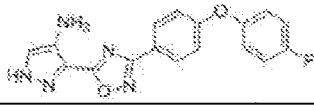
Figure 2:
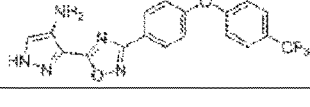
Figure 2:
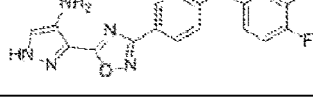
Figure 2:
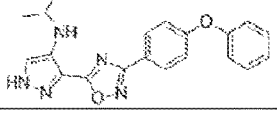
Figure 2:
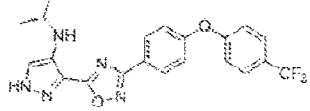
Figure 2:
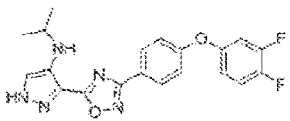
Figure 2:
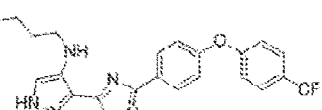
Figure 2:
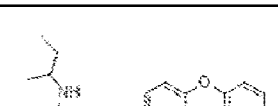
Figure 2:
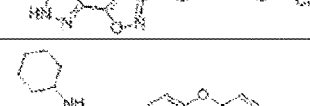
Figure 2:
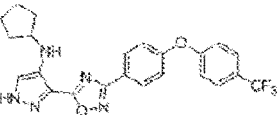
Figure 2:
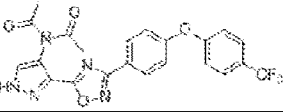
Figure 2:
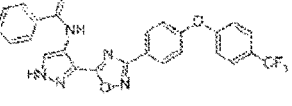
Figure 2:
Figure 2:
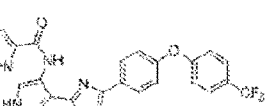
Figure 2:
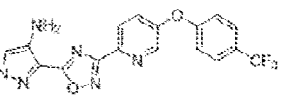
Figure 2:
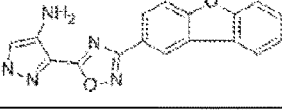
Figure 2:
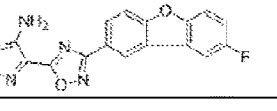
Figure 2:
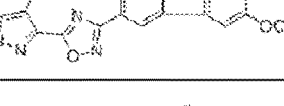
Figure 2:
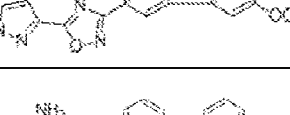
Figure 2:
Figure 2:
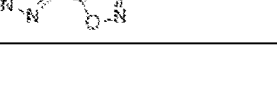
Figure 2:
Figure 2:
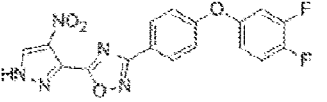
Figure 2:
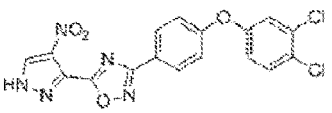
Figure 2:
Figure 2:
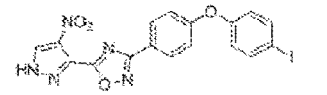
Figure 2:
Figure 2:
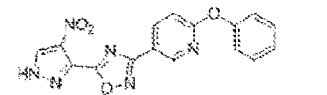
Figure 2:
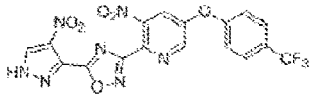
Figure 2:
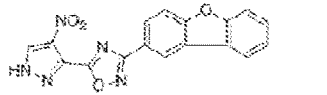
Figure 2:
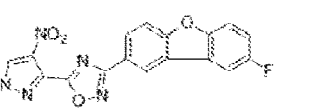
Figure 2:
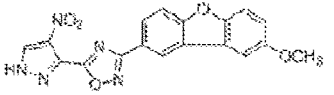
Figure 2:
Figure 2:
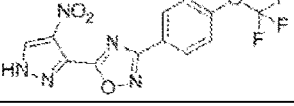
Figure 2:
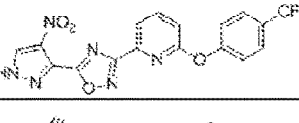
Figure 2:
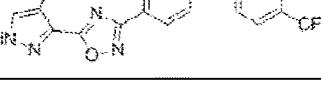
Figure 2:
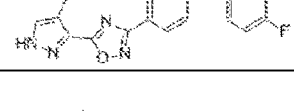
Figure 2:
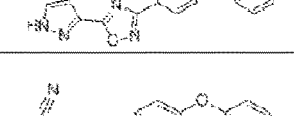
Figure 2:
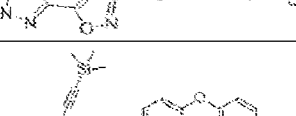
Figure 2:
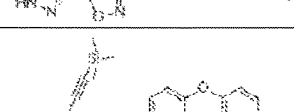
Figure 2:
Figure 2:
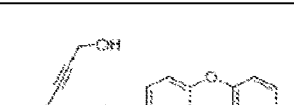
Figure 2:
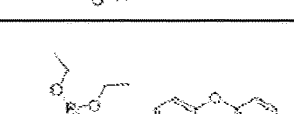
Figure 2:
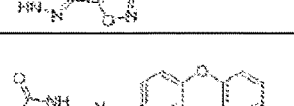
Figure 2:
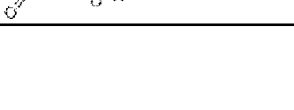
Figure 2:
Figure 2:
Figure 2:
Figure 2:
Figure 2:
Figure 2:
Figure 2:
Figure 2:
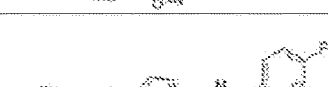
Figure 2:
Figure 2:
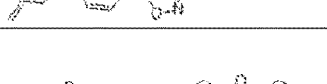
Figure 2:
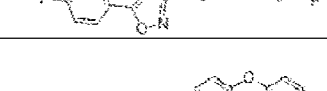
Figure 2:
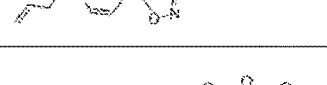
Figure 2:
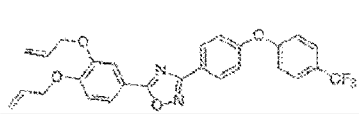
Figure 2:
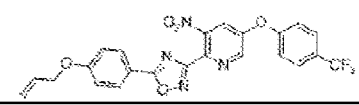
Figure 2:
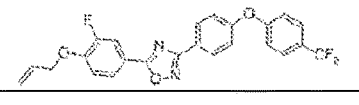
Figure 2:
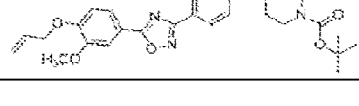
Figure 2:
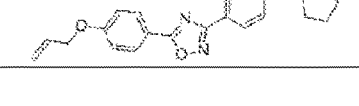
Figure 2:
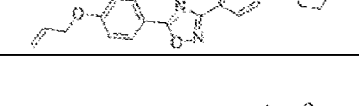
Figure 2:
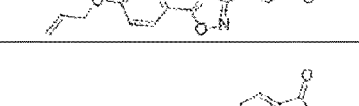
Figure 2:
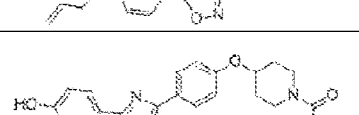
Figure 2:
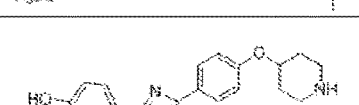
Figure 2:
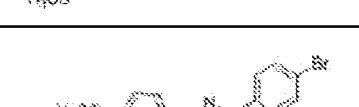
Figure 2:
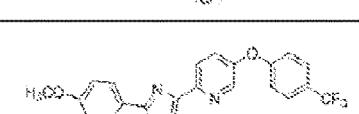
Figure 2:
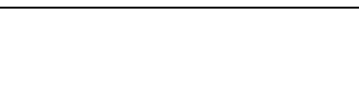
Figure 2:
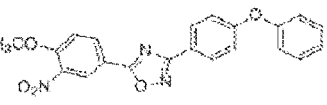
Figure 2:
Figure 2:
Figure 2:
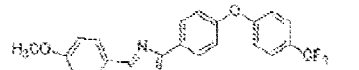
Figure 2:
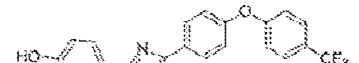
Figure 2:
Figure 2:
Figure 2:
Figure 2:
Figure 2:
Figure 2:
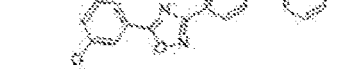
Figure 2:
Figure 2:
Figure 2:
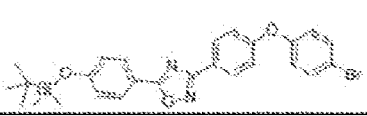
Figure 2:
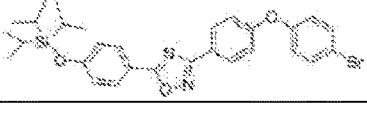
Figure 2:
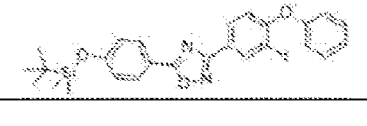
Figure 2:
Figure 2:
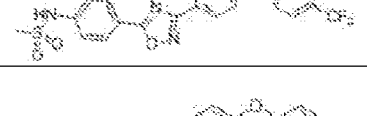
Figure 2:
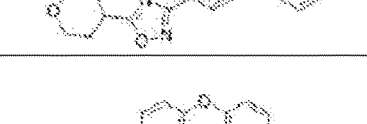
Figure 2:
Figure 2:
Figure 2:
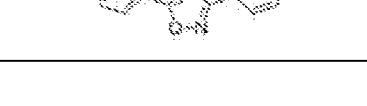
Figure 2:
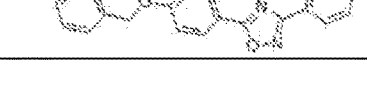
Figure 2:
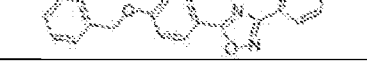
Figure 2:
Figure 2:
Figure 2:
Figure 2:
Figure 2:
Figure 2:
Figure 2:
Figure 2:
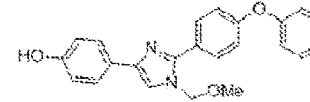
Figure 2:
Figure 2:
Figure 2:
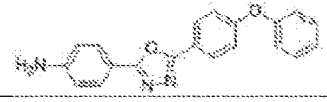
Figure 2:
Figure 2:
Figure 2:
Figure 2:
Figure 2:
Figure 2:
Figure 2:
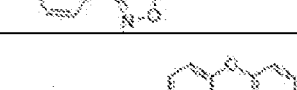
Figure 2:
Figure 2:
Figure 2:
Figure 2:
Figure 2:

Additional compounds and inhibitory data are provided in FIG. 2, where NG=no bacteria growth (or incomplete/undetermined assay); and ≥=MIC value is greater than or equal to this value. Where there are two or more numbers in a column, the first number is the MIC, the number in parentheses ( ) is the MIC with 2% BSA, and the number in curly brackets { } is the MIC in a Brain/Heart broth media.

Example 4. Preparation and Data of 1,2,4-Oxadiazole Antibiotics

The general procedure for synthesis of 1, 2, 4-oxadiazole derivatives has been previously reported (O'Daniel et al., *J. Am. Chem. Soc.* 2014, 136, 3664-3672; Spink et al., *J. Med. Chem.*, 2015, 58, 1380). Representative spectral data of the compounds are as follows.

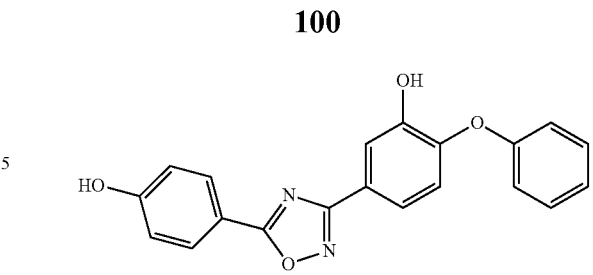

5-(5-(4-hydroxyphenyl)-1, 2, 4-oxadiazol-3-yl)-2-phenoxyphenol 51a $^1$H NMR (600 MHz, acetone-$d_6$) δ 7.02 (d, 2H, J=8.8 Hz, ArH), 7.06-7.09 (m, 3H, ArH), 7.12 (tt, 1H, J=7.4, 1.1 Hz, ArH), 7.38 (dd, 2H, J=8.7, 7.4 Hz, ArH), 7.65 (dd, 1H, J=8.5, 2.1 Hz, ArH), 7.80 (d, 1H, J=2.1 Hz, ArH), 8.09 (d, 2H J=8.8 Hz, ArH), 9.03 (br s, 2H, 2×OH); $^{13}$C NMR (150 MHz, acetone-$d_6$) δ 116.5, 116.7, 117.1, 118.6, 120.3, 121.5, 124.0, 124.6, 130.7, 131.0, 147.3, 150.1, 158.2, 162.8, 169.0, 176.6; HRMS (ESI): calcd for $C_{20}H_{15}N_2O_4$ [M+H]$^+$ 347.1026, found 347.1009.

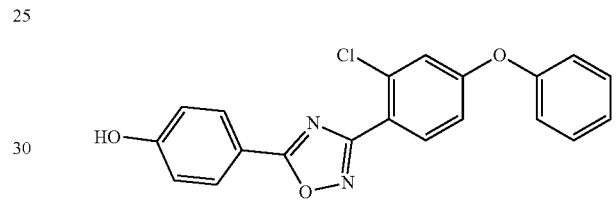

4-(3-(2-chloro-4-phenoxyphenyl)-1,2,4-oxadiazol-5-yl)phenol 52a $^1$H NMR (500 MHz, CDCl$_3$) δ 6.45 (s, 1H, OH), 6.97 (d, 2H, J=8.8 Hz, ArH), 7.00 (dd, 1H, J=8.8, 2.4 Hz, ArH), 7.09 (dd, 2H, J=8.5, 0.9 Hz, ArH), 7.13 (d, 1H, J=2.4 Hz, ArH), 7.22 (t, 1H, J=7.5 Hz, ArH), 7.41 (dd, 2H, J=8.5, 7.5 Hz, ArH), 7.95 (d, 1H, J=8.8 Hz, ArH), 8.09 (d, 2H, J=8.8 Hz, ArH); $^{13}$C NMR (125 MHz, CDCl$_3$) δ 116.4, 116.6, 120.0, 120.3, 120.5, 125.0, 130.4, 130.6, 133.1, 134.8, 155.5, 160.3, 160.4, 167.4, 175.3; HRMS (ESI): calcd for $C_{20}H_{14}ClN_2O_3$ [M+H]$^+$ 365.0687, found 365.0677.

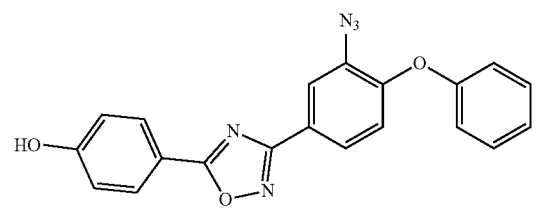 [SMILES: [N-]=[N+]=Nc1cc(-c2noc(-c3ccc(O)cc3)n2)ccc1Oc1ccccc1]

4-(3-(3-azido-4-phenoxyphenyl)-1,2,4-oxadiazol-5-yl)phenol 53a $^1$H NMR (500 MHz, acetone-$d_6$) δ 7.09 (d, 2H, J=8.7 Hz, ArH), 7.11-7.14 (m, 3H, ArH), 7.22 (tt, 1H, J=7.5, 1.0 Hz, ArH), 7.46 (dd, 2H, J=8.7, 7.5 Hz, ArH), 7.89 (dd, 1H, J=1.8, 1.3 Hz, ArH), 7.93 (dd, 1H, J=8.6, 1.8 Hz, ArH), 8.11 (d, 2H, J=8.7 Hz, ArH), 9.40 (s, 1H, OH); $^{13}$C NMR (125 MHz, acetone-$d_6$) δ 116.3, 117.2, 119.3, 120.9, 121.4, 124.5, 125.1, 125.9, 131.1, 131.1, 132.7, 152.1, 157.4, 162.9, 168.4, 176.9; HRMS (ESI): calcd for $C_{20}H_{14}N_5O_3$ [M+H]$^+$ 372.1091, found 372.1086.

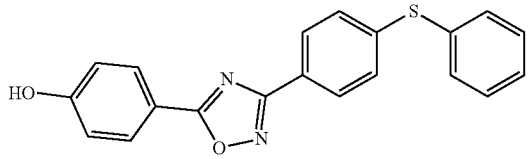 [SMILES: Oc1ccc(-c2nc(-c3ccc(Sc4ccccc4)cc3)no2)cc1]

4-(3-(4-(phenylthio)phenyl)-1,2,4-oxadiazole-5-yl) phenol 61a $^1$H NMR (500 MHz, DMSO-d$_6$) δ 6.99 (d, J=8.5 Hz, 2H), 7.39-7.45 (m, 6H), 8.00-8.03 (m, 4H), 10.57 (s, 1H). $^{13}$C NMR (125 MHz, DMSO-d$_6$) δ 114.0, 116.3, 124.4, 127.9, 128.6, 129.1, 129.9, 130.1, 132.3, 132.7, 140.5, 162.1, 167.5, 175.5. HRMS (ESI): calcd for $C_{20}H_{15}N_2O_2S$ [M+H]$^+$ 347.0849, found 347.0869.

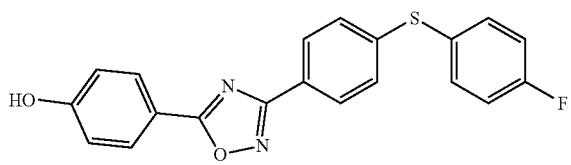

4-(3-(4-((4-fluorophenyl)thio)phenyl)-1,2,4-oxadiazole-5-yl)phenol 62a $^1$H NMR (500 MHz, DMSO-d$_6$) δ 6.99 (d, J=9.0 Hz, 2H), 7.32-7.36 (m, 4H), 7.58-7.61 (m, 2H), 7.99-8.02 (m, 4H), 10.57 (s, 1H). $^{13}$C NMR (125 MHz, DMSO-d$_6$) δ 114.0, 116.3, 117.0, 117.2, 124.2, 127.3, 127.4, 127.9, 128.3, 130.1, 135.8, 135.9, 141.1, 161.5, 162.1, 163.4, 167.5, 175.5. HRMS (ESI): calcd for $C_{20}H_{14}FN_2O_2S$ [M+H]$^+$ 365.0755, found 365.0728.

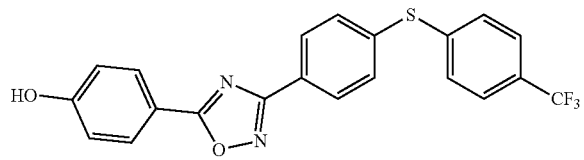 [SMILES: Oc1ccc(-c2nc(-c3ccc(Sc4ccc(C(F)(F)F)cc4)cc3)no2)cc1]

4-(3-(4-((4-trifluoromethyl)phenyl)thio) phenyl)-1,2, 4-oxadiazole-5-yl)phenol 63a $^1$H NMR (500 MHz, DMSO-d$_6$) δ 6.99-7.01 (m, 2H), 7.53 (d, J=8.0 Hz, 2H), 7.62-7.64 (m, 2H), 7.74 (d, J=8.5 Hz, 2H), 8.03-8.10 (m, 2H), 8.11-8.12 (m, 2H), 10.5 (br, 1H). $^{13}$C NMR (125 MHz, DMSO-d$_6$) δ 113.9, 116.4, 126.1, 126.3, 126.4, 128.4, 130.1, 130.2, 132.3, 136.6, 162.2, 167.4, 175.7. HRMS (ESI): calcd for $C_{21}H_{14}FN_2O_2S$ [M+H]$^+$ 415.0723, found 415.0729.

Example 5. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |

-continued

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

Propyl paraben 0.02%
Purified water q.s. to 100 g

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula (I):

A-B-C-L-D  (I)

wherein
A is 5-indolyl optionally substituted with one to three $R^X$ groups;
B is 1,2,4-oxadiazole;
C is phenyl, optionally substituted with one to four $R^X$ groups;
L is O, S, or NH;
D is phenyl, optionally substituted with one to five $R^X$ groups;
each $R^X$ is independently —H, —OH, halo, —N$_3$, —NO$_2$, —O-allyl, —C≡N, —CF$_3$, —OCF$_3$, —C(=O)CF$_3$, alkyl, alkoxy, phenyl, phenoxy, benzyl, or cycloalkyl —NR$^a$R$^b$, or —C≡C—R$^Y$;
each $R^a$ and $R^b$ are independently H, alkyl, or a nitrogen protecting group; and
$R^Y$ is —H, alkyl, hydroxyalkyl, or a silicon protecting group;
or pharmaceutically acceptable salt or solvate thereof.

2. The compound of claim 1 wherein D is phenyl, 4-CF$_3$-phenyl, or 4-F-phenyl.

3. The compound of claim 1 that is a compound of Formula (XII):

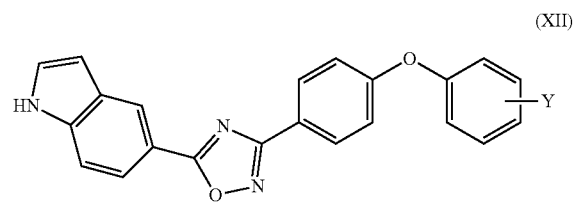

(XII)

wherein Y is H, F, or CF$_3$;
or a pharmaceutically acceptable salt or solvate thereof.

4. The compound of claim 3 wherein Y is para to the oxygen of the phenyl ring to which it is attached.

5. A compound of Formula XIII or XIV:

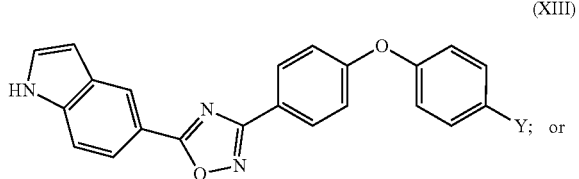

(XIII)

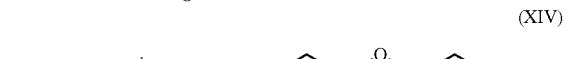

(XIV)

wherein Y is —H, —F, or —CF$_3$; and
$R^1$ is Cl, Br, I, NO$_2$, —NH((C$_1$-C$_6$)alkyl), —C≡CH, —C≡N, or —C≡CCH$_2$OH;
or a salt or solvate thereof.

6. The compound 75a, 75b, or 75c:

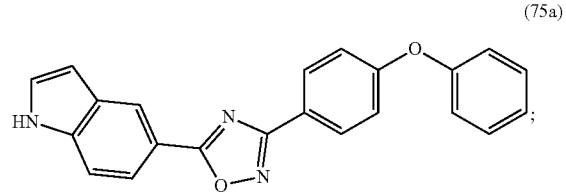

(75a)

(75b)

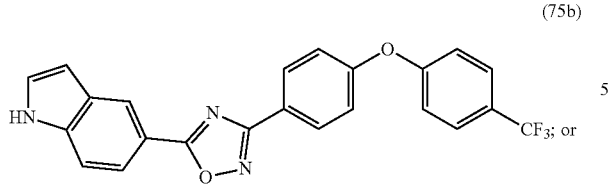

(75c)

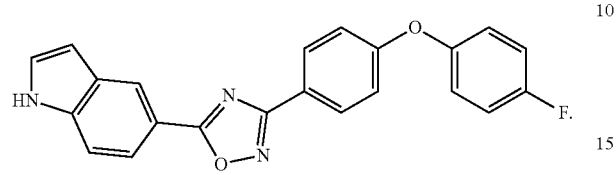

7. A method for inhibiting growth of gram positive bacteria comprising contacting gram positive bacteria with a compound of claim 1, thereby inhibiting the growth of the bacteria.

8. A method for inhibiting growth of gram positive bacteria comprising contacting gram positive bacteria with a compound of claim 3, thereby inhibiting the growth of the bacteria.

9. A method for inhibiting growth of gram positive bacteria comprising contacting gram positive bacteria with a compound of claim 5, thereby inhibiting the growth of the bacteria.

* * * * *